US011185626B2

(12) United States Patent
Schoellhammer et al.

(10) Patent No.: US 11,185,626 B2
(45) Date of Patent: Nov. 30, 2021

(54) SYSTEMS, APPARATUS, AND METHODS FOR ADMINISTERING A SUBSTANCE

(71) Applicant: MASSACHUSETTS INSTITUTE OF TECHNOLOGY, Cambridge, MA (US)

(72) Inventors: Carl Magnus Schoellhammer, Somerville, MA (US); Carlo Giovanni Traverso, Newton, MA (US); Avraham Schroeder, Binyamina (IL); Baris Polat, Pittsburgh, PA (US); Daniel Blankschtein, Brookline, MA (US); Robert S. Langer, Newton, MA (US); William Brugge, Boston, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 77 days.

(21) Appl. No.: 15/727,015

(22) Filed: Oct. 6, 2017

(65) Prior Publication Data
US 2018/0055991 A1    Mar. 1, 2018

Related U.S. Application Data

(63) Continuation of application No. PCT/US2016/026779, filed on Apr. 8, 2016.
(Continued)

(51) Int. Cl.
*A61M 3/02* (2006.01)
*A61M 37/00* (2006.01)
*A61M 31/00* (2006.01)

(52) U.S. Cl.
CPC ........ *A61M 3/0275* (2013.01); *A61M 3/0233* (2013.01); *A61M 3/0254* (2013.01);
(Continued)

(58) Field of Classification Search
CPC .............. A61M 3/0233; A61M 3/0254; A61M 3/0275; A61M 3/0279; A61M 37/0092;
(Continued)

(56) References Cited

U.S. PATENT DOCUMENTS

| 4,948,587 A | 8/1990 | Kost et al. |
| 5,011,471 A | 4/1991 | Miyazaki et al. |

(Continued)

FOREIGN PATENT DOCUMENTS

| CN | 2230169 | 7/1996 |
| CN | 1730109 A | 2/2006 |

(Continued)

OTHER PUBLICATIONS

Alex, P. et al., "Distinct cytokine patterns identified from multiplex profiles of murine DSS and TNBS-induced colitis," Inflammatory Bowel Diseases 15, 341-352 (2009).
(Continued)

*Primary Examiner* — Tiffany Legette
(74) *Attorney, Agent, or Firm* — Smith Baluch LLP

(57) ABSTRACT

Apparatus, kits, and methods for administering a substance are presented. A device for administering a substance includes an elongated body having a proximal end and a distal end, the elongated body defining an internal chamber extending between the proximal end and the distal end to direct the substance to the distal end, the distal end to connect with a tip, the tip to be at least partially inserted into an orifice of a body lumen of a subject, the tip having a shape configured to reduce leakage of the substance from the orifice upon the at least partial insertion. The tip includes an opening to pass the substance from the internal chamber into the body lumen; and a transducer to emit an ultrasound wave from the tip into the body lumen, thereby administering the substance to tissue in the body lumen.

35 Claims, 46 Drawing Sheets

Related U.S. Application Data

(60) Provisional application No. 62/144,842, filed on Apr. 8, 2015.

(52) U.S. Cl.
CPC .......... *A61M 3/0279* (2013.01); *A61M 31/00* (2013.01); *A61M 37/0092* (2013.01); *A61M 3/022* (2014.02); *A61M 3/0208* (2014.02); *A61M 2205/0238* (2013.01); *A61M 2205/0294* (2013.01); *A61M 2205/058* (2013.01); *A61M 2205/123* (2013.01); *A61M 2205/3368* (2013.01); *A61M 2205/586* (2013.01); *A61M 2210/1067* (2013.01); *A61M 2250/00* (2013.01)

(58) Field of Classification Search
CPC .......... A61M 2205/058; A61M 3/0208; A61M 3/022; A61M 31/00; A61M 2205/0238; A61M 2205/0294; A61M 2205/123; A61M 2205/3368; A61M 2205/586; A61M 3/000208; A61M 2210/1067; A61M 2250/50; A51N 7/00; A61B 8/00; A61B 8/4422
See application file for complete search history.

(56) References Cited

U.S. PATENT DOCUMENTS

| | | | |
|---|---|---|---|
| 5,562,608 A * | 10/1996 | Sekins .............. | A61M 16/0486 604/20 |
| 5,628,730 A | 5/1997 | Shapland et al. | |
| 6,135,771 A | 10/2000 | Dragan et al. | |
| 6,241,703 B1 | 6/2001 | Levin et al. | |
| 6,322,532 B1 | 11/2001 | D'Sa et al. | |
| 6,511,428 B1 * | 1/2003 | Azuma .................. | A61N 7/022 600/439 |
| 6,589,173 B1 * | 7/2003 | Mitragotri ................ | A61B 8/00 600/437 |
| 6,623,444 B2 | 9/2003 | Babaev | |
| 2004/0127891 A1 * | 7/2004 | Humble ............. | A61B 1/00142 606/1 |
| 2005/0033265 A1 | 2/2005 | Engel et al. | |
| 2005/0240147 A1 * | 10/2005 | Makower ....... | A61B 17/320725 604/96.01 |
| 2006/0100653 A1 * | 5/2006 | Akahoshi ............ | A61F 9/00745 606/169 |
| 2007/0055179 A1 * | 3/2007 | Deem ............... | A61M 37/0092 601/2 |
| 2008/0119779 A1 * | 5/2008 | Babaev ............... | A61M 3/0275 604/22 |
| 2008/0200754 A1 * | 8/2008 | Buchalter .......... | A61B 1/00142 600/101 |
| 2011/0282251 A1 | 11/2011 | Baker et al. | |
| 2011/0282268 A1 * | 11/2011 | Baker .................. | A61M 15/08 604/20 |
| 2012/0219347 A1 * | 8/2012 | Law .................... | A61M 35/006 401/133 |
| 2012/0283605 A1 | 11/2012 | Lewis, Jr. | |
| 2014/0148734 A1 | 5/2014 | Hernandez et al. | |
| 2014/0228715 A1 | 8/2014 | Schroeder et al. | |
| 2014/0343483 A1 | 11/2014 | Zhang et al. | |
| 2014/0364799 A1 * | 12/2014 | Beauvais ............ | A61M 1/0086 604/28 |

FOREIGN PATENT DOCUMENTS

| | | | | |
|---|---|---|---|---|
| CN | 201253378 | | 6/2009 | |
| CN | 201275344 | | 7/2009 | |
| CN | 203303395 U | | 11/2013 | |
| CN | 103845771 A | | 6/2014 | |
| JP | 2001025467 A | | 1/2001 | |
| JP | 2002519095 A | | 7/2002 | |
| JP | 2010509944 A | | 4/2010 | |
| WO | WO 99/060012 A1 | | 11/1999 | |
| WO | 0000095 A1 | | 1/2000 | |
| WO | WO 02/055131 A2 | | 7/2002 | |
| WO | 2008042669 | | 1/2009 | |
| WO | WO 2009/153973 A1 | | 12/2009 | |
| WO | WO-2009153973 A1 * | | 12/2009 | .......... A61M 3/0283 |
| WO | WO 2013/155156 A1 | | 10/2013 | |

OTHER PUBLICATIONS

Barr, W. H. et al., "Intestinal drug absorption and metabolism I: Comparison of methods and models to study physiological factors of in vitro and in vivo intestinal absorption," Journal of Pharmaceutical Sciences 59, 154-163 (1970).

Bawiec, C. R. et al., "Finite element static displacement optimization of 20-100 kHz flexural transducers for fully portable ultrasound applicator," Ultrasonics 53, 511-517 (2012).

Brotchie, A. et al., "Characterization of Acoustic Cavitation Bubbles in Different Sound Fields," J. Phys. Chem. B 114, 11010-11016 (2010).

Capurso, N. A. et al., "Development of a pH-Responsive Particulate Drug Delivery Vehicle for Localized Biologic Therapy in Inflammatory Bowel Disease," The Yale Journal of Biology and Medicine 84, 285-288 (2011).

Cerutti, A., "Location, location, location: B-cell differentiation in the gut lamina propria," Mucosal Immunol 1, 8-10 (2008).

Ciarleglio, C. A. et al., "Rowasa Suspension Enema (Mesalamine, USP)," Gastroenterology Nursing, 122-124 (1989).

Coleman, A. J. et al., "Acoustic performance and clinical use of a fibreoptic hydrophone," Ultrasound in Medicine & Biology 24, 143-151 (1998).

Cooper, H. S. et al., "Clinicopathologic study of dextran sulfate sodium experimental murine colitis," Lab Invest 69, 238-249 (1993).

Danese, S. et al., "Ulcerative Colitis," N Engl J Med 365, 1713-1725 (2011).

Dechadilok, P. et al., "Hindrance factors for diffusion and convection in pores," Industrial & Engineering Chemistry Research 45, 6953-6959 (2006).

Ensign, L. M. et al., "Oral drug delivery with polymeric nanoparticles: The gastrointestinal mucus barriers," Advanced Drug Delivery Reviews 64, 557-570 (2012).

Frieri, G. et al., "Mucosal 5-aminosalicylic acid concentration inversely correlates with severity of colonic inflammation in patients with ulcerative colitis," Gut 47, 410-414 (2000).

Holland, C. K., "Thresholds for transient cavitation produced by pulsed ultrasound in a controlled nuclei environment," J. Acoust. Soc. Am. 88, 2059-2069 (1990).

Horowitz, S. B. et al., "The Nuclear Permeability, Intracellular Distribution, and Diffusion of Inulin in the Amphibian Oocyte," The Journal of Cell Biology 60, 405-415 (1974).

International Search Report and Written Opinion dated Aug. 1, 2016 for International Application No. PCT/US2016/026779, 15 pages.

Karaca-Mandic, P. et al., "Impact of New Drugs and Biologics on Colorectal Cancer Treatment and Costs," Journal of Oncology Practice 7, e30s-e37s (2011).

Kedia, P. et al., "Once-daily MMX mesalamine for the treatment of mild-to-moderate ulcerative colitis," Therapeutics and Clinical Risk Management 3, 919-927 (2007).

Kennedy, J. E., "Innovation: High-intensity focused ultrasound in the treatment of solid tumours," Nat Rev Cancer 5, 321-327 (2005).

Li, T. et al., "Passive Cavitation Detection during Pulsed HIFU Exposures of Ex Vivo Tissues and In Vivo Mouse Pancreatic Tumors," Ultrasound in Medicine & Biology 40, 1523-1534 (2014).

Lin, H.-Y. et al., "Factors Affecting Responsivity of Unilamellar Liposomes to 20 kHz Ultrasound," Langmuir 20, 6100-6106 (2004).

Lin, H.-Y. et al., "PEG-Lipids and Oligo(ethylene glycol) Surfactants Enhance the Ultrasonic Permeabilizability of Liposomes," Langmuir 19, 1098-1105 (2003).

Liu, J. et al., "Non-invasive assessment and control of ultrasound-mediated membrane permeabilization," Pharm Res 15, 918-924 (1998).

(56) References Cited

OTHER PUBLICATIONS

Malkov, V. A. et al., "Multiplexed measurements of gene signatures in different analytes using the Nanostring nCounter™ Assay System," BMC Res Notes 2:80, 9 pages (2009).

Marshall, J. K. et al., "Putting rectal 5-aminosalicylic acid in its place: The role in distal ulcerative colitis," American Journal of Gastroenterology 95, 1628-1636 (2000).

Morrow, M. P. et al., "DNA Drugs Come of Age," Scientific American 303, 48-53 (2010).

Naganuma, M. et al., "Measurement of Colonic Mucosal Concentrations of 5-Aminosalicylic Acid Is Useful for Estimating Its Therapeutic Efficacy in Distal Ulcerative Colitis: Comparison of Orally Administered Mesalamine and Sulfasalazine," Inflammatory Bowel Diseases 7, 221-225 (2001).

Nakashima, T. et al., "Rebamipide Enema is Effective for Treatment of Experimental Dextran Sulfate Sodium Induced Colitis in Rats," Dig Dis Sci 50, S124-S131 (2005).

Neurath, M. F., "Cytokines in inflammatory bowel disease," Nature Reviews Immunology 14, 329-342 (2014).

Neurath, M. F., "New targets for mucosal healing and therapy in inflammatory bowel diseases," Mucosal Immunol 7, 6-19 (Jan. 2014).

Pavlin, C. J. et al., "Clinical Use of Ultrasound Biomicroscopy," Ophthalmology 98, 287-295 (1991).

Peck, K. D. et al., "Hindered Diffusion of Polar Molecules Through and Effective Pore Radii Estimates of Intact and Ethanol Treated Human Epidermal Membrane," Pharm Res 11, 1306-1314 (1994).

Pecot, C. V. et al., "RNA interference in the clinic: challenges and future directions," Nat Rev Cancer 11, 59-67 (2011).

Pelekasis, N. A. et al., "Secondary Bjerknes forces between two bubbles and the phenomenon of acoustic streamers," J. Fluid Mech. 500, 313-347 (1999).

Polat, B. E. et al., "Ultrasound-mediated transdermal drug delivery: Mechanisms, scope, and emerging trends," Journal of Controlled Release, vol. 152, No. 3, pp. 330-348, (Jun. 2011).

Prentice, P. et al., "Membrane disruption by optically controlled microbubble cavitation," Nat Phys, vol. 1, No. 2, pp. 107-110, (Oct. 2005).

Sann, H. et al., "Efficacy of drugs used in the treatment of IBD and combinations thereof in acute DSS-induced colitis in mice," Life Sciences 92, 708-718 (2013).

Schoellhammer, C. M. et al., "Skin permeabilization for transdermal drug delivery: recent advances and future prospects," Expert Opin. Drug Deliv, vol. 11, No. 3, pp. 393-407, (Jan. 2014).

Schultz, S. G. et al., "Determination of the Effective Hydrodynamic Radii of Small Molecules by Viscometry," The Journal of General Physiology 44, 1189-1199 (1961).

Seibold, F. et al., "Topical therapy is underused in patients with ulcerative colitis," Journal of Crohn's and Colitis 8, 56-63 (2014).

Seto, J. E. et al., "Effects of ultrasound and sodium lauryl sulfate on the transdermal delivery of hydrophilic permeants: Comparative in vitro studies with full-thickness and split-thickness pig and human skin," Journal of Controlled Release 145, 26-32 (2010).

Škalko-Basnet, N., "Biologics: the role of delivery systems in improved therapy," Biologics : Targets & Therapy 8, 107-114 (2014).

Tezel, A. et al., "Description of transdermal transport of hydrophilic solutes during low-frequency sonophoresis based on a modified porous pathway model," Journal of Pharmaceutical Sciences 92, 381-393 (2003).

Veereman, G., "Pediatric Applications of Inulin and Oligofructose," The Journal of Nutrition 137, 2585S-2589S (2007).

Vong, L. B. et al., "An Orally Administered Redox Nanoparticle That Accumulates in the Colonic Mucosa and Reduces Colitis in Mice," Gastroenterology 143, 1027-1036 (2012).

Wirtz, S. et al., "Chemically induced mouse models of intestinal inflammation," Nature Protocols, vol. 2, pp. 541-546 (2007).

Wolf, J. M. et al., "Inflammatory bowel disease: sorting out the treatment options," Cleveland Clinic Journal of Medicine 69, 621-626 (2002).

Wolloch, L. et al., "The importance of microjet vs shock wave formation in sonophoresis," Journal of Controlled Release, vol. 148, No. 2, pp. 204-211 (2010).

Zhu, Q. et al., "Large intestine-targeted, nanoparticle-releasing oral vaccine to control genitorectal viral infection," Nature Medicine 18, 1291-1296 (2012).

Chinese Office Action and English Translation thereof in Chinese Patent Application No. 201680033312 dated Mar. 4, 2020, 29 pages.

Japanese Office Action and English Translation thereof in Japanese Patent Application No. 2018-504079 dated Feb. 13, 2020, 7 pages.

Chinese Office Action and English Translation thereof in Chinese Patent Application No. 201680033312 dated Sep. 27, 2020, 37 pages.

\* cited by examiner

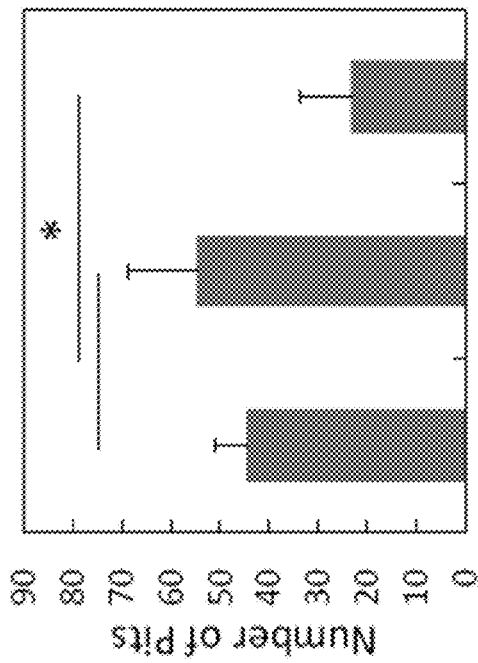
FIG. 9A
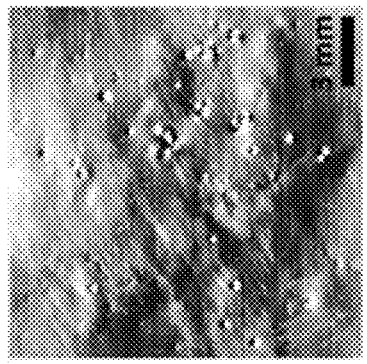
FIG. 9D (60 kHz)
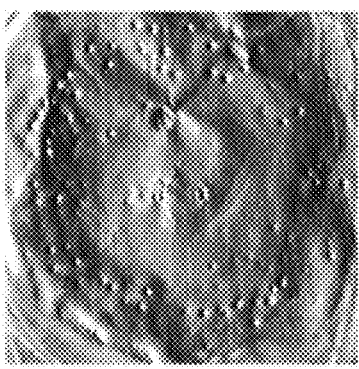
FIG. 9C (40 kHz)
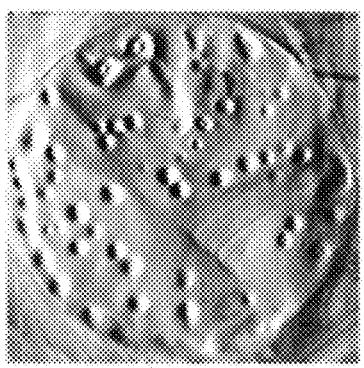
FIG. 9B (20 kHz)

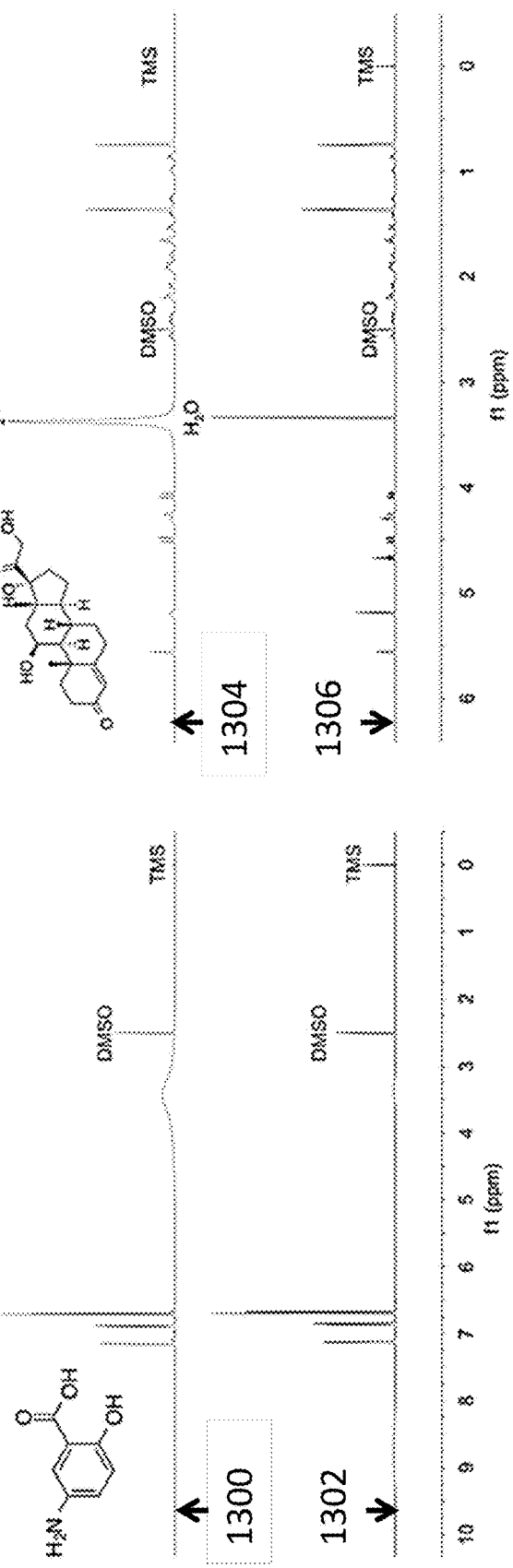
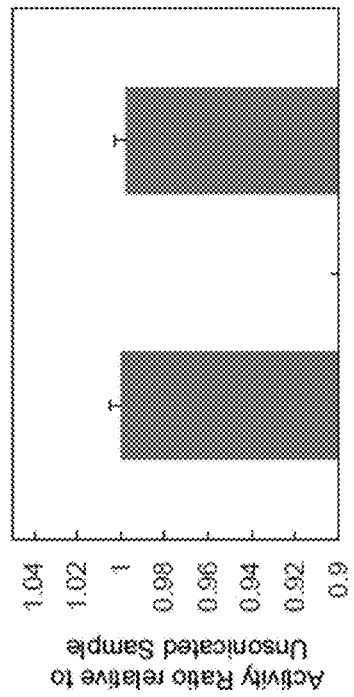
FIG. 13A
FIG. 13B
FIG. 13C

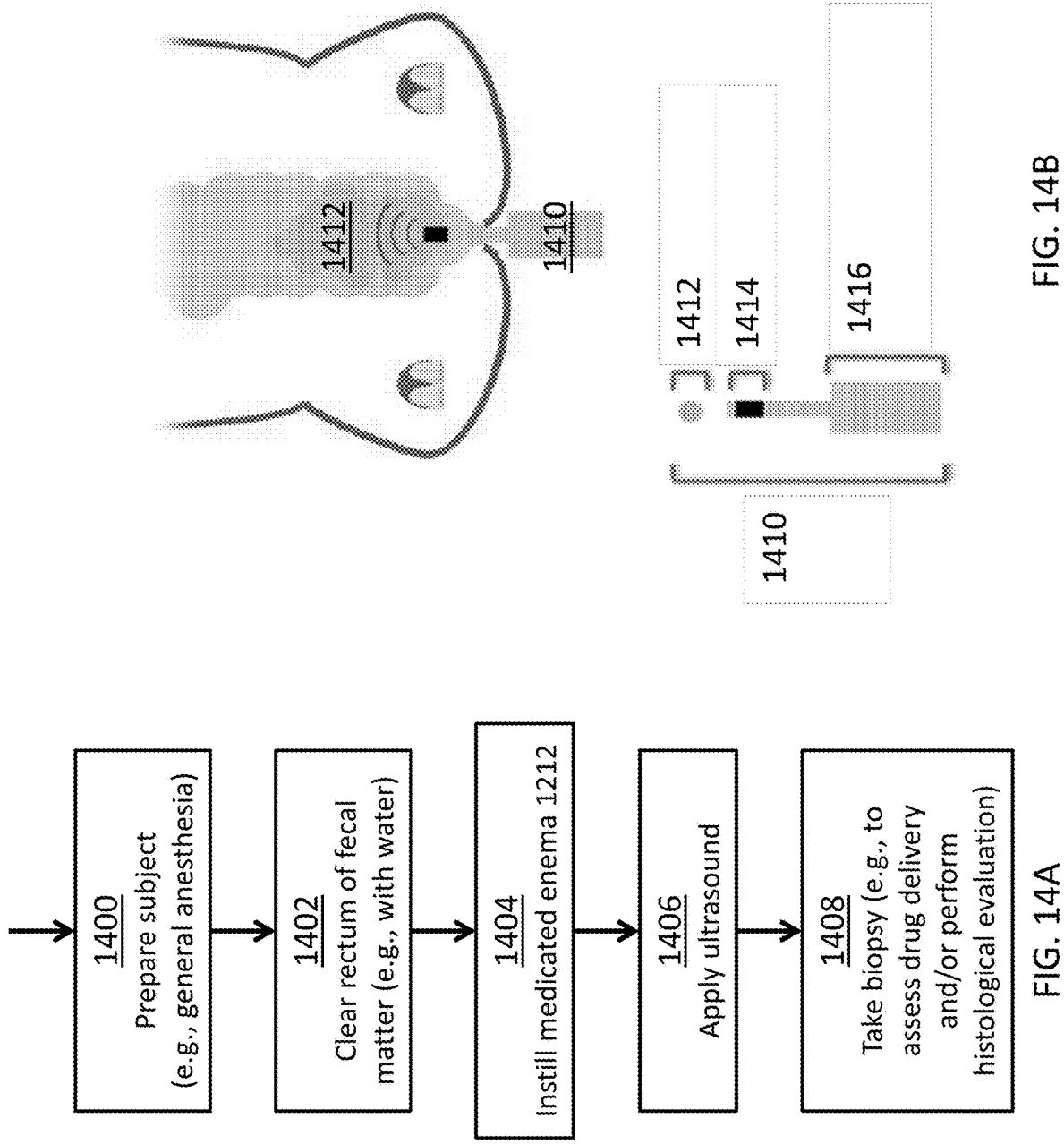

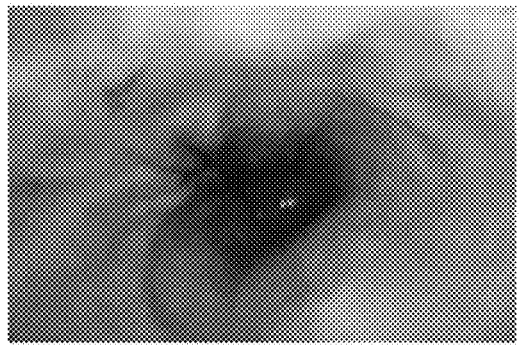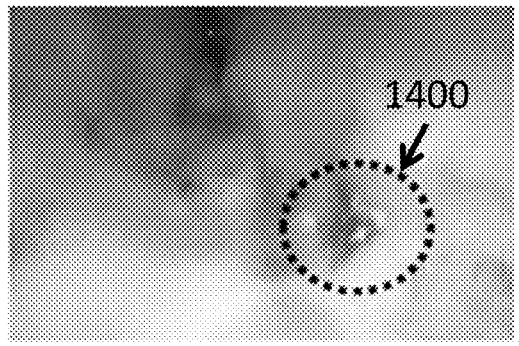
FIG. 15A  FIG. 15B
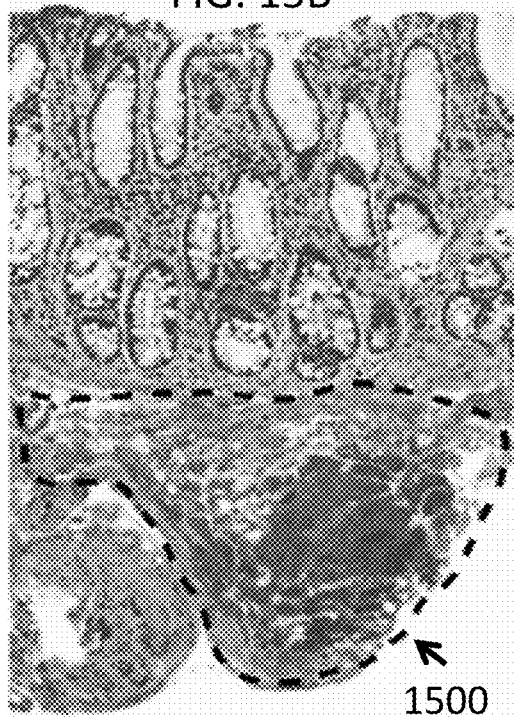
Control  Treated
FIG. 15C  FIG. 15D

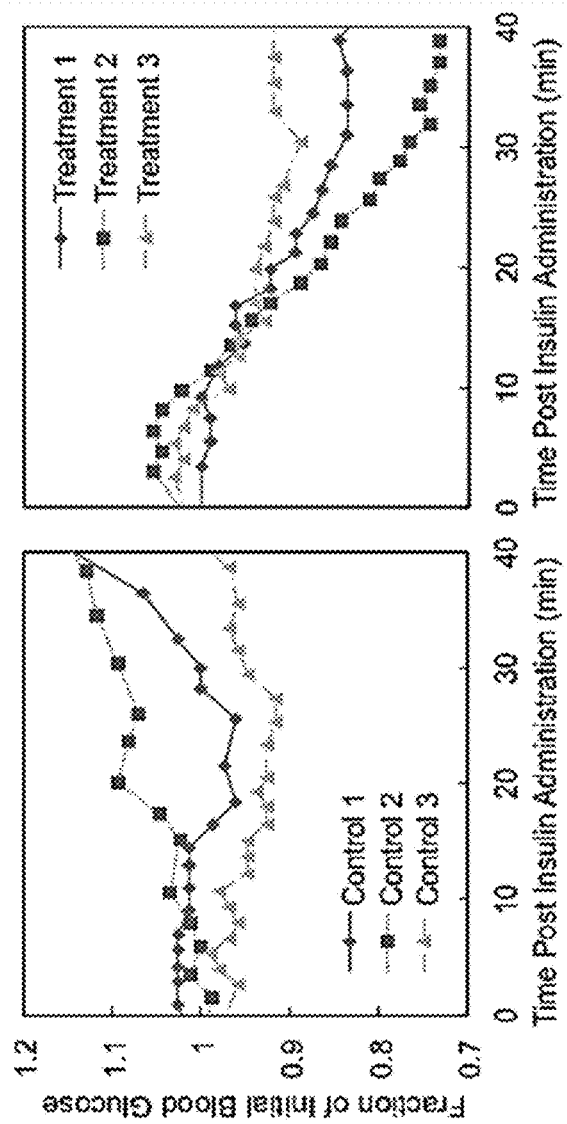
FIG. 17A
FIG. 17B
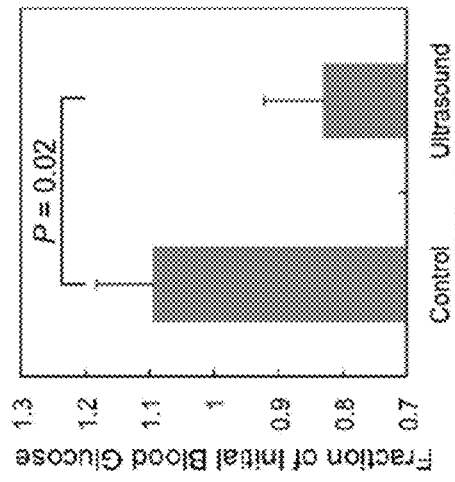
FIG. 17C

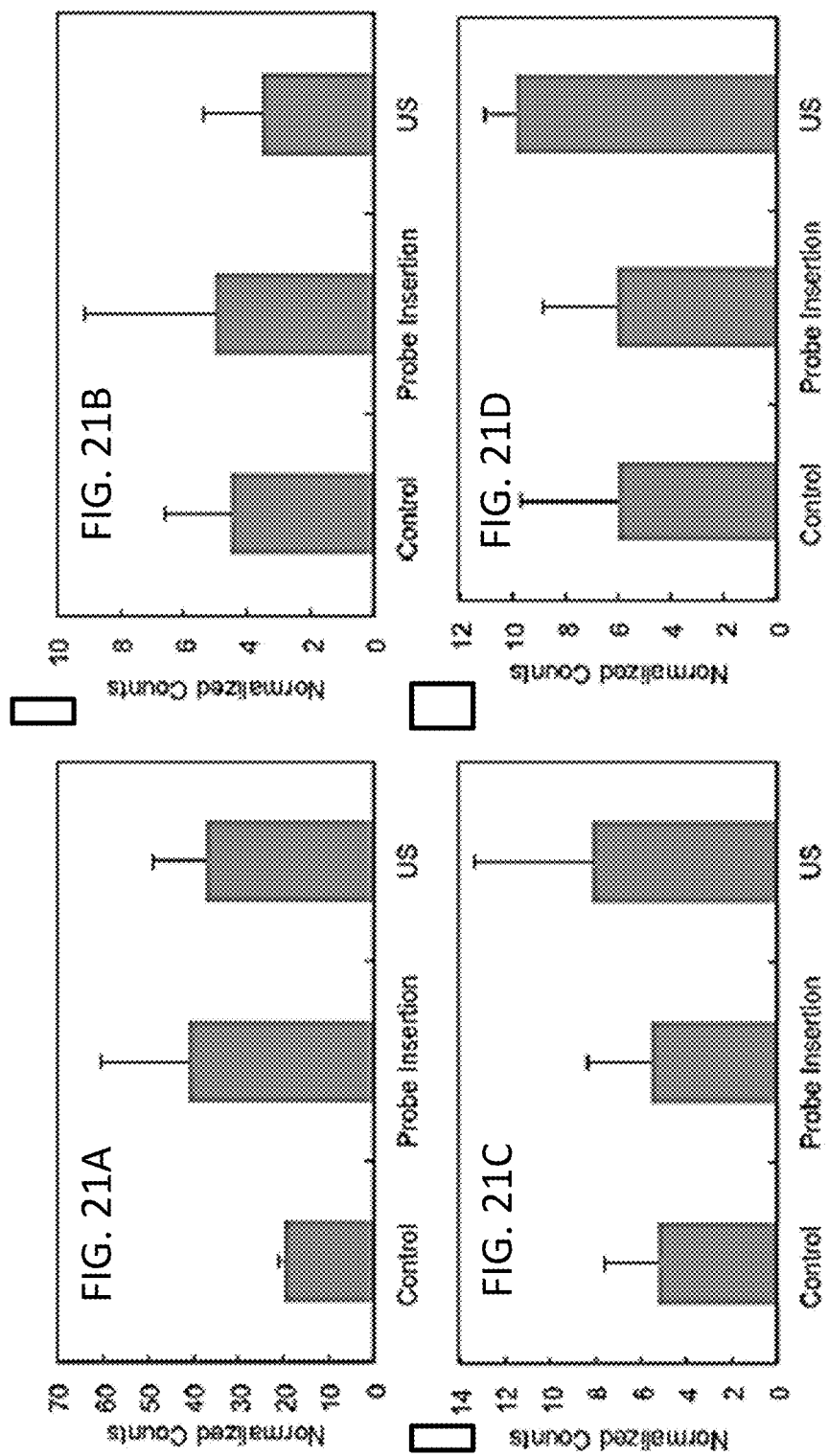

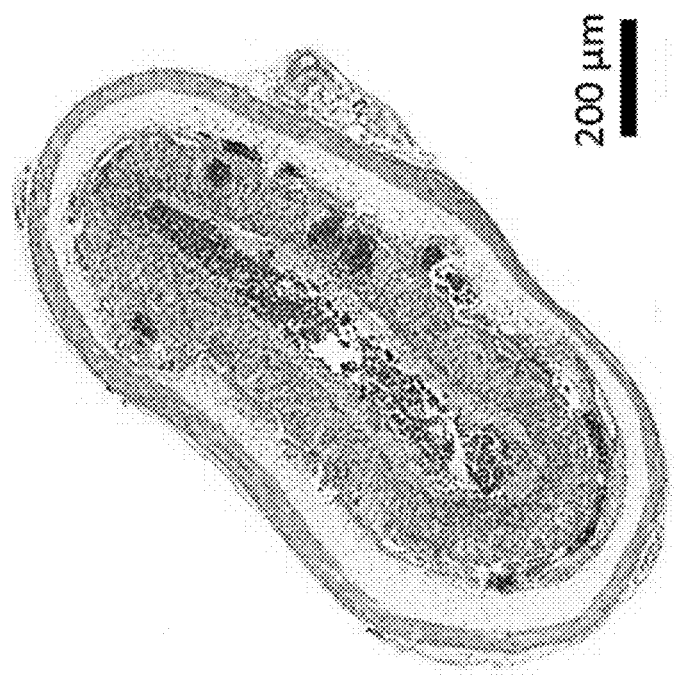
FIG. 25B
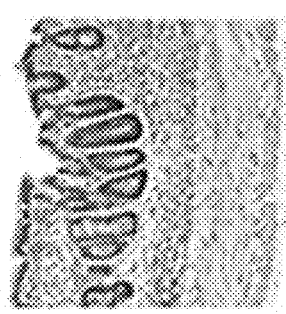
FIG. 25C
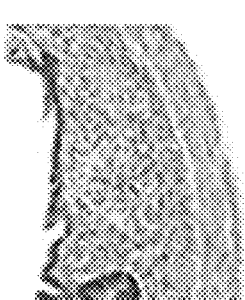
FIG. 25D
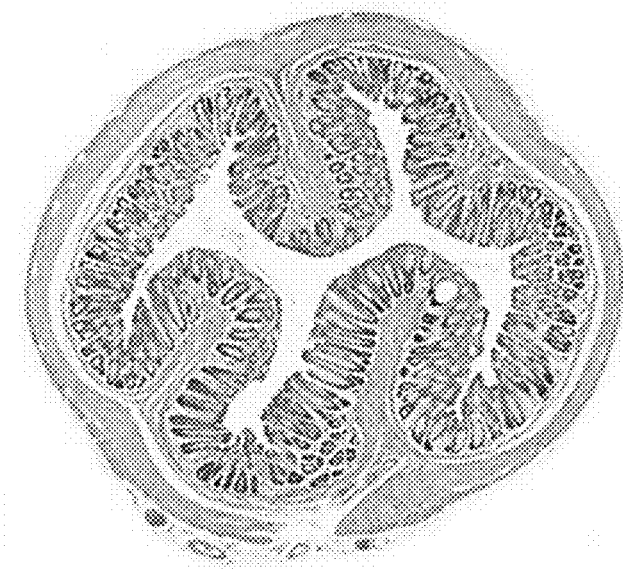
Healthy Tissue (Score 0)
FIG. 25A

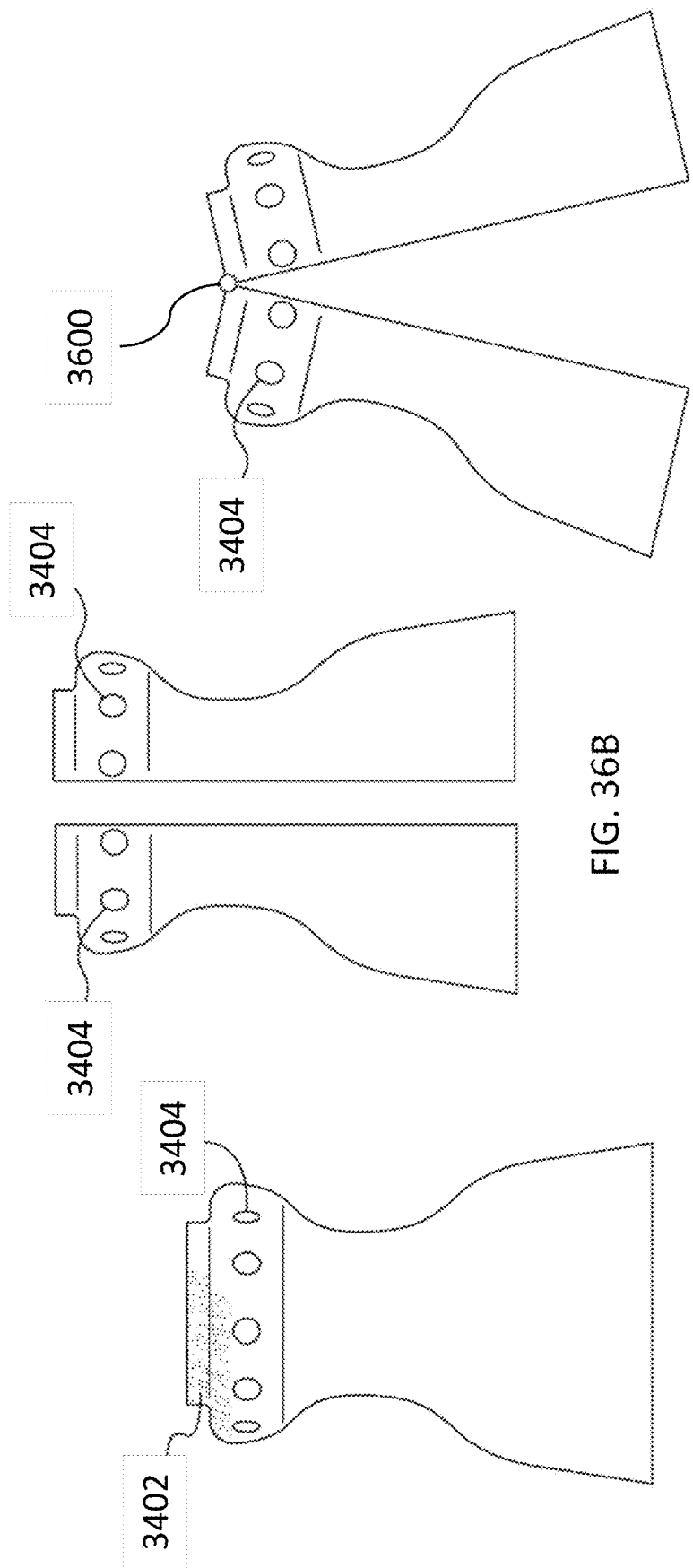

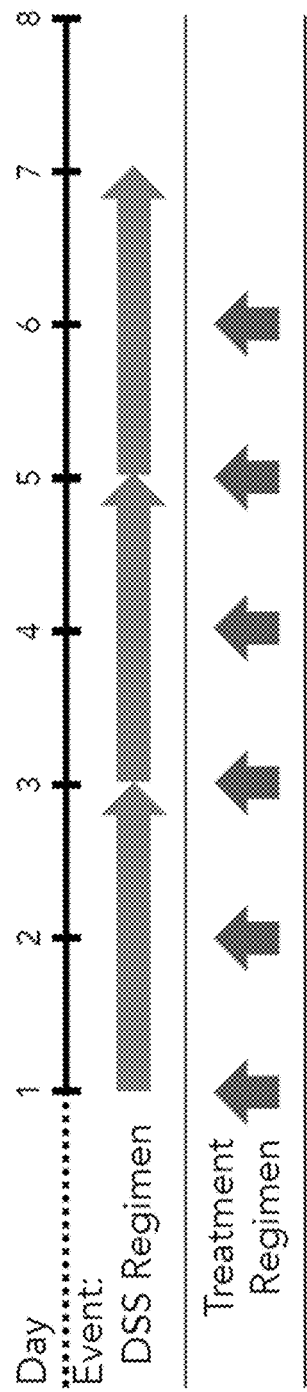
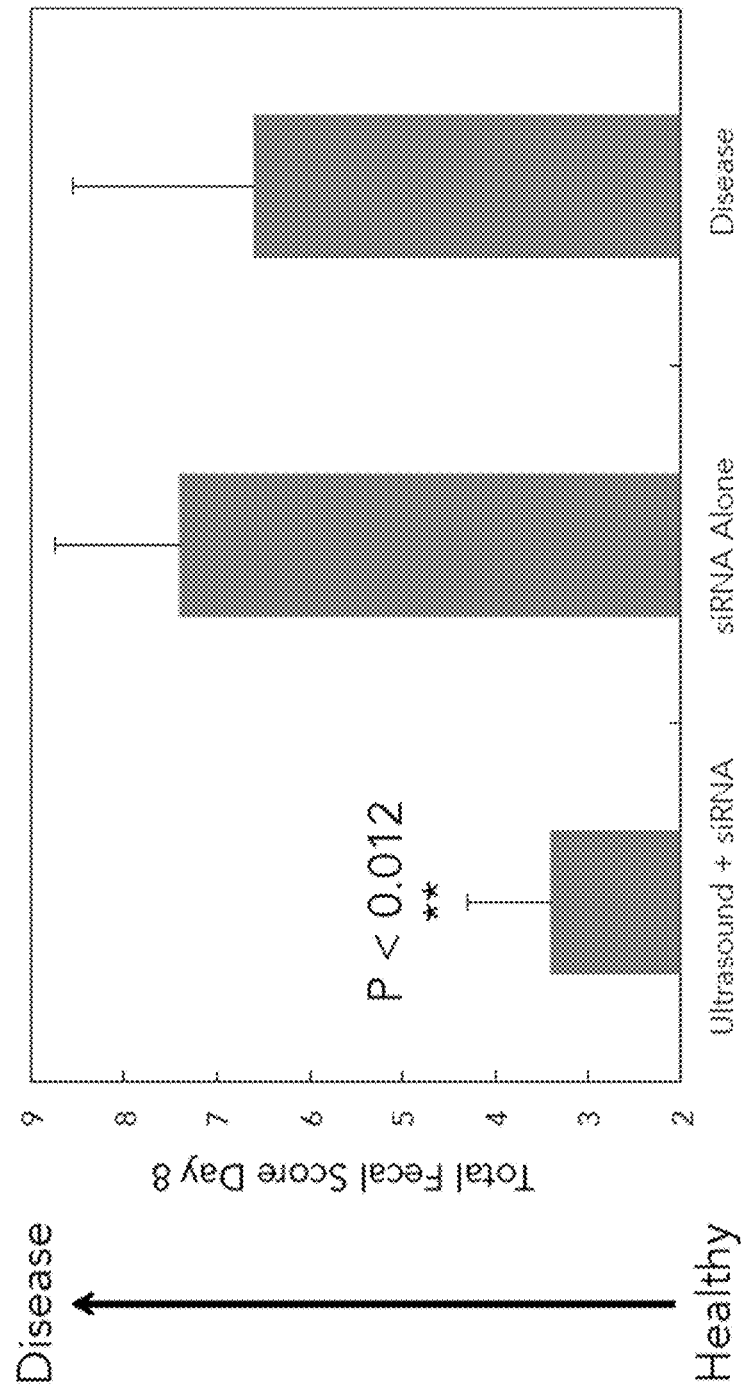
FIG. 38A
FIG. 38B

Healthy Tissue (Score 0)    Disease (Score 4)

SYSTEMS, APPARATUS, AND METHODS FOR ADMINISTERING A SUBSTANCE

CROSS-REFERENCE TO RELATED APPLICATIONS

This application is a continuation application of International Patent Application No. PCT/US2016/026779, filed Apr. 8, 2016, which claims a priority benefit of U.S. Provisional Patent Application No. 62/144,842, filed on Apr. 8, 2015, and entitled "Systems, Apparatus, and Methods for Administering a Substance," which applications are incorporated herein by reference in their entireties.

TECHNICAL FIELD

The present disclosure relates generally to systems, apparatus, and methods for delivering a substance to a subject. More specifically, the present disclosure relates to systems, apparatus, and methods for ultrasound-mediated gastrointestinal drug delivery.

BACKGROUND

The delivery of macromolecules across the gastrointestinal (GI) tract is one of the most highly investigated areas of research in drug delivery. Delivery via the GI tract, however, is still limited to small molecules. Even delivery of small molecules can be challenging, with most drugs often requiring specialized formulations to stabilize the active pharmaceutical ingredient and provide optimal absorption in the GI tract. No technology exists to facilitate rapid GI drug delivery.

SUMMARY

A platform that could allow for the delivery of a broad range of therapeutics without the need for time-consuming and costly reformulation could present a paradigm shift in delivery science and have wide clinical impact. Physical methods of drug delivery, such as ultrasound, may be capable of delivering macromolecules while circumventing the need for extensive formulation development. The present disclosure describes systems, apparatus, and methods for administering a substance. In some embodiments, these systems and methods can be used for ultrasound-mediated administration of a substance into a body lumen, such as the rectum.

In one embodiment, a device for administering a substance includes an elongated body having a proximal end and a distal end, the elongated body defining an internal chamber extending between the proximal end and the distal end to direct the substance to the distal end, the distal end to connect with a tip, the tip to be at least partially inserted into an orifice of a body lumen of a subject, the tip having a shape configured to reduce leakage of the substance from the orifice upon the at least partial insertion, the tip including an opening to pass the substance from the internal chamber into the body lumen, and a transducer to emit an ultrasound wave from the tip into the body lumen, thereby administering the substance to tissue in the body lumen.

In another embodiment, a tip for a device for administering a substance, the tip to be at least partially inserted in a rectum of a subject, includes an opening to pass the substance from an internal chamber of the device into at least the rectum, the tip having a shape configured to reduce leakage of the substance from the rectum upon the at least partial insertion, and a transducer to emit an ultrasound wave from the tip into at least the rectum, thereby administering the substance to tissue in at least the rectum.

In another embodiment, a sheath for a device for administering a substance includes a cover to protect at least a portion of the device, including the tip, from direct contact with the rectum, the cover comprising a material to reduce attenuation of the ultrasound wave, the material being at least one of acoustically transparent and acoustically conducting, the cover defining a perforation for aligning with the opening. The sheath may include an elastic band around the cover opening configured to reduce exposure of the device to the rectum, an elastic wrap configured to reduce exposure of the device to the rectum, a rigid piece for slipping over the tip, a first rigid piece and a second rigid piece to install from opposite sides of the tip such that the first rigid piece connects to the second rigid piece, and/or a first rigid piece joined by a hinge at the end of the tip to a second rigid piece.

In another embodiment, a cartridge for a device for administering a substance includes a housing defining a reservoir comprising the substance, the cartridge to be inserted in the internal chamber to establish fluid communication with the device.

In another embodiment, a kit for use in administering a substance includes a device for administering a substance, the device including an elongated body having a proximal end and a distal end, the elongated body defining an internal chamber extending between the proximal end and the distal end to direct the substance to the distal end. The kit also includes a tip for connecting to the distal end, the tip to be at least partially inserted into an orifice of a body lumen of a subject, the tip having a shape configured to reduce leakage of the substance from the orifice upon the at least partial insertion, the tip including an opening to pass the substance from the internal chamber into the body lumen, and a transducer to emit an ultrasound wave from the tip into the body lumen. The kit further includes a cartridge to be inserted in the internal chamber to establish fluid communication with the device, the cartridge including a housing defining a reservoir comprising the substance.

In another embodiment, a method for assembling a device for administering a substance includes connecting a tip to the distal end, the tip to be at least partially inserted into an orifice of a body lumen of a subject, the tip having a shape configured to reduce leakage of the substance from the orifice upon the at least partial insertion, the tip including an opening to pass the substance from the internal chamber into the body lumen and a transducer to emit an ultrasound wave from the tip into the body lumen. The method also includes inserting a cartridge in the internal chamber, the cartridge including a housing defining a reservoir comprising the substance to establish fluid communication with the device.

In another embodiment, a method for administering a substance includes inserting into an orifice of a body lumen of a subject at least a portion of a tip of a device, the tip having a shape configured to reduce leakage of the substance from the orifice upon the at least partial insertion; passing, via an opening in the tip, the substance into the body lumen; and simultaneously and/or subsequently emitting, via a transducer on the tip, an ultrasound wave into the body lumen, thereby administering the substance to tissue in the body lumen.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

Other systems, processes, and features will become apparent to those skilled in the art upon examination of the following drawings and detailed description. It is intended that all such additional systems, processes, and features be included within this description, be within the scope of the present invention, and be protected by the accompanying claims.

BRIEF DESCRIPTION OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

FIG. 9A is a graph and FIGS. 9B-9D are images illustrating transient cavitation in accordance with some embodiments.

FIGS. 13A and 13B are NMR spectra of substances before and after sonication, and FIG. 13C is a graph illustrating activity of a substance before and after sonication in accordance with some embodiments.

FIG. 14A is a flow diagram and FIG. 14B is a diagram illustrating a procedure for in vivo delivery in accordance with some embodiments.

FIGS. 15A and 15B are macroscopic images and FIGS. 15C and 15D are histological images illustrating effects of sonication on colonic tissue in accordance with some embodiments.

FIGS. 17A and 17B are plots of relative blood glucose, and FIG. 17C is a graph of relative blood glucose illustrating effects of sonication on insulin administration in accordance with some embodiments.

FIGS. 21A-21D are graphs illustrating effects of ultrasound on cytokine presentation in accordance with some embodiments.

FIGS. 25A-25E are images illustrating effects of ultrasound on histology in accordance with some embodiments.

FIGS. 36A-36C are schematics illustrating a rigid sheath for a handheld ultrasound-emitting drug delivery device in accordance with some embodiments.

FIG. 38A is a diagram illustrating a treatment regimen in accordance with some embodiments. FIG. 38B is bar graph illustrating effects of ultrasound for nucleic acid delivery on total fecal scores in accordance with some embodiments.

DETAILED DESCRIPTION

Figure 1:
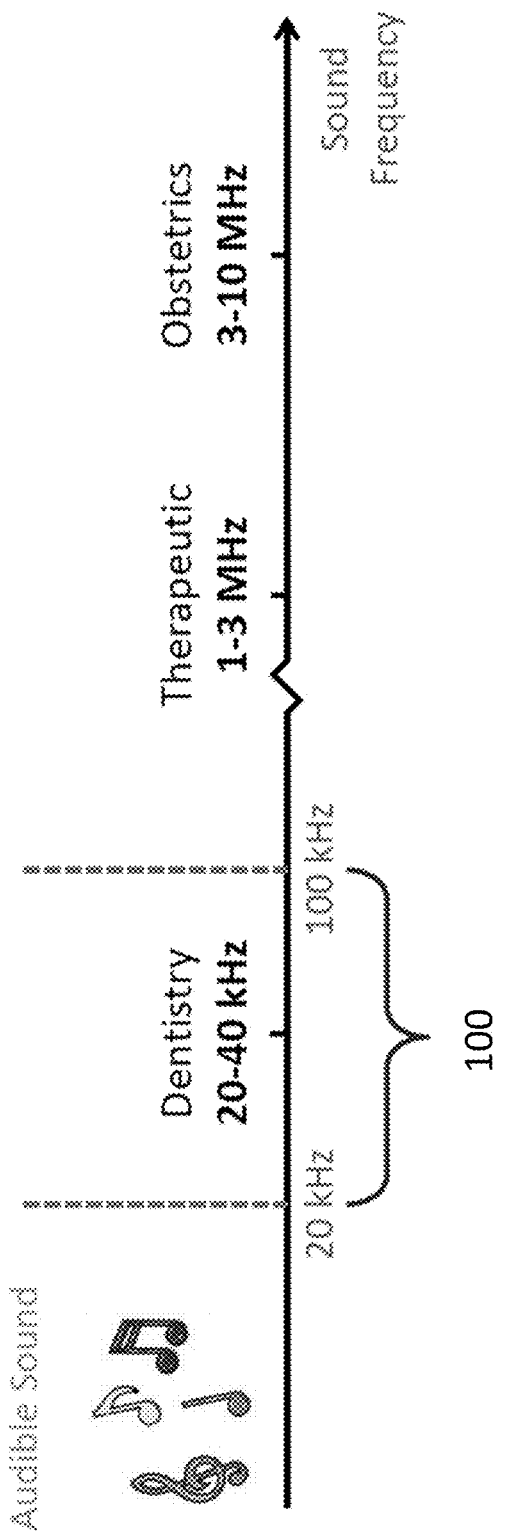
FIG. 1 is a chart illustrating ultrasound frequencies in accordance with some embodiments.

As shown in FIG. 1, ultrasound is a longitudinal pressure wave characterized by an amplitude and a frequency (above the audible range, e.g., greater than 20 kHz). Clinically, ultrasound is utilized in a variety of settings, including ultrasonography, tumor ablation, and lithotripsy. These obstetrics and therapeutic applications mainly utilize high-frequency ultrasound (e.g., greater than 1 MHz). At lower frequencies (e.g., range 100 from about 20 kHz to about 100 kHz in FIG. 1), however, ultrasound has unique properties including the ability to transiently permeabilize, and propel therapeutic substances into tissue by a phenomenon known as transient cavitation. Transient cavitation can be induced using a variety of ultrasound probe configurations, including axial and radial emission. Furthermore, the optimal ultrasound configuration could be adjusted depending on the condition being treated, maximizing the potential generalizability of this modality.

Using a physical delivery modality, such as ultrasound, to maximize drug delivery to the GI tract could have broad clinical utility. Inflammatory bowel disease represents one set of conditions that may be amenable to ultrasound assisted drug administration. This debilitating set of conditions is associated with high morbidity and a negative impact on quality-of-life. The most common subtype is ulcerative colitis. First line therapy for ulcerative colitis includes aminosalicylates administered via oral and/or rectal routes, with the latter being recognized as more efficacious, particularly with mild to moderate disease activity. However, rectal treatment (i.e., medicated enema) efficacy is directly dependent on retention time and tissue drug absorption, both of which are challenging for patients suffering from diarrhea and frequent bowel movements. Therefore, the use of ultrasound to maximize local mucosal concentrations of aminosalicylates in the rectum, while reducing the necessary retention time of the enema, may be one potential application of this technology with significant clinical impact and benefit for patients who must currently self-administer medicated enemas.

In addition to therapeutic delivery to the rectum locally, a physical delivery modality could also allow for the systemic delivery of a wide-range of compounds, shifting the way in which diseases are targeted and treated. This recognition suggests that the use of ultrasound as a physical delivery platform enables a significantly greater amount of drug to be delivered in all segments of the GI tract. For instance, ultrasound enables the delivery of model therapeutics across a broad range of molecular weights in all portions of the GI tract ex vivo. In some cases, this technology could be used via the rectum, for example, for the delivery of topical therapeutics currently used for the management of inflammatory bowel disease.

The current standard of care for inflammatory bowel disease is the self-administration of medicated enemas. As a result, the simultaneous application of an ultrasonic probe that also administers the medicated enema would not present a hurdle to adoption for these patients. Additionally, higher mucosal concentrations of these agents have previously been shown to correlate with decreased disease activity.

The preclinical use of ultrasound as an active drug delivery modality throughout the GI tract is demonstrated in the present application. As shown herein, ultrasound was able to effectively enhance the delivery of model compounds with a wide range of molecular weights in all parts of the GI tract ex vivo. More surprisingly was the relatively short treatment time required for this (one minute of total ultrasound exposure). Investigation into the method of enhancement eliminated the possibility of acoustic streaming or thermal effects accounting for the enhancement in drug delivery observed and suggests that transient cavitation provides a significant contribution to the delivery enhancement. Indeed, thermal effects and sonication with 1 MHz ultrasound were both found to elicit no enhancement in delivery. Additionally, the temperature rise in vivo as a result of treatment was found to be only 1.04±0.66° C. Further, the generation of pits on aluminum foil samples as a result of sonication with 20, 40, or 60 kHz ultrasound supports the occurrence of transient cavitation at the intensities tested here. The effect of 20 kHz ultrasound on theoretical pore sizes generated in the tissue were also quantified and found to increase significantly as a result of ultrasound treatment. Even further enhancement in delivery could be achieved with additional investigation into the treatment regimen and device implementation.

Based on this current understanding and optimization of ultrasound-mediated gastrointestinal delivery (UMGID) ex vivo, two configurations were tested in vivo: (1) axial and (2) radial ultrasound emission in the rectum. The ability to generate ultrasound in multiple configurations in small, portable form factors amenable to at-home self-administration supports the generalizability of UMGID and its tunability. This is paramount for broad clinical and research applicability. In the immediate use-case of rectal delivery for diseases such as inflammatory bowel disease where enemas are already established as the standard-of-care treatment, patients may utilize a small, hand-held device that emits ultrasound radially to achieve a high degree of circumferential tissue permeability, increasing drug delivery. Continued improvement in ultrasound miniaturization could allow for a variety of different operating formats to enable convenient ultrasound exposure to all parts of the GI tract, including ingestible ultrasound-emitting capsules to facilitate systemic delivery in a convenient manner.

Axial emission in swine was demonstrated to be safe based on histological examination of the tissue and clinical monitoring of the animal. Ultrasound was also shown to significantly enhance delivery of mesalamine by an orderof-magnitude. The fact that this level of delivery is achievable with only one-minute of ultrasound application is indicative of the potential power of UMGID. Further, the delivery of insulin as a model biologic highlights the ability of axial emission to achieve systemic delivery of larger molecules through the rectum and potentially through the varying segments of the GI tract. It should be noted that while insulin was chosen for experimental convenience, its successful delivery is illustrative of the ability to deliver biologics locally to the rectum while retaining their function. Local delivery of biologics has the potential to be useful in a variety of diseases. For ulcerative colitis, for example, the local delivery of monoclonal antibodies targeting TNF could be beneficial to downregulate proinflammatory processes. This technology in its present form could also be beneficial in the local delivery of chemotherapeutics and biologics in the rectum for the treatment of colorectal cancer. Indeed, current strategies to achieve local delivery of these agents largely rely on formulation techniques, which suffer from low loading efficiencies and lack broad applicability to deliver many drugs.

In addition to axial emission, radial emission was tested in a clinically relevant murine colitis model. The most efficacious treatment of mild to moderate colitis is rectal administration. However, active disease can make retention of the medication difficult. For example, the current procedure for the rectal administration of Rowasa® (mesalamine, 4 g, available from Meda Pharmaceuticals, Somerset, N.J.) for the treatment of inflammatory bowel disease requires patients to first empty their bowels. They are then instructed to lie on their left side. The patient then must insert an applicator tip into the rectum and gently infuse the drug. Patients are instructed to remain in this position for at least 30 minutes and to retain the enema overnight. This creates a precarious and uncomfortable experience that must be endured nightly. This is particularly challenging for patients with active colitis who are experiencing urgency with frequent bowel movements. Even when this regimen is strictly adhered to, disease relapse rates are high. To test whether UMGID had the capacity to promote rapid delivery of mesalamine and thereby enhance treatment efficacy, an ultrasound probe with radial emission was used for its ability to permeabilize a larger area of tissue. The use of a custom-designed ultrasound probe with a shaft diameter ≤3 mm is indicative of the ability to significantly miniaturize this technology. Ultrasound in combination with a medicated enema was found to significantly improve disease indices. The trend towards improved clinical outcome in the QOD group suggests that ultrasound treatment QOD may be useful in less severe cases of colitis and in patients with suboptimal adherence to medication. The superior disease outcomes, both clinically and histologically, of ultrasound treatment QD compared to the current standard-of-care is exciting and suggests that UMGID could enable remission to be achieved with shorter treatment regimens. Moreover, it provides a solution for accelerated drug delivery in clinical settings where rapid disease-associated GI transit time limits the absorption of therapeutics. As a result, this technology may eliminate the need for extended enema retention.

UMGID has many potential applications ranging from localized site-specific treatment with anti-inflammatories to the more broad delivery of macromolecules. With further work, this technology could be miniaturized to dimensions compatible with ingestion, allowing for ingestible ultrasound-emitting capsules for systemic delivery. Based on the studies described here, ultrasound technology has the potential to deliver substances such as nanoparticles, monoclonal antibodies, or vaccines to modulate mucosal immune responses. Additionally, ultrasound could potentially enable the delivery of new classes of therapeutics such as DNA and RNA-based therapeutics, where delivery requires overcoming several biological barriers. With further study, this technology could prove invaluable in both clinical and research settings, enabling improved therapies and expansion of research techniques applied to the GI tract as well as new medical devices to enable local rectal delivery and, eventually, oral administration using ingestible devices.

EXAMPLE 1: PROOF-OF-CONCEPT USE OF ULTRASOUND FOR DRUG DELIVERY EX VIVO

To understand whether ultrasound could safely permeabilize GI tissue to allow for enhanced drug delivery and to identify the optimal conditions for UMGID, an ex vivo platform was developed utilizing fresh porcine GI tissue mounted in Franz diffusion cells (see FIG. 1a). The focus was on the use of low-frequency (less than 100 kHz) ultrasound given prior data supporting increased cavitational activity at typical intensities compared to high-frequency (greater than 1 MHz) ultrasound at the same intensities.

A. Experimental Setup

Phosphate buffered saline (PBS), hydrocortisone, mesalamine, inulin from Dahlia Tubers (5,000 Da), and deuterated dimethyl sulfoxide (DMSO) were obtained from Sigma-Aldrich (Saint Louis, Mo.). Granular D-glucose was obtained from Mallinckrodt Chemicals (Phillipsburg, N.J.). Lysine-fixable 3 and 70 kDa dextrans labeled with Texas Red were purchased from Invitrogen (Carlsbad, Calif.). Other radiolabeled permeants were obtained from American Radiolabeled Chemicals, Inc. (St. Louis, Mo.) and included 3H-labeled glucose and hydrocortisone and 14C-labeled mesalamine and 5,000 Da inulin. Solutions of the four compounds at a concentration of 1 mg/mL were prepared with a radiolabel content ranging from about 0.001% to about 2.5% depending on the stock solution's radiolabel content.

The MIT Committee on Animal Care approved all animal-related research aspects of this study. All tissue was obtained from Research 87, Inc. (Boylston, Mass.). GI tissue (e.g., tongue, esophagus, stomach, intestine, and colon tissue) from Yorkshire pigs was procured within 20 minutes of animal euthanization and stored at about 4° C. Drug delivery testing took place within 6 hours of euthanization. Upon delivery, the fresh porcine tissue was washed with PBS and excess fat was carefully dissected away. With the exception of tongue tissue, the full thickness of the tissue was used for testing. The tissue was sectioned into approximately 2 cm-by-2 cm pieces and kept hydrated with PBS. The variability in thickness of tongue tissue prevented mounting of the entire thickness in the diffusion chambers. Instead, the top surface was isolated with an electric dermatome (Zimmer Orthopedic Surgical Products, Dover, Ohio) to a thickness of about 700 μm and then dissected into sections approximately 1 inch square.

Figures 2A, 2B:
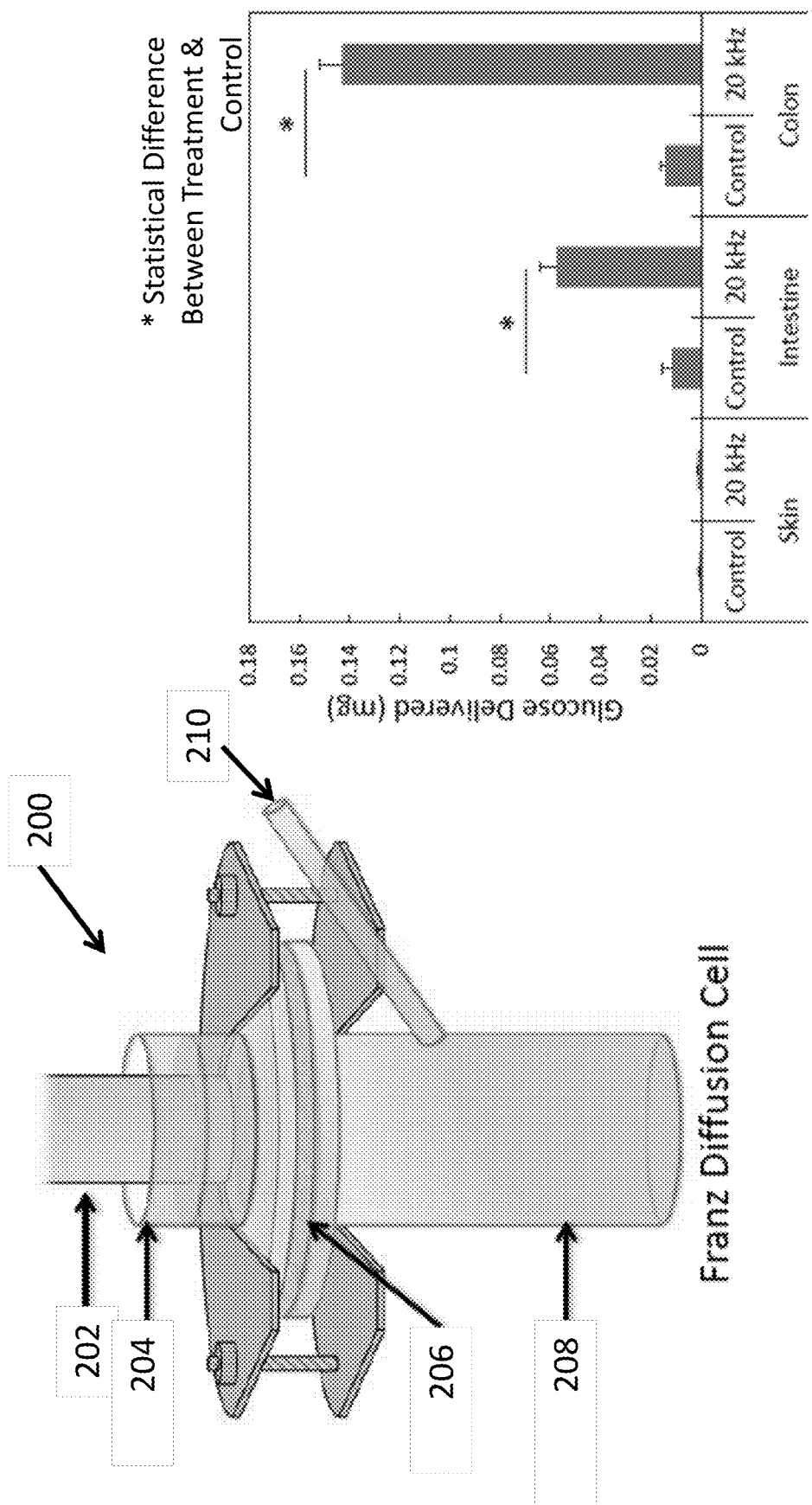
FIG. 2A is a diagram illustrating a Franz diffusion cell in accordance with some embodiments.
FIG. 2B is a graph illustrating ex vivo delivery of glucose to various tissue types in accordance with some embodiments.

Low-frequency (e.g., less than 100 kHz) ultrasound was utilized and administered directly to tissue and compared to controls consisting of untreated tissue. Delivery efficacy was assessed by quantifying the delivery of radiolabeled permeants into and through tissue utilizing Franz diffusion cells. FIG. 2A is a diagram illustrating a Franz diffusion cell 200 in accordance with some embodiments. Each Franz diffusion cell 200 includes an ultrasound emitting probe device 202, a donor chamber 204, a tissue sample 206, a receiver chamber 208, and a sampling port 210. Each receiver chamber 208 of multiple Franz diffusion cells 200 (15-mm-diameter, available from PermeGear, Hellertown, Pa.) was filled with PBS, and a section of fresh GI tissue 206 placed over each receiver chamber 208 with the luminal side up. Each diffusion cell 200 results in an exposed tissue area of about 1.77 $cm^2$. Unless otherwise noted, delivered quantities represent the total amount of permeant delivered over this area. For each diffusion cell 200, a donor chamber 204 was placed on top of the tissue 206, and the entire assembly was clamped tightly together to prevent leakage. Each donor chamber 204 was then filled with PBS to keep the tissue 206 hydrated before treatment. After all the required tissue was dissected and mounted in the Franz diffusion cells, the diffusion cells were randomly assigned to the various experimental groups.

Immediately prior to ultrasound treatment, the PBS solution in each donor chamber 204 was discarded and replaced with a donor solution, that is, a 1 mg/mL solution containing a radiolabeled compound of interest.

Ultrasonic frequencies of 20, 40, and 60 kHz were generated using three separate ultrasound generators, including the VCX 500, VCX 130, and a custom order probe, respectively (available from Sonics and Materials, Inc., Newtown, Conn.). Each probe or horn 202 had a 13-mm-diameter tip for providing axial emission of ultrasound. Three separate powers at each frequency were tested and each calibrated by calorimetry using an unlined dewar. Calorimetry was employed because this specific method is commonly used in the literature to estimate ultrasonic power. The three powers at 20 kHz were 2.5, 5, and 7.5 $W/cm^2$. At 40 kHz the three powers were 7.3, 10.5, and 13.4 $W/cm^2$. At 60 kHz, the three powers were 9.6, 11.5, and 12.4 $W/cm^2$. The difference in powers tested at each frequency were due to the sensitivities and efficiency of each ultrasound generator.

To apply ultrasound, the tip of the ultrasound probe or horn 202 was submerged in the permeant solution in each donor chamber 204 such that the tip was positioned about 3 mm away from the surface of the tissue 206. Regardless of frequency or power, the duration of treatment was two minutes using a 50% duty cycle (5s on, 5s off), resulting in one minute of ultrasound exposure.

Immediately after the ultrasound treatment, the donor solution was discarded and each donor chamber 204 was washed with PBS to remove any residual radiolabeled material not delivered into the tissue 206. The receiver solution was collected from each receiver chamber 208 through the sampling port 210 of the diffusion cell using a 15-mL transfer pipet (available from, e.g., VWR, Radnor, Pa.) and transferred to separate scintillation vials. The portion of each tissue exposed to the compound of interest was cut away and also placed in separate scintillation vials, with any remaining tissue being discarded. The number of repeats ranged from 3 to 10 for every treatment condition. In general, untreated tissue required more repeats (n=6). Esophagus also required more repeats due to the macroscopic non-uniformity of the tissue.

B. Quantification of Delivery Enhancement

Depending on the tissue type, either 5 mL (tongue and intestine) or 10 mL (all other tissue types) of the tissue solubilizer Soluene®-350 (available from Perkin Elmer, Waltham, Mass.) was added to the scintillation vials with exposed tissue to solubilize the tissue. Each tissue mixture was heated and allowed to sit until the tissue was completely dissolved. Regardless of the tissue, 5 mL of each tissue mixture was aliquoted into a second group of scintillation vials for radiometric analysis.

Each of the collected receiver solutions were thoroughly mixed and then a 0.5-mL sample was aliquoted into a second group of scintillation vials.

About 15 mL of Hionic-Fluor™ scintillation cocktail (available from Perkin Elmer, Waltham, Mass.) was then added to each of the receiver solution aliquot samples and the tissue aliquot samples and allowed to sit for about one hour for the signal to equilibrate. The samples were evaluated on a Tri-Carb® Liquid Scintillation Counter (available from Perkin Elmer, Waltham, Mass.).

First, the transport of tritiated glucose was evaluated as a model permeant comparing its delivery to all major segments of the GI tract. 20 kHz ultrasound was utilized and calibrated to an intensity of 7.5 $W/cm^2$. This intensity was selected based on calorimetry measurements demonstrating a negligible increase in the temperature of the coupling solution, thereby minimizing thermal effects. FIG. 2B is a graph illustrating an in vitro survey comparing the delivery of radiolabeled glucose in skin, intestine, and colon tissue with ultrasound (20 kHz) or without ultrasound (Control) according to some embodiments. The mass of glucose delivered to GI tissue was enhanced by as much as an order-of-magnitude when delivery was combined with one minute of ultrasound treatment (two-tailed Student's t-test, $P<0.03$).

To further understand the frequency and intensity dependencies and identify the optimal parameters of UMGID, glucose delivery was tested using three distinct frequencies, 20, 40, and 60 kHz at three separate intensities for each frequency in all tissue-types of the GI tract. Because transient cavitation was hypothesized to be the dominant mechanism, these frequencies were chosen to ensure the cavitation threshold could be exceeded.

Figure 3B:
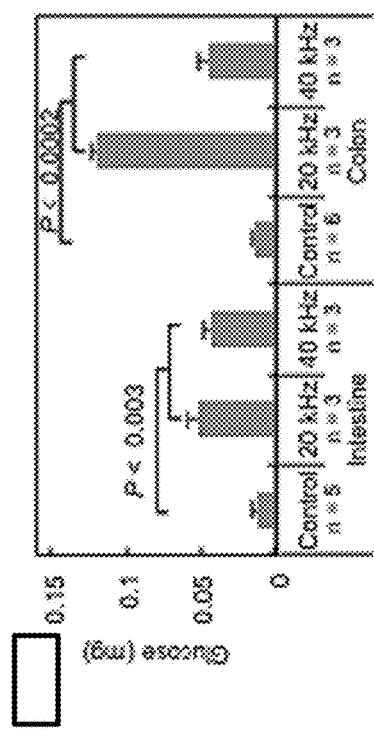
FIGS. 3A-3E are graphs illustrating ex vivo delivery of various substances to various tissue types in accordance with some embodiments.
Figure 3A:
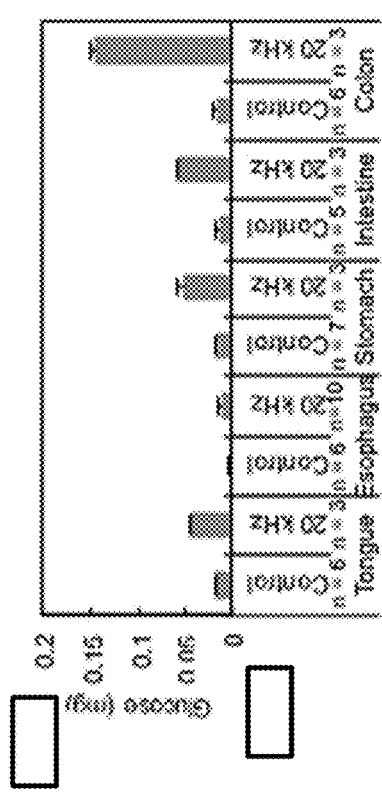

FIGS. 3A-3E are graphs illustrating in vitro surveys of the delivery of radiolabeled permeants at a concentration of 1 mg/mL in the donor chamber in different tissue types with treatment or without treatment (Control) in accordance with some embodiments. In FIG. 3A, the amount of glucose delivered to various tissues of the GI tract with ultrasound (20 kHz) and without ultrasound (Control) are compared. The treatment utilized a 20 kHz ultrasound horn calibrated calorimetrically to 7.5 $W/cm^2$. In FIG. 3B, the amount of glucose delivered to intestine and colon tissue is compared with the Control using 20 kHz and 40 kHz ultrasound at the lowest intensity considered for each frequency.

Figure 3C:
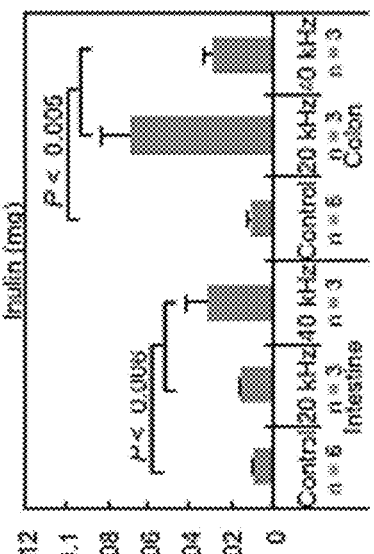

To assess the effect of analyte molecular weight and because glucose is actively absorbed across the GI tract by glucose transporters, this same survey was carried out using inulin (5,000 Da). Inulin was chosen for its lack of recognized active absorption via the GI epithelium. As a result of this test, delivery was found to be more greatly enhanced at frequencies of 20 and 40 kHz compared to 60 kHz. Delivery was relatively insensitive to the intensity at all frequencies. In FIG. 3C, the amount of 5,000 Da inulin delivered to intestine and colon tissue is compared with the Control using 20 kHz and 40 kHz ultrasound at the lowest intensity considered for each frequency.

Having shown that ultrasound can enhance delivery for all tissue types encountered in the GI tract ex vivo and identified optimal treatment conditions with this delivery modality, the delivery of topical therapeutics currently used for the management of inflammatory bowel disease utilizing 20 and 40 kHz axial emission was studied. Higher mucosal concentrations of these agents have previously been shown to correlate with decreased disease activity. Radiolabeled mesalamine (5-aminosalicylic acid) and hydrocortisone, both recognized topical treatments for inflammatory bowel disease, were evaluated with UMGID. Mesalamine was evaluated in the small and large intestine where it is used clinically. Hydrocortisone was evaluated throughout the GI tract in keeping with its broader clinical application. All treatment times were maintained at 1 minute of total ultrasound exposure, ensuring a practical treatment regimen compatible with the high-throughput nature of clinical endoscopy as well as patient self-administered enemas. Mesalamine delivery to the intestine was 14.97±5.10, 41.52±4.45, and 44.43±3.67 µg without ultrasound (control), and with 20 and 40 kHz, respectively. Delivery to the colon was 18.40±2.73, 73.70±8.39, and 47.37±3.05 µg for the control, 20, and 40 kHz, respectively. Hydrocortisone delivery was enhanced 2-5 fold throughout the GI tract also using 20 and 40 kHz ultrasound.

Figure 3E:
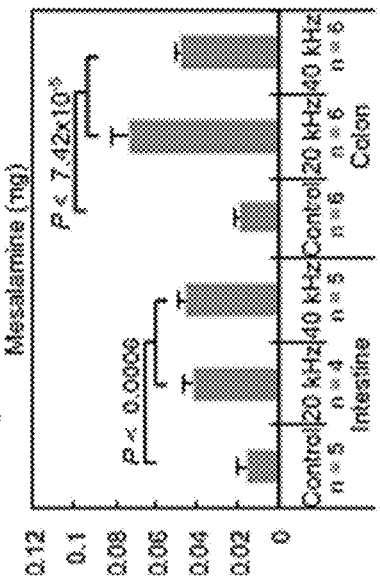
Figure 3D:
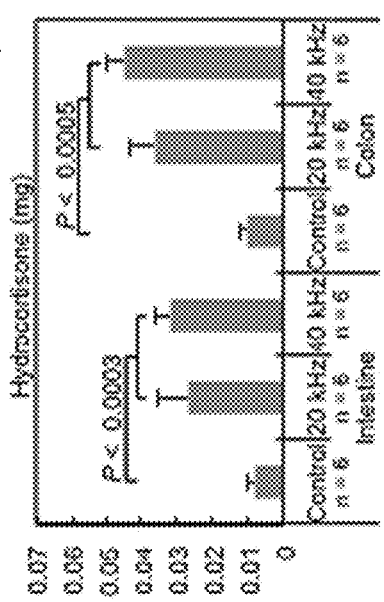
Figures 4A, 4B:
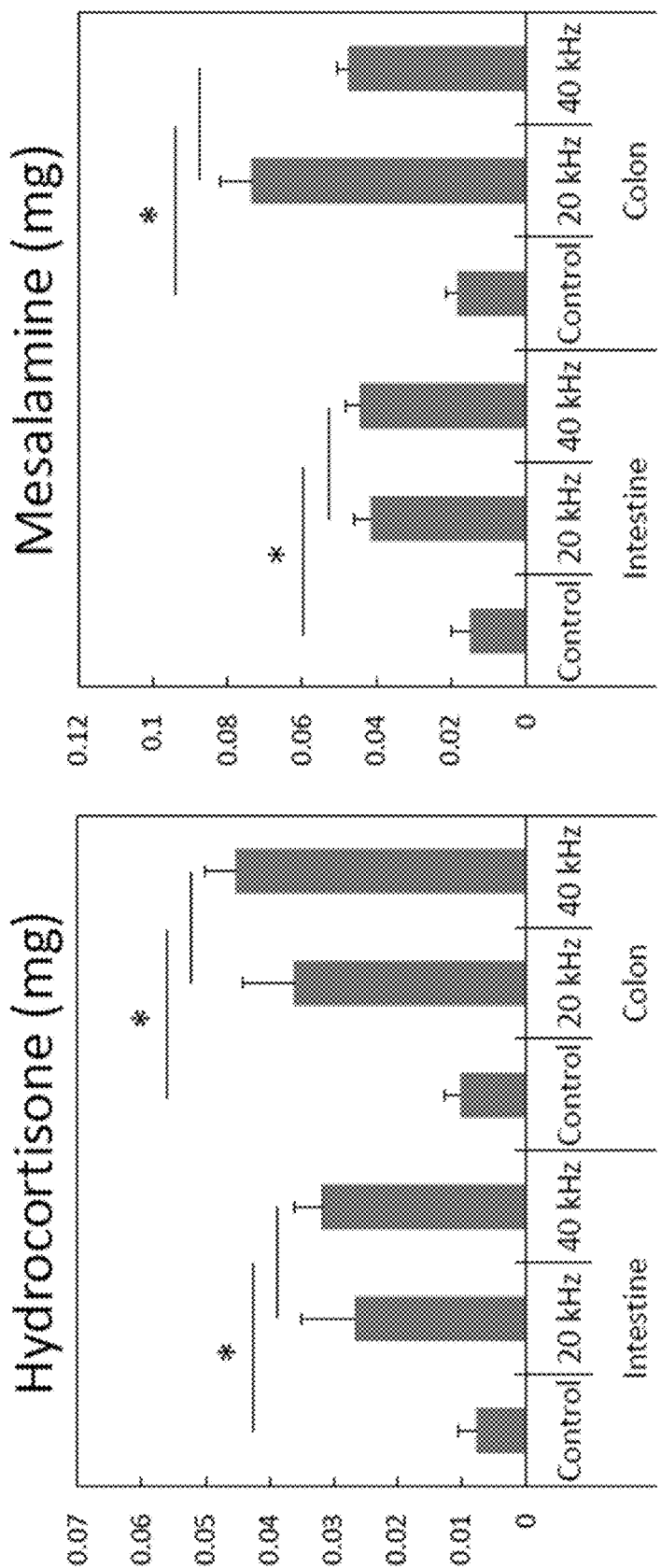
FIGS. 4A and 4B are graphs illustrating ex vivo delivery of various substances to various tissue types in accordance with some embodiments.

In FIG. 3D, the amount of the clinically relevant compound hydrocortisone delivered to intestine and colon tissue is compared with the Control using 20 kHz and 40 kHz ultrasound at the lowest intensity considered for each frequency. In FIG. 3E, the amount of the clinically relevant compound mesalamine delivered to intestine and colon tissue is compared with the Control using 20 kHz and 40 kHz ultrasound at the lowest intensity considered for each frequency. The graphs in FIGS. 4A-4B also illustrate these in vitro surveys comparing the delivery of radiolabeled hydrocortisone and mesalamine, respectively, in intestine and colon tissue with ultrasound (20 kHz or 40 kHZ) or without ultrasound (Control) according to some embodiments. As these graphs show, ultrasound significantly enhances the delivery of hydrocortisone and mesalamine to tissue.

Figure 5A:
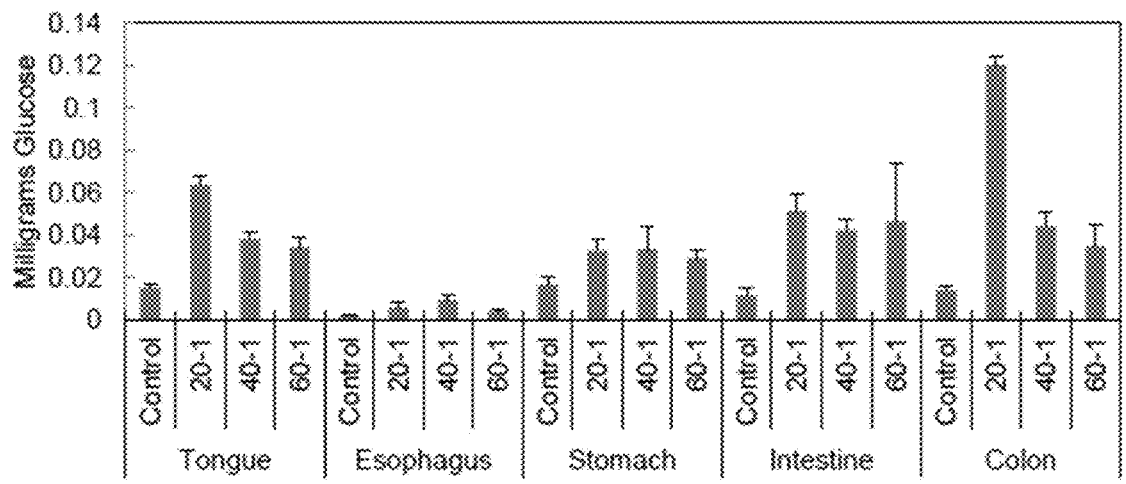
FIGS. 5A-5C are graphs illustrating ex vivo delivery of various substances to various tissue types in accordance with some embodiments.
Figure 5B:
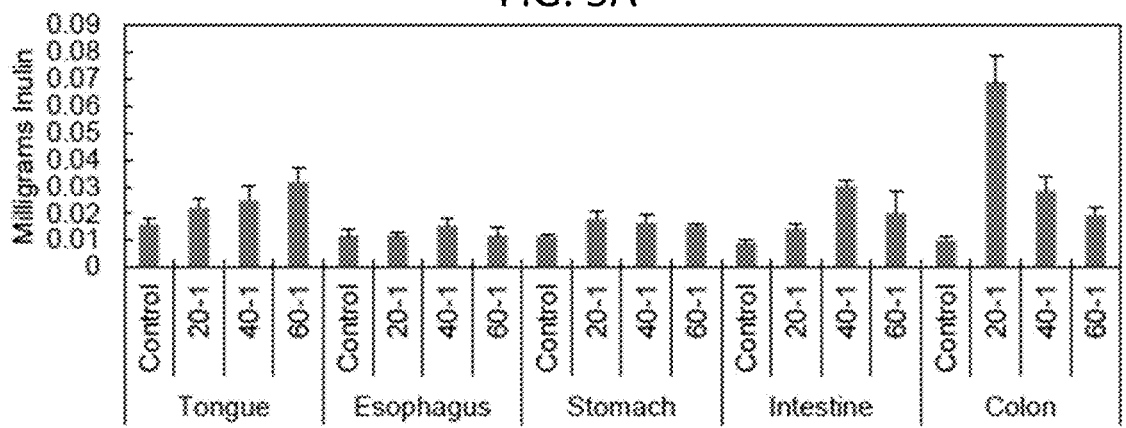
Figure 5C:
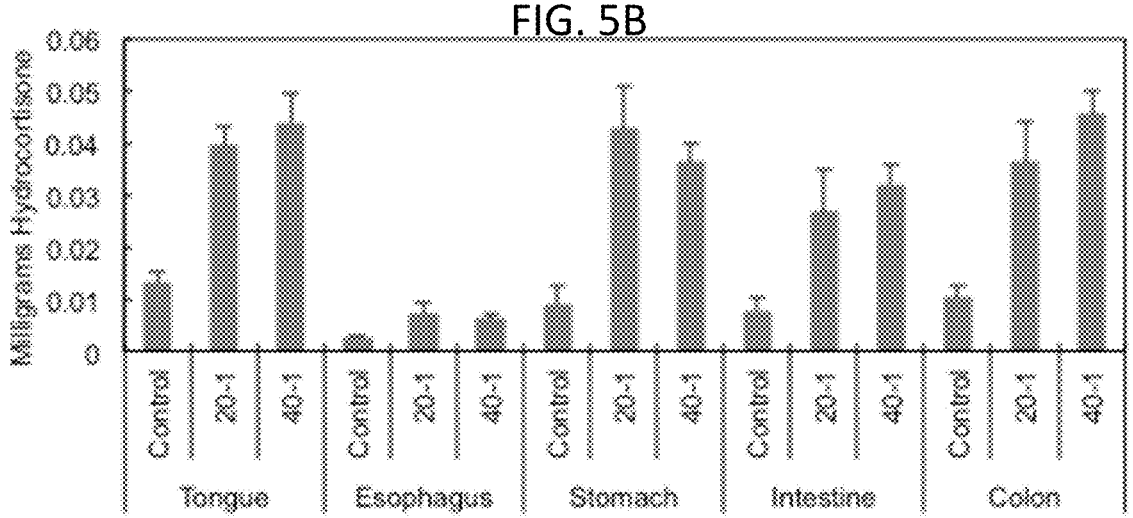

FIGS. 5A-5B are graphs illustrating further in vitro surveys of radiolabeled permeants in different tissue types with treatment or without treatment (Control) in accordance with some embodiments. FIG. 5A depicts glucose delivery (n=3-7), FIG. 5B depicts inulin delivery (n=3-9), and FIG. 5C depicts hydrocortisone delivery (n=6). Treatment was a one-minute exposure to ultrasound at 20 kHz, 40 kHz, or 60 kHz (glucose and inulin only) at an intensity of 2.5 W/cm$^2$, 7.3 W/cm$^2$, and 9.6 W/cm$^2$ respectively. Error bars represent one standard deviation.

EXAMPLE 2: CHARACTERIZATION OF MECHANISMS UNDERLYING DELIVERY ENHANCEMENT

Based on prior studies evaluating phenomena associated with ultrasound transmission through liquids, one or more mechanisms could be contributing to the observed enhancement, including, but not limited to: (1) acoustic streaming, (2) thermal effects, and (3) transient cavitation. To elucidate which mechanisms are dominant, the delivery of tritiated glucose to the small intestine was evaluated under the isolated effects of stirring the donor chamber (to mimic general agitation which would reduce the diffusive boundary layer) as well as sonication with 1 MHz ultrasound at an intensity below the threshold for transient cavitation to isolate the effect of acoustic streaming and heating the tissue. These regimens were compared to delivery using 20 and 40 kHz ultrasound.

A. Acoustic Streaming

To investigate the impact of acoustic streaming and agitation, tissue samples were mounted in Franz diffusion cells as detailed above. A 1 mg/mL solution of glucose spiked with 2 µCi/mL tritiated glucose was used as the model permeant. Immediately before treatment, the donor chamber was filled with 1.5 mL of the glucose solution and a 5 mm magnetic stir bar was added. The donor chamber was then capped and an inverted stir plate was placed on top of the cells ensuring stirring of the donor solution without the stir bar directly agitating the tissue. A Bell-ennium™ 9-position magnetic stirrer (available from Bellco Glass, Inc., Vineland, N.J.) was used to stir the receiver chamber at 500 RPM. The donor chambers were agitated for two minutes total and then immediately removed. The diffusion cell was then disassembled and the receiver solution and tissue sampled for radiometric analysis according to the procedure described above.

The agitated samples were compared to samples treated with the same glucose solution and one of 20 kHz ultrasound at 2.5 W/cm$^2$ and 40 kHz ultrasound at 7.3 W/cm$^2$, according to the same treatment conditions detailed above. Each study group utilized 6 repeats. Stirring did enhance delivery by a factor of 2.10 compared to the control. However, that enhancement and the absolute amount of glucose was significantly less than that achieved with 40 kHz ultrasound.

To investigate the contributions of transient cavitation and acoustic streaming to the mechanism of enhancement, tissue was sonicated with 1 MHz ultrasound to achieve the same energy delivered to the tissue as that delivered using the highest intensity considered in this study (40 kHz at an intensity of at 13.4 W/cm$^2$). In particular, 1 MHz was chosen because it induces stable cavitation and acoustic streaming without transient cavitation as the threshold for transient cavitation is recognized to be well above intensities achievable clinically. Therefore, any enhancement in delivery would be a result of acoustic streaming or stable cavitation.

The larger diameter of commercially available high-frequency ultrasound probes necessitated the use of a larger diffusion cell. Specifically, 29-mm-diameter diffusion cells with receiver chamber volumes of 29 mL were utilized. These diffusion cells result in an exposed tissue area of 6.6 cm$^2$. Tissue was mounted as described previously. The donor chamber was filled with a 1 mg/mL solution containing tritiated glucose. 1 MHz ultrasound was generated using a Dynatron D125 ultrasound probe digitally programmed to an intensity of 2 W/cm$^2$ (determined to be 5.22 W via calorimetry) and continuous operation (available from Dynatronics, Salt Lake City, Utah). Because of the reduced power, treatment was carried out for longer than two minutes. Specifically, tissue was exposed so as to keep constant the total ultrasonic power delivered to the tissue at the highest intensity tested (40 kHz at 13.4 W/cm$^2$). The resulting treatment time, therefore, was 3.4 minutes. Post-treatment, the donor solution was discarded and the tissue washed and sectioned as described previously. Each treatment condition (1 MHz ultrasound or no ultrasound) was repeated three times. As a result of the differences in glucose exposure time and tissue area exposed, results are presented as the ratio of glucose delivered to treated and untreated tissue.

Figure 6:
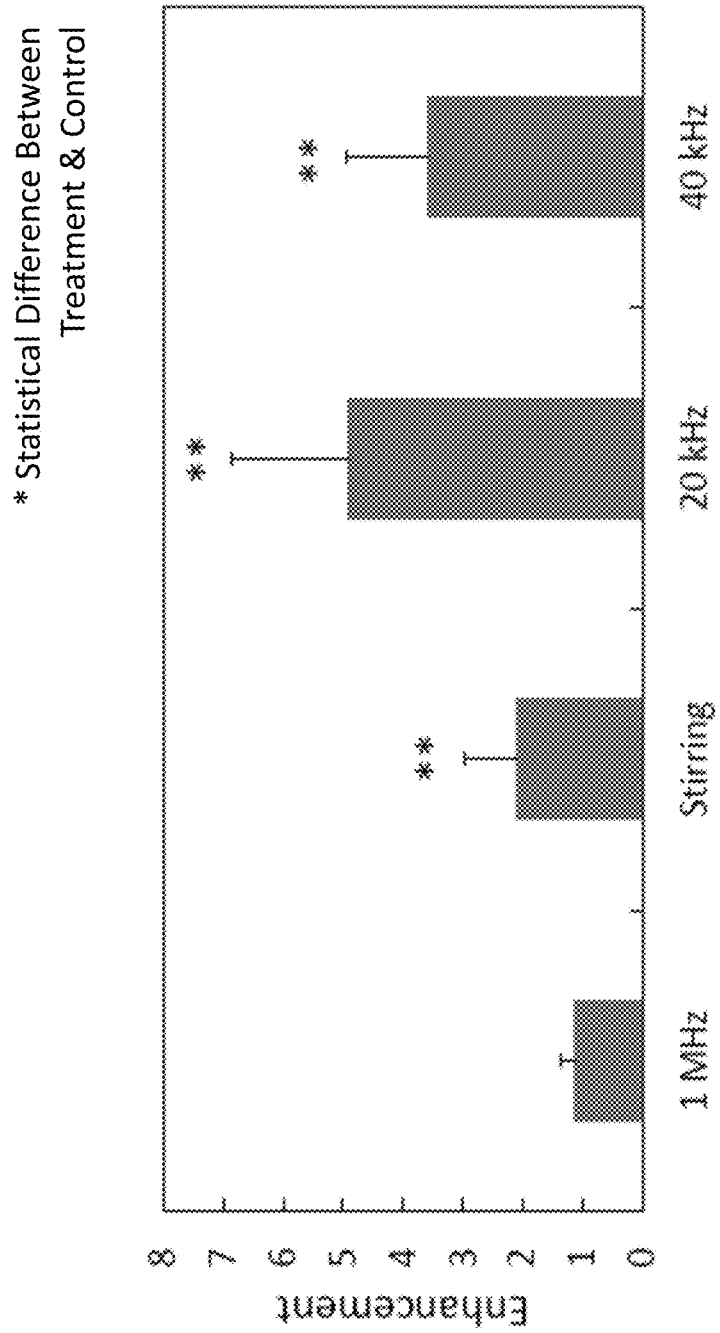
FIG. 6 is a graph illustrating relative enhancement of delivery due to acoustic streaming or agitation in accordance with some embodiments.

FIG. 6 is a graph illustrating relative enhancement in glucose delivery to small intestine as a result of treatment with 1 MHz ultrasound set to 2 W/cm$^2$ (5.22 W actual) for 3.4 min (n=3), stirring of the donor chamber (control n=5, stirring n=6), and 40 kHz ultrasound set to an intensity of 13.4 W/cm$^2$ (control n=5, ultrasound n=3) the quantified enhancement of delivery from donor chamber agitation or ultrasound at 20 kHz or 40 kHz relative to the ultrasound at 1 MHz according to some embodiments. This treatment resulted in no enhancement in glucose delivery. As shown in FIG. 7, delivery enhancement using ultrasound at 20 kHz or 40 kHz is superior to stirring or using 1 MHz ultrasound.

The asterisks (**) indicates a statistical difference between the treatment and its respective control determined by a two-tailed Student's t-test.

B. Thermal Effects

In order to better understand the role of thermal effects in the delivery enhancement, intestinal tissue was treated ex vivo, and the temperature of the tissue was monitored remotely over the course of the treatment. Specifically, tissue was mounted in 15-mm-diameter Franz diffusion cells as described previously. The tissue was then treated for two minutes with 20 kHz ultrasound set to an intensity of 7.5 W/cm$^2$ at a duty cycle of 50% (one minute of ultrasound). During the treatment, the temperature of the donor chamber was monitored remotely using a thermal imaging camera (e.g., FLIR® E50, available from FLIR Systems, Wilsonville, Oreg.). Immediately after treatment, the coupling solution was discarded, and the tissue surface was imaged with the thermal camera to quantify the tissue temperature. Three biological replicates were performed. The measured temperature was noted to be below 40° C.

Figure 7A:
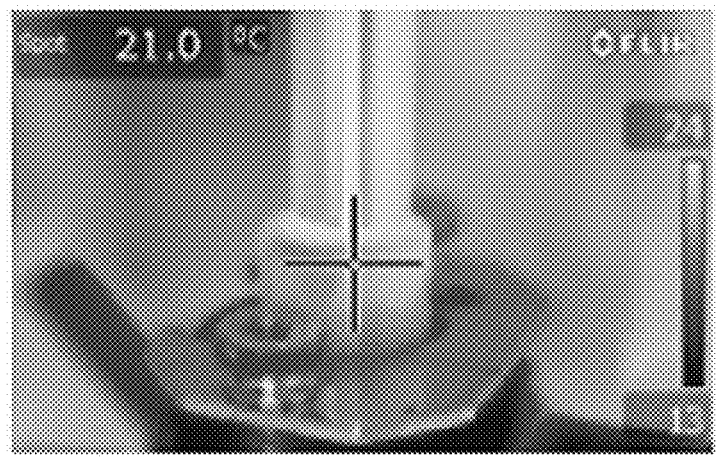
FIGS. 7A-7C are thermal images illustrating thermal effects of delivery in accordance with some embodiments.
Figure 7B:
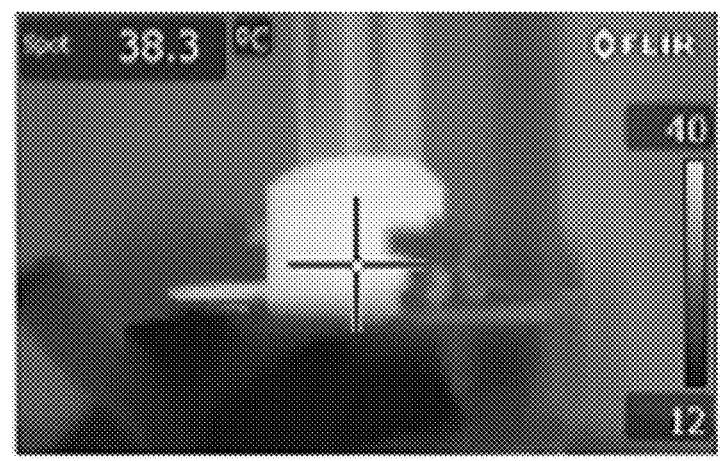
Figure 7C:
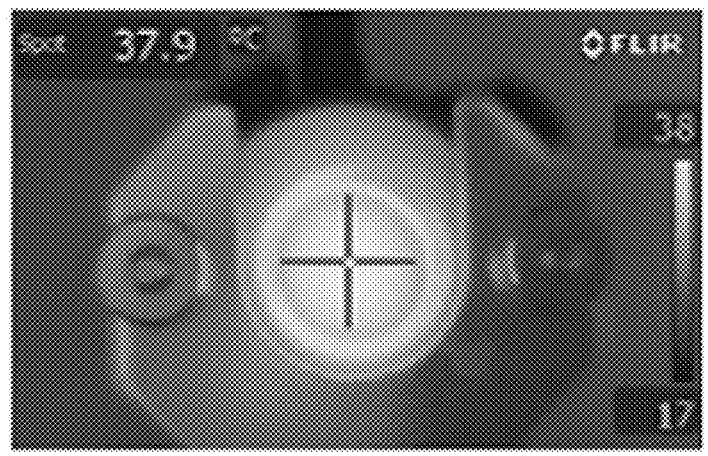

FIG. 7A-7C are representative infrared heat maps captured using the thermal imaging camera in accordance with some embodiments. FIG. 7A is a thermal image of the donor chamber captured before treatment (t=0). The treatment consists of 20 kHz ultrasound set to an intensity of 7.5 W/cm$^2$ at a duty cycle of 50% for 2 minutes total. FIG. 7B is a thermal image of the donor chamber captured after two minutes of treatment (t=2 minutes). FIG. 7C is a thermal image of the intestinal tissue captured immediately after having discarded the coupling solution post-treatment. The lower- and upper-bounds of temperature in the field of view are shown on the right side of each image. The temperature displayed in the upper-left of each image is the temperature at the crosshairs.

The temperatures noted above during ultrasound treatment were then used to test whether heating tissue could enhance delivery. Specifically, separate tissue samples were mounted in 15 mm-diameter Franz diffusion cells. Heat treatment was applied using a circulating water bath (available from, e.g., VWR International, Radnor, Pa.). Specifically, tubing with an outer diameter of 7 mm was fitted to the inlet and outlet of the water bath and insulated. This tubing was then placed in the donor chamber of diffusion cell in an orientation ensuring the donor chamber would fill and maintain a fixed level of fluid. The water bath was filled with deionized water and set to a temperature of 40° C. using the digital temperature controller and confirmed via thermometer. Treatment consisted of either two- or five-minutes of continuous flow of the heated water over the tissue. To control for any tissue disruption as a result of the flowing water, separate diffusion cells were also treated similarly with room temperature water. Immediately after treatment, the donor chamber was filled with a 1 mg/mL solution containing tritiated glucose. This solution was allowed to diffuse for two minutes maintaining constant the permeant contact time across experiments. After exposure, the tissue and receiver chamber were collected and sampled for radiometric content as described previously. Three biological repeats were performed for each water bath treatment.

Figure 8:
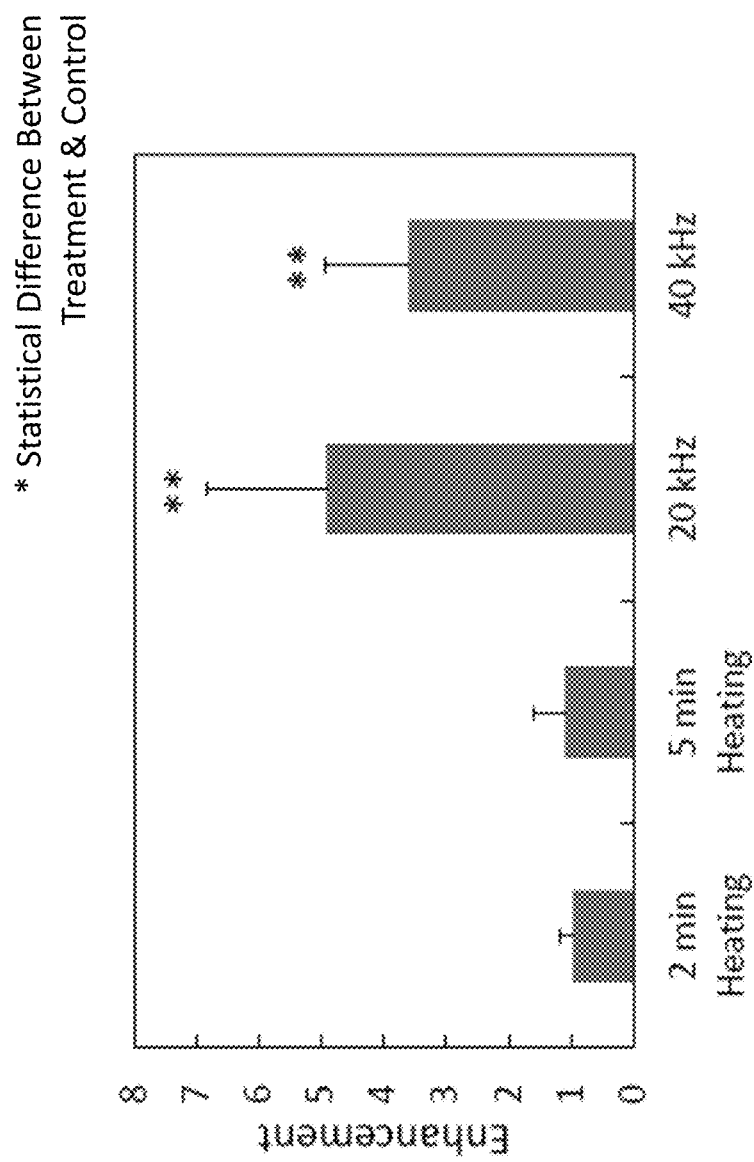
FIG. 8 is a graph illustrating relative enhancement of delivery due to thermal effects in accordance with some embodiments.

Treatment of tissue ex vivo mounted in Franz diffusion cells using 20 kHz ultrasound at 7.5 W/cm$^2$ was found to raise the donor chamber temperature to 40° C. at the end of treatment. There was no difference between the donor chamber temperature and the probe temperature at the end of treatment. Therefore, the enhancement in delivery as a result of heating tissue to 40° C. was tested. FIG. 8 is a graph illustrating the relative enhancement in glucose delivery to small intestine as a result of exposing the tissue to water maintained at 40° C. using a circulating water bath for two or five minutes (n=3 for each treatment) according to some embodiments. The control consisted of recirculating water at room temperature two or five minutes. This is compared to the enhancement in delivery using 20 kHz ultrasound set to an intensity of 7.5 W/cm$^2$ at a duty cycle of 50% for 2 minutes total (control n=5, ultrasound n=3) The asterisks (**) indicate a statistical difference between the treatment and its respective control determined by a two-tailed Student's t-test. Heating of small intestine tissue ex vivo to 40° C. for two or five minutes provided no enhancement in delivery compared to the control.

C. Transient Cavitation

The fact that heating the tissue does not provide an enhancement in delivery suggests that thermal effects do not contribute significantly to the delivery observed using low-frequency ultrasound for the time intervals noted. Acoustic streaming, similarly, would seem to not contribute significantly to the mechanism of enhancement based on the use of 1 MHz ultrasound not enabling any enhancement in delivery. Taken together, these results eliminate the possibility of acoustic streaming or thermal affects to account for the increase in drug delivery observed and suggests that UMGID is a result of transient cavitation.

To confirm the generation of transient cavitation by the application of the various low-frequency ultrasound probes tested in this study in an ex vivo experimental setup, aluminum foil pitting experiments were carried out. Pitting of aluminum foil has been previously validated as an assay for transient cavitation.

To assess whether transient cavitation occurs using 20 kHz, 40 kHz, or 60 kHz at the intensities utilized in this study ex vivo, pits resulting from ultrasound treatment were quantified in aluminum foil as has been done previously in the literature (17, 18). Sheets of aluminum foil were cut into square-inch pieces, avoiding wrinkling. Using vacuum grease, the aluminum foil squares were mounted on the receiver chamber of 15 mm diameter Franz diffusion cell. The vacuum grease enabled the aluminum foil to adhere to the receiver chamber of the diffusion cells. The receiver chamber was then filled with PBS and the cell submerged in PBS. The samples were treated with one of 20 kHz, 40 kHz, or 60 kHz ultrasound at the highest intensity considered for each frequency for 2 seconds. The horn tip was positioned 1 cm above the surface of the aluminum foil. This ensured that the number of discrete pits were not too numerous to quantify. After treatment, the samples were gently peeled from the receiver chambers and mounted on heavy card stock paper. These were then scanned using a CanoScan 8800F flatbed scanner (available from Canon, Tokyo, Japan) at 1200 dpi in grayscale mode and saved in the BMP file format. Pits were then counted manually from these images.

FIG. 9A is a graph illustrating the number of pits observed in the above aluminum foil pitting experiments when treated using 20 kHz, 40 kHz, or 60 kHz ultrasound for 2 seconds at the highest intensity considered for each frequency (n=5 for each frequency) according to some embodiments. FIGS. 9B, 9C, and 9D are representative images of pitted aluminum foil samples treated with 20 kHz, 40 kHz, or 60 kHz ultrasound, respectively. The scale bar in these images represents 3 mm. The number of pits generated with 20 and 40 kHz was found to be statistically greater than the number of pits generated with 60 kHz ultrasound (one-way ANOVA with multiple comparisons, P<0.023). Conversely, no pitting was visible when 1 MHz ultrasound was applied.

Because these results suggest that transient cavitation is occurring, theoretical pore sizes generated in the small intestine as a result of treatment with 20 kHz ultrasound were calculated utilizing hindered-transport theory with radiolabeled glucose and inulin as the model permeants.

Side-Bi-Side™ diffusion cells (available from PermeGear, Hellertown, Pa.) with inner diameters of 9 mm were used to determine permeability. Tissue was placed between the two chambers and clamped together with the luminal side facing the donor chamber. Stir bars were added to both the donor and receiver chambers and agitated using the Bell-ennium™ 9-position magnetic stirrer.

The donor solution consisted of 2 µCi/mL 3H-glucose and 2 µCi/mL 14C-labeled inulin. Each donor chamber was filled with 3 mL of this solution and the receiver solution was filled with 3 mL fresh PBS. At 10-minute intervals over the course of one hour, 100 µL samples were taken from the receiver chamber and replaced with an equal volume of fresh PBS. Then, 15 mL of Hionic Fluor was added to these samples and analyzed for tritiated decomposition and 14C decomposition. Seven repeats were performed for the Control samples, and 17 for the Treated samples. The need for more repeats for the ultrasound-treated group was as a result of the heterogeneous nature of the permeabilization.

Figures 10A, 10B, 10C:
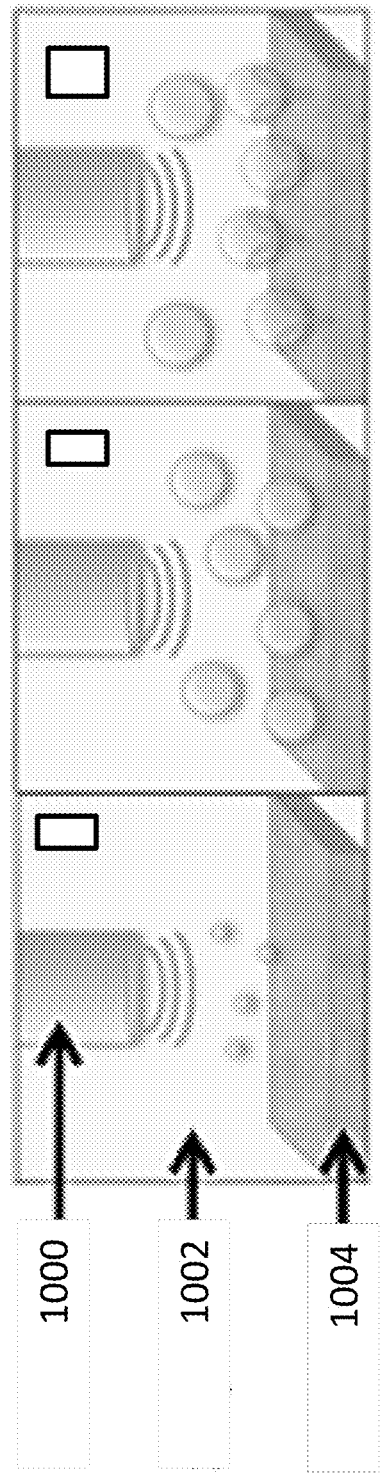
FIGS. 10A-10C are diagrams illustrating a mechanism of ultrasound-enhanced delivery in accordance with some embodiments.

FIGS. 10A-10C are diagrams illustrating one hypothesized mechanism of ultrasound-enhanced GI delivery. As shown in FIG. 10A, ultrasound emission from the probe or horn tip 1000 results in the formation of cavitation bubbles in the coupling fluid 1002 above the tissue 1004. As treatment continues the number of nucleated bubbles increases and the bubbles move around chaotically and grow in size through a process known as rectified diffusion shown in FIG. 10B. Finally, some of the bubbles reach a threshold size above which they are no longer stable. These bubbles implode, creating a jet of fluid, referred to as a microjet, which impinges against the tissue and drives drug into the tissue as shown in FIG. 10C.

To further elucidate the mechanism of enhancement of UMGID, theoretical pore-size estimates were made using hindered-transport theory, which has previously been utilized to model diffusion across membranes. The permeability P of a molecule traversing a porous membrane can be expressed as follows in Equation 1:

$$P = CDF(\lambda) \quad (1)$$

where C is a constant depending solely on properties of the membrane, D is the free diffusion coefficient of the molecule in solution, and $F(\lambda)$ is known as the hindrance factor which depends on the ratio $\lambda$ of the hydrodynamic radius of the molecule and the membrane pore radius. The most advanced expression of $F(\lambda)$ is as follows in Equation 2:

$$F(\lambda) = 1 + \frac{9}{8}\lambda \ln \lambda - 1.56034\lambda + 0.528155\lambda^2 + 1.91521\lambda^3 - 2.81903\lambda^4 + 0.270788\lambda^5 + 1.10115\lambda^6 - 0.435933\lambda^7 \quad (2)$$

Because both C and the membrane pore size (embedded in $\lambda$) in Equation 1 are unknown, two permeant molecules may be used to eliminate C as follows in Equation 3:

$$\frac{P_x}{P_y} = \frac{D_x F(\lambda_x)}{D_y F(\lambda_y)} = K \quad (3)$$

The only unknown in Equation 3 is the pore size in $\lambda$. Therefore, P may be determined experimentally for each permeant to estimate the membrane pore size. The permeability can be found using the following expression in Equation 4:

$$P_i = \frac{1}{AC_i} \frac{dQ_i}{dt} \quad (4)$$

where A is the area of the membrane exposed to the permeant, $C_i$ is the concentration of the permeant in the donor chamber, and $dQ_i/dt$ is the slope of the plot of the permeant quantity in the receiver chamber versus time after the lag-phase.

The permeability of each molecule in tissue not treated with ultrasound was found to be $1.28 \times 10^{-4} \pm 5.05 \times 10^{-5}$ and $1.36 \times 10^{-5} \pm 6.77 \times 10^{-6}$ cm/min respectively. In ultrasound treated samples, the average permeability of glucose and inulin was $1.95 \times 10^{-4} \pm 4.84 \times 10^{-5}$ and $2.94 \times 10^{-5} 1.36 \times 10^{-5}$ cm/min respectively. Ultrasound was found to result in a statistically higher permeability for both glucose and inulin (two-tailed Student's t-test, $P \leq 0.008$). These values were along with the diffusion coefficients and hydrodynamic radii of glucose and inulin were used in Equations 1-4 to calculate the theoretical pore sizes generated when porcine small intestine was treated with 20 kHz for 2 minutes at a 50% duty cycle. A 95% confidence interval of the regression slope is presented with sample size n and membrane radius squared $r^2$ in TABLE 1.

TABLE 1

|  | n | Slope | $r^2$ |
|---|---|---|---|
| Control | 7 | 1.26 ± 0.38 | 0.94 |
| Treated (20 kHz) | 17 | 1.55 ± 0.64 | 0.68 |

From Equation 3 above, it can be seen that a plot of $\log(P_x)$ against $\log(P_y)$ should yield a linear curve with a slope of one and a y-intercept of $\log(K)$. Therefore, linear regressions were fitted to both the Control and Treated plots of $\log(P_{glucose})$ versus $\log(P_{inulin})$ and required that the 95% confidence interval of the slope contain the theoretical value of one. The fact that the theoretical slope of one is contained in the 95% confidence interval of both experimental groups supports the validity of this analysis, and therefore, it is reasonable to deduce pore sizes using Equations 2 and 3.

Figures 11A, 11B:
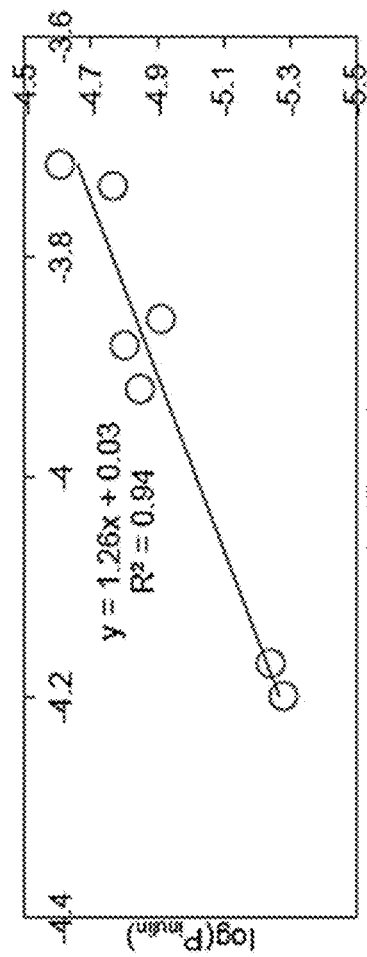
FIGS. 11A and 11B are plots illustrating $\log(P_{glucose})$ against $\log(P_{inulin})$ for the small intestine in accordance with some embodiments.
Figure 12A:
FIGS. 12A-12D are images illustrating cross-sections of colonic tissue exposed to fluorescent-activated 3 kDa dextran or 70 kDa dextran with or without treatment with 20 kHz ultrasound in accordance with some embodiments.
Figure 12B:
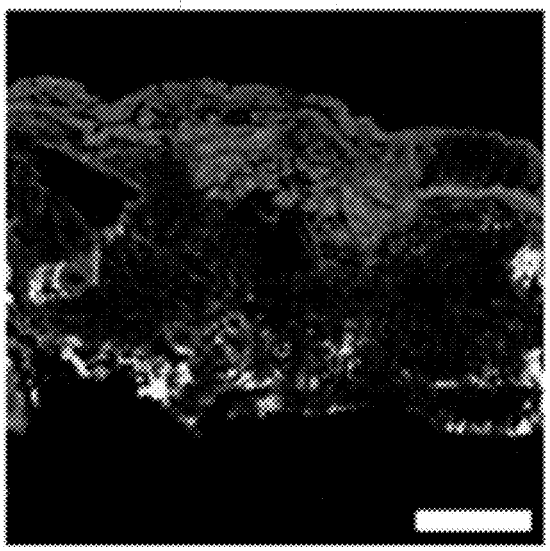
Figure 12C:
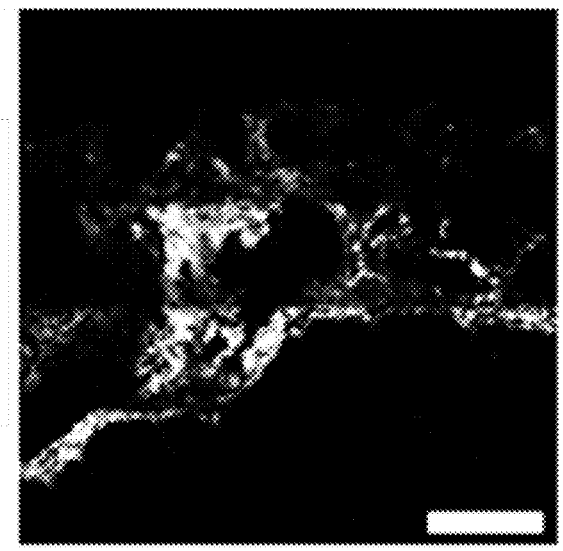
Figure 12D:
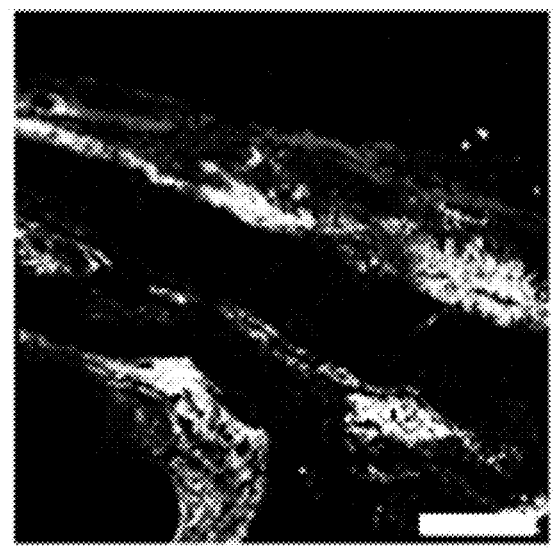

FIGS. 11A and 11B are plots illustrating $\log(P_{glucose})$ against $\log(P_{inulin})$ for the small intestine according to some embodiments. In particular, FIG. 11A depicts this relationship in untreated tissue while FIG. 11B depicts the relationship in tissue treated with 20 kHz ultrasound at a 50% duty cycle for two minutes (i.e., one minute total of ultrasound exposure).

Values of K were calculated for every sample using Equation 3 above. The average, and lower and upper pore size estimates are based on the average value of K and the 95% confidence interval for K.

TABLE 2 provides lower, average, and upper estimates of pore size radius created in small intestine tissue as a result of ultrasound exposure using this model. The upper limit on the calculated theoretical pore radii in untreated intestine was found to be 53 Å, compared to an upper limit of 90 Å in treated samples.

TABLE 2

| | Pore Size (Angstrom) | | |
| --- | --- | --- | --- |
| | Lower | Average | Upper |
| Control | 41.6 | 46.3 | 53.7 |
| Treated (20 kHz) | 53.4 | 65.2 | 90.6 |

In order to visualize the permeation of molecules and characterize the tissue distribution of ultrasound-mediated analyte delivery, colonic tissue was treated in vitro with dextran labeled with Texas red in the donor chamber. Specifically, porcine tissue was mounted in 15 mm-diameter Franz diffusion cells as described previously. Skin was treated with 20 kHz ultrasound at the highest power considered as described previously. The coupling solution contained either 3 kDa dextran or 70 kDa dextran at a concentration of 1 mg/mL. Immediately after treatment, the coupling solution was discarded and the tissue washed thoroughly with PBS to remove any residual dextran. The diffusion cell was then disassembled and the tissue exposed to dextran carefully dissected and fixed in 10% formalin. The tissue sections were then mounted in paraffin blocks. Two, 8-μm-thick sections separated by a 200-μm step were then mounted to glass microscope slides for subsequent imaging of the tissue. Tissue samples not treated with ultrasound were also exposed to dextran keeping the permeant contact time constant (2 minutes). These samples were subsequently processed similarly.

Resulting histology slides were imaged with a FluoView™ FV1000MP multiphoton microscope (available from Olympus, Tokyo, Japan) with a 25×, 1.05 N.A. objective. Samples were excited at 860 nm using a Ti-Sapphire pulsed laser (available from Spectra-Physics, Santa Clara, Calif.). Emission was collected with a 607/70 nm band-pass filter, and collagen was imaged by second harmonic generation at 430 nm. Individual image channels were combined in ImageJ.

FIGS. 12A-12D are multiphoton microscopic images of cross-sections of colonic tissue exposed to 3 kDa dextran or 70 kDa dextran labeled with Texas red with or without treatment with 20 kHz ultrasound according to some embodiments. The red channel and second harmonic are shown. The scale bar represents 500 μm.

Without ultrasound, there was no visible permeation of 3 or 70 kDa dextran into colonic tissue. This is to be contrasted with the use of 20 kHz ultrasound, which enabled significant penetration of both 3 and 70 kDa dextran into the tissue. Dextran was observed throughout the entire thickness of the colonic tissue when ultrasound was utilized. This suggests that ultrasound enables drug to rapidly permeate the tissue. This was further confirmed by analyzing the distribution of radiolabeled compounds between the tissue and receiver chamber. The permeant content in the tissue was significantly greater than that present in the receiver chamber as a result of ultrasound treatment. Inulin delivery to colonic tissue, for example, resulted in 90-fold more inulin in the tissue compared to that in the receiver chamber on average.

EXAMPLE 3: EFFECTS OF SONICATION ON THERAPEUTIC COMPOUND STRUCTURE AND FUNCTION

The effect of sonication on the molecular structure of mesalamine and hydrocortisone was investigated by analyzing the molecules after sonication using nuclear magnetic resonance (NMR). Mesalamine and hydrocortisone samples were prepared at a concentration of 4 mg/mL in deuterated DMSO. Samples of 1.5 mL were sonicated with 20 kHz ultrasound at the highest intensity considered as described above. Three biological replicates were performed. Unsonicated samples were used as the control. A Varian 500 (1H, 500 MHz) spectrometer was used to record 1H NMR spectra, then processed using Mnova NMR software (available from Mestralab Research, A Coruña, Spain). The 1H NMR spectra were referenced with residual non-deuterated solvent shifts (DMSO-d5=2.5 ppm). All shifts are reported in ppm. Note the disappearance of the volatile internal tetramethylsilane (TMS) standard after ultrasound treatment, which was carried out in an uncapped vial.

FIGS. 13A-13B depict representative NMR spectra of mesalamine and hydrocortisone before and after sonication according to some embodiments. FIG. 13A shows representative NMR spectra of mesalamine after sonication 1300 and before sonication 1302. After sonication 1300: 1H NMR (500 MHz, DMSO) δ Majority: 7.16 (1H, d, J=2.8 Hz); 6.90-6.87 (1H, dd, J=2.8, 8.8 Hz); 6.70 (1H, d, J=8.8 Hz). Minority: 7.10 (1H, d, J=3.1 Hz); 6.98-6.96 (1H, dd, J=3.1, 8.9 Hz); 6.67 (1H, d, J=8.9 Hz). Before sonication 1302: 1H NMR (500 MHz, DMSO) δ 7.12 (1H, d, J=2.8 Hz); 6.87-6.84 (1H, dd, J=2.8, 8.8 Hz); 6.68 (1H, d, J=8.8 Hz).

FIG. 13B shows representative NMR spectra of hydrocortisone after sonication 1304 and before sonication 1306. After sonication 1304: 1H NMR (500 MHz, DMSO) δ5.56 (1H, s); 5.19 (1H, s); 4.52-4.47 (1H, d, J=19.1 Hz); 4.30 (1H, bm); 4.25 (1H, bm); 4.09-4.05 (1H, d, J=19.1 Hz); 2.56 (1H, m); 2.40 (2H, m); 2.20 (2H, m); 2.07 (1H, m); 1.90 (3H, m); 1.78 (1H, m); 1.65 (2H, m); 1.54 (1H, m); 1.40 (1H, m); 1.36 (3H, s); 1.26 (1H, m); 0.99 (1H, m); 0.85 (1H, m); 0.74 (3H, s). Before sonication 1306: 1H NMR (500 MHz, DMSO) δ5.56 (1H, s); 5.19 (1H, s); 4.67 (1H, m); 4.52-4.47 (1H, dd, J=5.9, 19.1 Hz); 4.29 (1H, d, J=3.32); 4.25 (1H, p, J=3.32); 4.10-4.05 (1H, dd, J=5.9, 19.1 Hz); 2.56 (1H, m); 2.40 (2H, m); 2.20 (2H, m); 2.07 (1H, m); 1.92 (3H, m); 1.78 (1H, m); 1.65 (2H, m); 1.54 (1H, m); 1.40 (1H, m); 1.36 (3H, s); 1.26 (1H, m); 0.99 (1H, m); 0.85 (1H, m); 0.74 (3H, s). Three biological replicates were performed for both sonicated and unsonicated samples.

Deuterium exchange occurs as labile protons on the analyte exchange with the deuterated solvent in which it is dissolved. This exchange is catalyzed during the ultrasound reaction and is apparent in the post-ultrasound samples as shown in FIGS. 13A-13B. Replacement of protons by deuterium results in loss of signal, shown either as a reduction in the integration fractions or disappearance of the peak altogether. Other indications of deuterium exchange include a slight broadening of peak shape, a shift in peak location, and slight change in J coupling values. These changes reflect the natural equilibrium of labile protons in solution and do not reflect changes in the overall molecular structure.

Finally, the effect of sonication on insulin structure was also assessed. Two hundred units of rapid-acting insulin were formulated in 10 mL of PBS. This sample was then sonicated with 20 kHz ultrasound at the highest intensity considered as described above. Three biological repeats were performed for both sonicated and unsonicated groups. Insulin structure was analyzed by reversed phase analytical HPLC using a ZORBAX Eclipse Plus C18 column (4.6×100 mm, 3.5 μm) (available from Agilent, Lexington, Mass.), with a mobile phase gradient from 95% to 5% of acetic acid (1.5%) in water in acetonitrile over 15 minutes. FIG. 13D is a graph illustrating impact of sonication on insulin function according to some embodiments. The averages and standard deviations are shown. No statistical difference was found on the concentration of active insulin as a result of sonication with 20 kHz set to an intensity of 7.5 W/cm² (two-tailed Student's t-test, P=0.48).

EXAMPLE 4: IN VIVO DELIVERY STUDIES

Given the efficacy of UMGID in vitro, as well as prior observations that drug delivery by traditional methods is generally greater in vivo than in vitro, this technology may translate into even greater degrees of drug delivery enhancement in vivo. Further, two different configurations of UMGID were tested in vivo for delivery efficacy: axial emission in swine and radial emission in mice (described below).

A. In Vivo Delivery Using Axial UMGID in Swine

FIG. 14A is a flowchart outlining the procedure for in vivo delivery according to some embodiments. In step 1400, the subject is prepared for the procedure. A porcine model was selected for this study due to the similarity between its anatomical features and that of human subjects, including tissue architecture, size, and metabolism. Both female and male Yorkshire pigs between 45-80 kg in weight were used for one study based on the availability of sex from the vendor. All procedures were conducted in accordance with protocols approved by the Massachusetts Institute of Technology Committee on Animal Care. Before every experiment, the animal was fasted overnight. Sedation was induced with intramuscular injection of Telazol® tiletamine, 5 mg/kg (available from Zoetis, Inc., Florham, N.J.), xylazine 2 mg/kg, and atropine 0.04 mg/kg. The animal was then intubated and sedation maintained with isoflurane (1-3% inhaled).

In step 1402, the subject's rectum is cleared, for example, with a tap water enema. In the study, a clean rectum was confirmed by colonoscopy prior to treatment.

In step 1404, a medicated enema is instilled. In the study, a PBS solution of mesalamine at the same volume (60 mL) and concentration (66.6 mg/mL) used clinically was prepared and instilled.

In step 1406, ultrasound is applied. In the study, Control and Treatment tests were performed on separate days. For Treatment tests, the ultrasound treatment was applied using a 20 kHz horn for 2 minutes at a 50% duty cycle at an intensity of 7.5 W/cm². For Control tests, the ultrasound probe was inserted into the colon, but not turned on (n=16).

Additionally, the temperature increase as a result of ultrasound treatment was also quantified. To do this, a thermocouple (available from, e.g., Kruuse, Langeskov, Denmark) was placed directly in the rectum during treatment. Temperature measurements were recorded continuously throughout the 2-minute treatment. With regards to temperature, this treatment was found to result in an average increase in temperature of 1.04±0.66° C. (n=3). The minimal effect on temperature was expected given the short treatment time and volume of the enema (60 mL). The negligible rise in temperature further supports the hypothesis that thermal effects are not responsible for the increase in drug delivery.

In step 1408, the tissue is biopsied for further assessment. Colonic areas treated with ultrasound were biopsied using endoscopic biopsy forceps (available from, e.g., US Endoscopy, Mentor, Ohio) for drug delivery evaluation as well as histological analysis (n=13).

FIG. 14B is a diagram illustrating this experimental setup according to some embodiments. A prototype hand-held probe 1410 for delivering a medicated enema 1412 was designed to include an ultrasound emitter 1414 and an enema administering device 1416. In FIG. 14B, the probe 1410 is shown inserted into a rectum of a subject for delivering the medicated enema and 20 kHz ultrasound. In some embodiments, the hand-held probe devices are light-weight, with dimensions amenable to insertion into the rectum of a subject. For example, the size of the probe tip that s inserted may be comparable to the size of a standard colonoscope.

Clinical monitoring of the animals demonstrated overall initial safety. Safety evaluations were performed through the insertion of the 20 kHz probe into the rectum followed by biopsies of the treated site and an adjacent, untreated area of the colonic mucosa. Histological examination demonstrated only minor epithelial disruption in <5% of the treated area examined as determined by a clinical pathologist. Specifically, there was minor cellular disarray in the control samples, which was determined to be an artifact due to the fixation procedure. In the samples treated with ultrasound, patchy saponification of the adipose tissue was noted. Further, minimal congestion of intramucosal capillary vessels located in the superficial submucosa was noted. There was no evidence of epithelial damage and mucosal integrity was maintained. FIGS. 15A-15B are macroscopic views of untreated and treated tissue, respectively. FIGS. 15C-15D are histological views of untreated and treated tissue, respectively. The outlined area 1500 indicates minor localized saponification of the muscularis in <5% of the treated area examined. The scale bar represents 100 μm.

Figure 16:
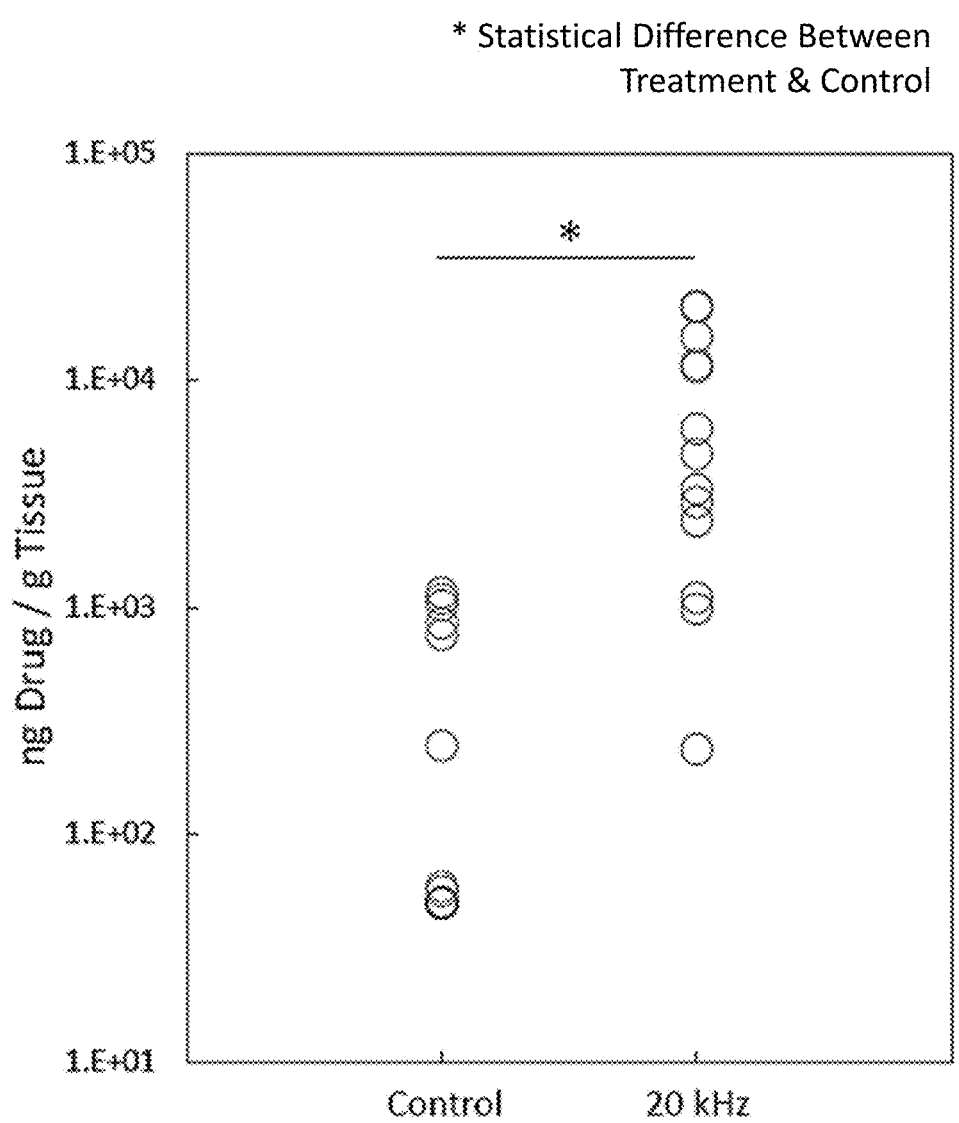
FIG. 16 is a plot of drug content in tissue biopsies normalized by the mass of the tissue biopsies in accordance with some embodiments.

The efficacy of mesalamine delivery was then assessed with the same 1 minute treatment regimen used in the in vitro testing. A mesalamine enema at the concentration and volume used clinically (Rowasa® mesalamine, 4 g (available from Meda Pharmaceuticals, Somerset, N.J.) in 60 mL suspension) was instilled in the swine rectum immediately followed by UMGID. Gas chromatography/mass spectrometry (GC/MS)-based quantification of mesalamine in tissue biopsies taken immediately following UMGID demonstrated a 22.4-fold increase in delivery using ultrasound compared to colonic tissue not treated with ultrasound (P=4.06×10⁻⁴). FIG. 16 is a graph illustrating mesalamine drug content in tissue biopsies normalized by the mass of the tissue biopsy as a result of placement of a mesalamine enema in the colon without (Control) and with (Treatment) 20 kHz ultrasound according to some embodiments. Each point represents one biological replicate (n=16 for Control, n=13 for Treatment). The P-value represents a two-tailed Student's t-test. It should be further noted that one-half of the untreated samples were found to have a drug content below the limit of detection (50 ng/g tissue). ¹H NMR spectroscopy was used to confirm the chemical stability of mesalamine after treatment with ultrasound (see Example 3 above).

In addition to the delivery of mesalamine, insulin, a model biologic, was evaluated to determine the potential of UMGID to deliver larger, biologically active molecules. The same 1-minute ultrasound treatment with an insulin enema resulted in a robust hypoglycemic response. FIGS. 17A-17B are graphs illustrating normalization of blood-glucose to its starting values as a result of placement of an enema containing 100U insulin without or with, respectively, simultaneous 20 kHz ultrasound treatment according to some embodiments. Each individual curve in FIGS. 17A-17B is a biological repeat. FIG. 17C is a bar graph representing the average and standard deviation after 40 minutes of monitoring. The P-value represents a two-tailed Student's t-test. Sonication of insulin was similarly found to have no impact on its active protein structure (see Example 3 above).

Successful delivery of drugs varying in molecular weight by an order of magnitude supports the likely broad applicability of UMGID.

B. In Vivo Delivery Using Radial UMGID in Mice

The clinical relevance of the enhancement in mesalamine delivery was analyzed in a murine model of dextran sodium sulfate (DSS)-induced acute colitis. This murine model was chosen because it is recognized to not benefit from topical mesalamine administration. Therefore, improvement in disease indices in this model as a result of ultrasound treatment would underscore the impact of UMGID. Given the colonic anatomy and the often circumferential nature of colitis involvement, it was hypothesized that radial UMGID would be most beneficial so as to direct the treatment over the largest area of inflamed tissue.

Figure 18A:
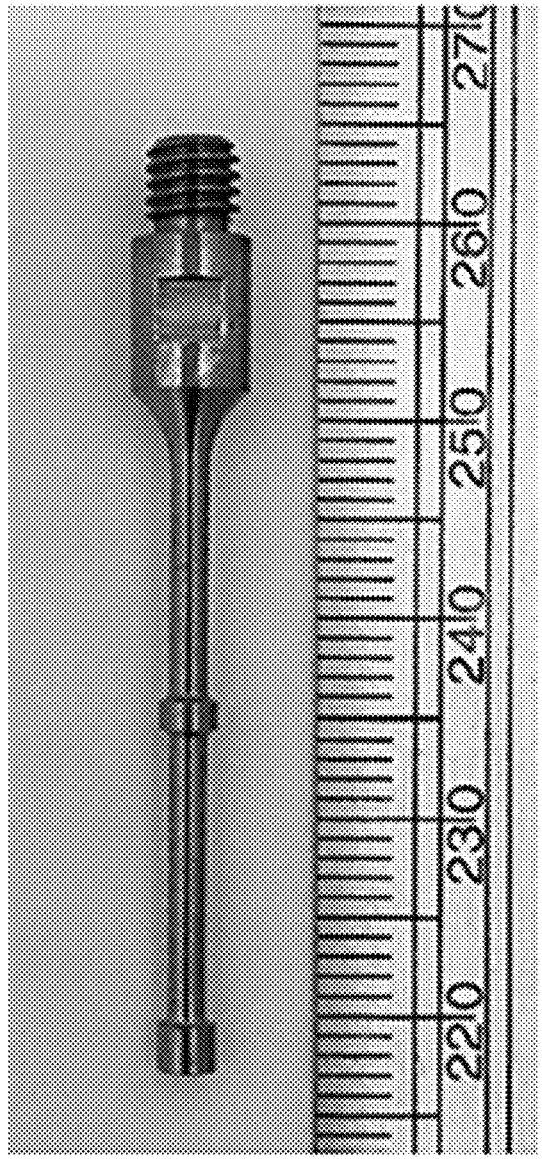
FIG. 18A is an image of a probe device in accordance with some embodiments.

Radial emission was achieved using a custom-designed miniature ultrasound probe with dimensions amenable to insertion directly into the mouse colon (probe diameter≤3 mm) according to some embodiments. FIG. 18A is an image of the ultrasound probe tip with a shaft diameter of 2 mm. The two bumps shown have a diameter of 3 mm and enhance radial ultrasound emission. This device was found to result in no measurable temperature increase as a result of the short treatment time and the formation of pits was confirmed in aluminum foil samples.

Figure 18B:
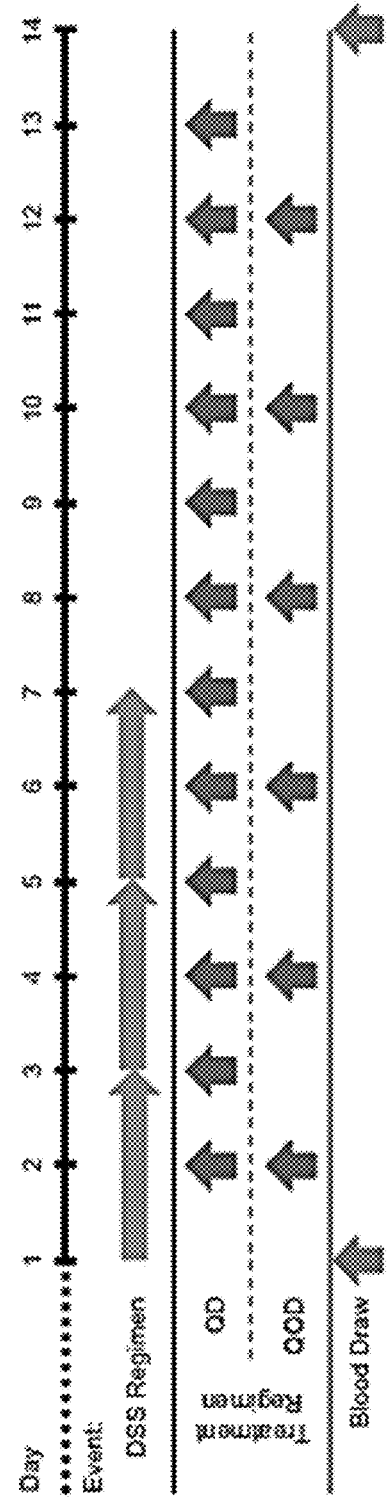
FIG. 18B is a diagram illustrating a treatment schedule in accordance with some embodiments.

The tolerability of this device was first tested in healthy animals in the absence of colitis. Specifically, the effect daily probe insertion and probe insertion followed by sonication were tested over a 14-day course for subsequent comparison to the disease groups. FIG. 18B is a diagram illustrating the colitis induction and treatment schedule for in vivo radial UMGID of mesalamine according to some embodiments. The result of repeated probe insertion and probe insertion followed by sonication were compared to a control group that received no manipulation. Treatment followed the daily (QD) regimen presented in FIG. 18B. Treatment was found to be well tolerated and all animals were free of clinical signs of distress over the 14 day period.

With regard to the potential for local trauma induced directly in the colon in healthy animals, mice pre- and post-probe insertion with and without ultrasound were evaluated to determine treatment resulted in localized trauma leading to rectal bleeding or inflammation. On gross examination, the organs appeared normal without any ecchymoses noted over the organs.

Figure 19B:
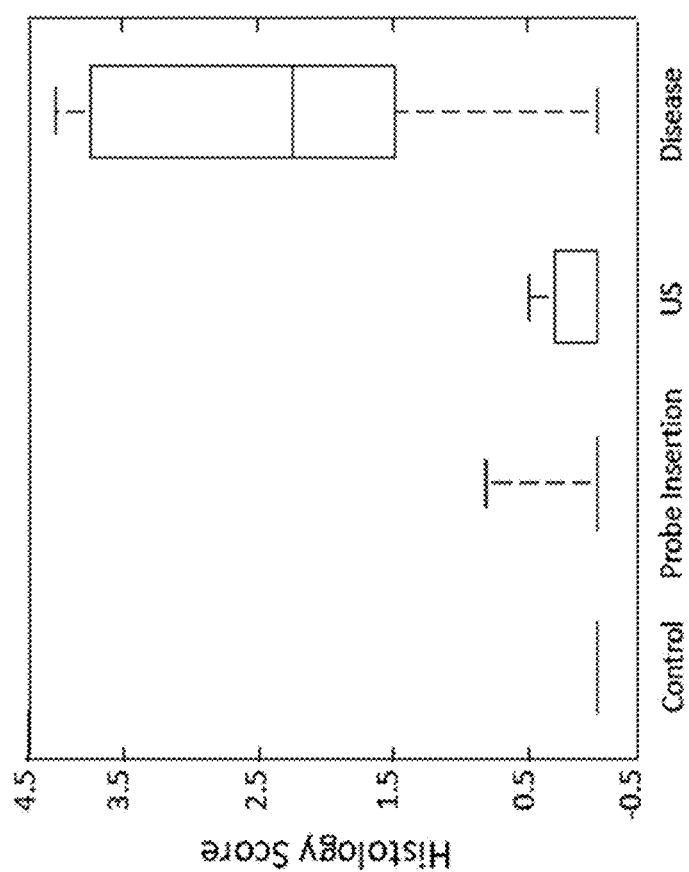
FIG. 19B is a plot illustrating effects of ultrasound on histology scores in accordance with some embodiments.
Figure 19A:
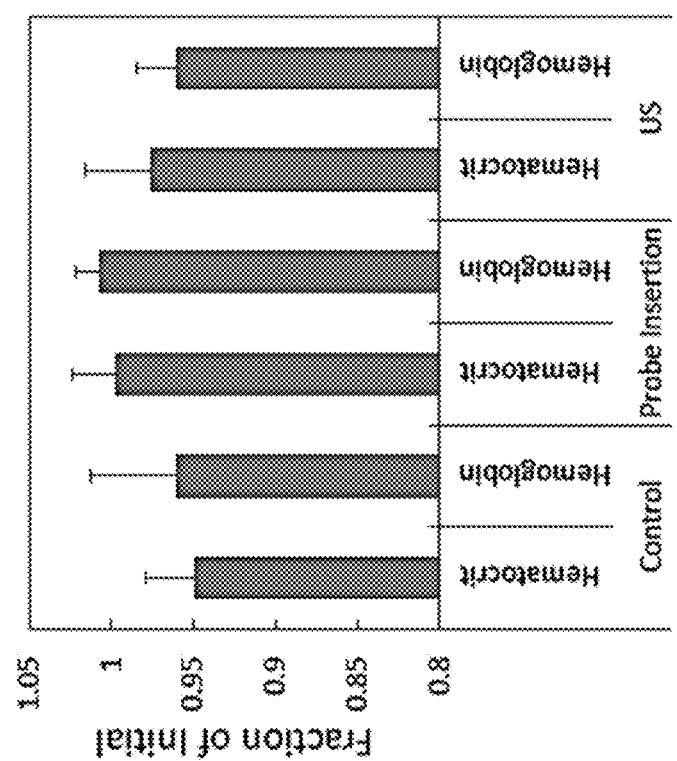
FIG. 19A is a graph illustrating effects of ultrasound on blood markers according to some embodiments.

FIG. 19A is a bar graph illustrating the effect of rectal ultrasound on blood markers according to some embodiments. With regards to hematocrit and hemoglobin levels, a one-way analysis-of-variance showed there to be no statistical difference between any group's final normalized hematocrit or hemoglobin, suggesting that probe insertion and sonication does not induce significant blood loss and is well tolerated. In FIG. 19A, hematocrit and hemoglobin normalized to day 1 for healthy animals (Control), healthy animals receiving daily probe insertion (Probe Insertion), and healthy animals receiving daily ultrasound sonication (US). While five animals were used in each group, some blood samples from day 1 and day 14 clotted, resulting in fewer than five values for some groups.

Histological examination at Day 14 was selected to assess the effect of repeated dosing and to allow for comparison to results from animals with disease induced receiving a clinically-utilized 14-day course of treatment. Histology scores also showed both the Probe Insertion and US groups to have statistically better histology scores than any other group that had disease induced (one-way analysis of variance testing with multiple comparisons, P<0.015). FIG. 19B is a graph illustrating the effect of rectal ultrasound on histology scores of tissue sections at Day 14 according to some embodiments. The median, 25th, and 75th percentiles are shown, and the whiskers indicate the most extreme data points.

Figure 20:
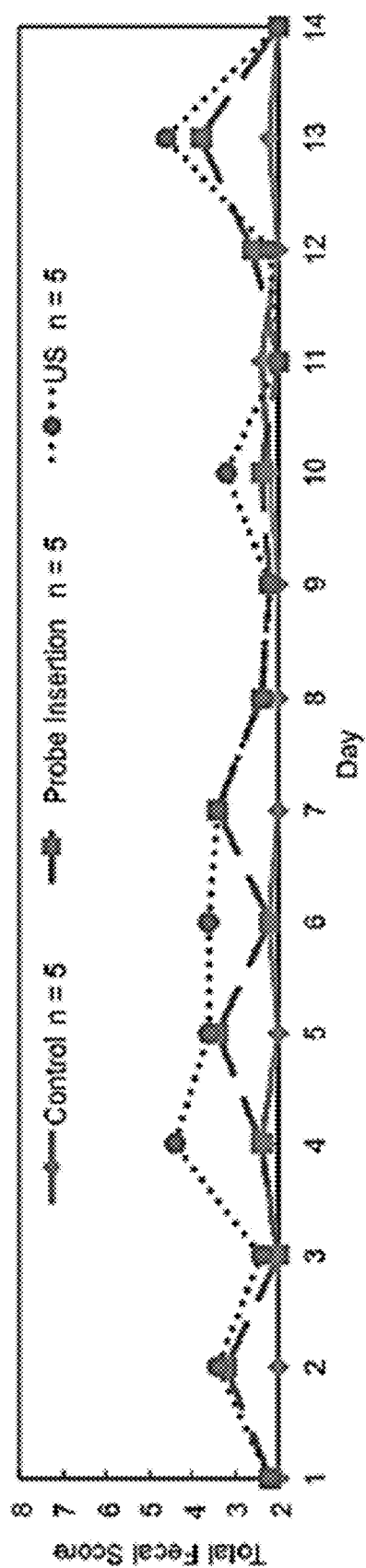
FIG. 20 is a plot illustrating effects of ultrasound on fecal scores in accordance with some embodiments.
Figure 22A:
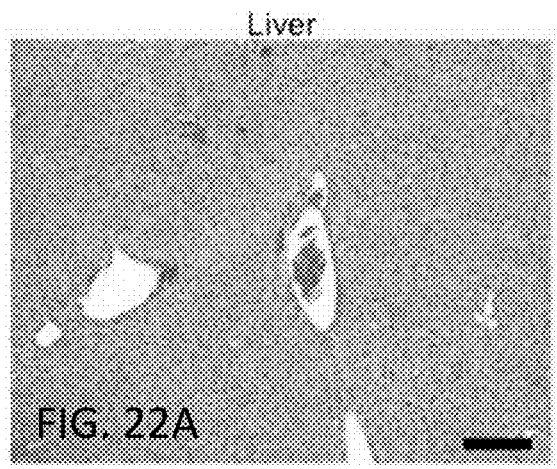
FIGS. 22A-22F are images illustrating effects of ultrasound on histology in accordance with some embodiments.
Figure 22B:
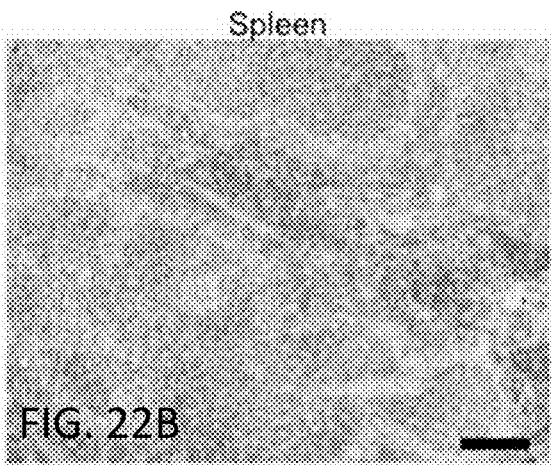
Figure 22C:
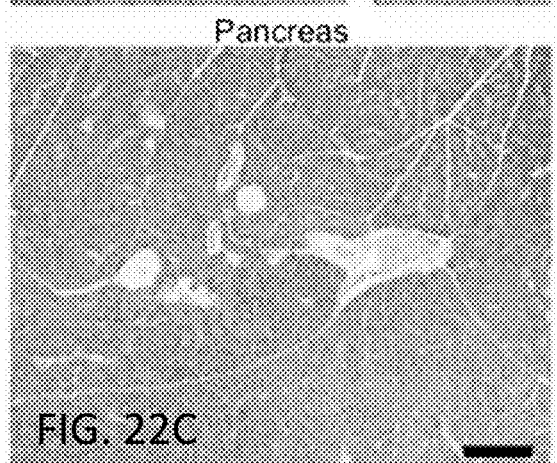
Figure 22D:
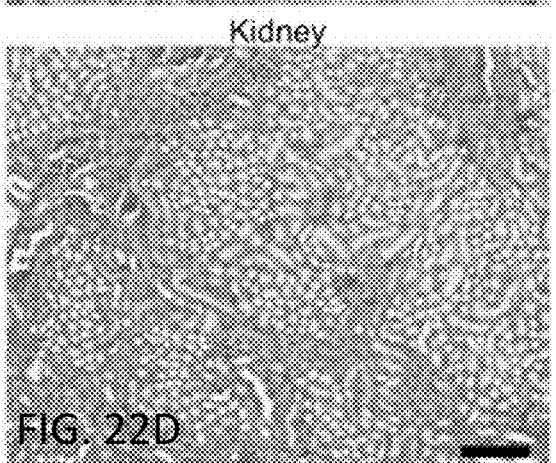
Figure 22E:
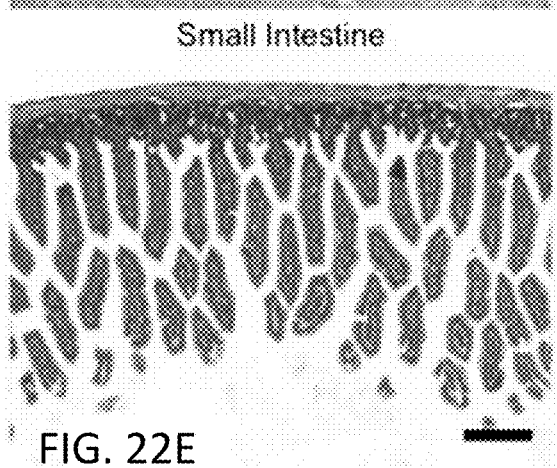
Figure 22F:
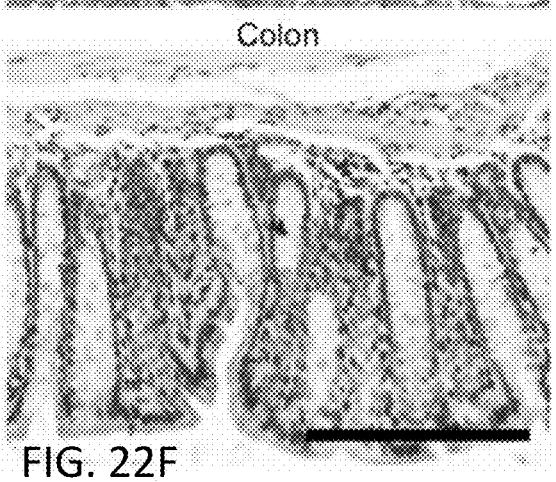

Total Fecal scores for healthy animals receiving treatment were also normal. Specifically, a paired, two-tailed t-test between the Probe Insertion and ultrasound groups showed no significant difference between their scores on any day. The largest standard deviation observed in the total fecal score for the Control, Probe Insertion, and US groups over the 14-day trial is 0.54, 2.68, and 3.28, respectively. The average standard deviation for each group over the 14-day trial is 0.17, 0.99, and 1.56, respectively. FIG. 20 is a graph illustrating the effect of rectal ultrasound on fecal score according to some embodiments.

The tolerability of treatment was further corroborated with the quantification of cytokines in colonic tissue. Cytokine levels known to be enhanced as a result of acute inflammation were profiled from colonic tissue. To further evaluate potential toxicity resulting from UMGID alone, cytokine expression including TNF-$\alpha$, IFN-$\gamma$, IL-6, and IL-17 was performed from colonic tissue from all three groups. FIGS. 21A-21D are graphs illustrating the effect of rectal ultrasound on cytokine presentation (n=4 biological repeats for all groups) according to some embodiments. In particular, FIG. 21A illustrates cytokine levels of TNF-$\alpha$, FIG. 21B illustrates cytokine levels of IFN-$\gamma$, FIG. 21C illustrates cytokine levels of IL-6, and FIG. 21D illustrates cytokine levels of IL-17. Counts were assessed using the Mouse Inflammatory Panel (available from nanoString Technologies, Seattle, Wash.), which physically counts the number of mRNA strands present in the sample and normalizes these counts across samples using internal positive spike-in controls. All graphs represent averages and standard deviations. Sample sizes indicated are biological replicates. No statistical difference was found in expression levels of the proinflammatory cytokines TNF-$\alpha$, IFN-$\gamma$, IL-6, or IL-17 between treatment groups (one-way analysis of variance testing with multiple comparisons). Toxicity as evaluated through the absence of anemia, low fecal score, low histology scores, and normal cytokine levels supports the likely safety of this drug delivery modality in the GI tract.

To assess the potential for cavitation occurring in other parts of the body, histological examination was made on liver, spleen, pancrease, kidney, small intestine, and colon in healthy animals receiving insertion of the probe or insertion of the probe followed by sonication. Blinded evaluation of the histology by a clinical pathologist determined the tissue beyond the colon to be of normal architecture with no cytologic abnormality in all groups. Only in the group receiving insertion of the probe and sonication was there minor disruption of the colon only. The histology score for colonic tissue for these animals was statistically better than the score observed for any group that had colitis induced. FIGS. 22A-22F are representative histological images of mouse liver, spleen, pancreas, kidney, small intestine, and colon, respectively, after a 14 day treatment regimen of either no treatment (n=5), insertion of the probe without turning it on (n=5), or insertion of the probe and sonication (n=5). The scale bar represents 200 $\mu$m.

The minimal toxicity as evaluated through the absence of anemia, low fecal score, low histology scores, and normal cytokine levels supports the likely safety of this drug delivery modality in the GI tract.

As shown in FIG. 18B, colitis was induced with 3% w/w DSS given ad libitum for seven days with concurrent treatment administration starting on day 2. Administration of mesalamine in combination with QD ultrasound treatments, as well as every other day (QOD), enabled significantly faster recovery from colitis symptoms compared to daily administration of a mesalamine enema alone (the current standard-of-care), as assessed by the total fecal score. Specifically, both groups receiving ultrasound treatments demonstrated improved total fecal scores when compared to the disease group and enema group from day 12 on (one-way ANOVA with multiple comparisons, P<0.047) and demonstrated total fecal scores below 4 on day 14. This is in contrast to both disease groups receiving no treatment and those receiving mesalamine enemas alone QD, which still demonstrated significantly elevated total fecal scores on day 14.

Figures 23A, 23B:
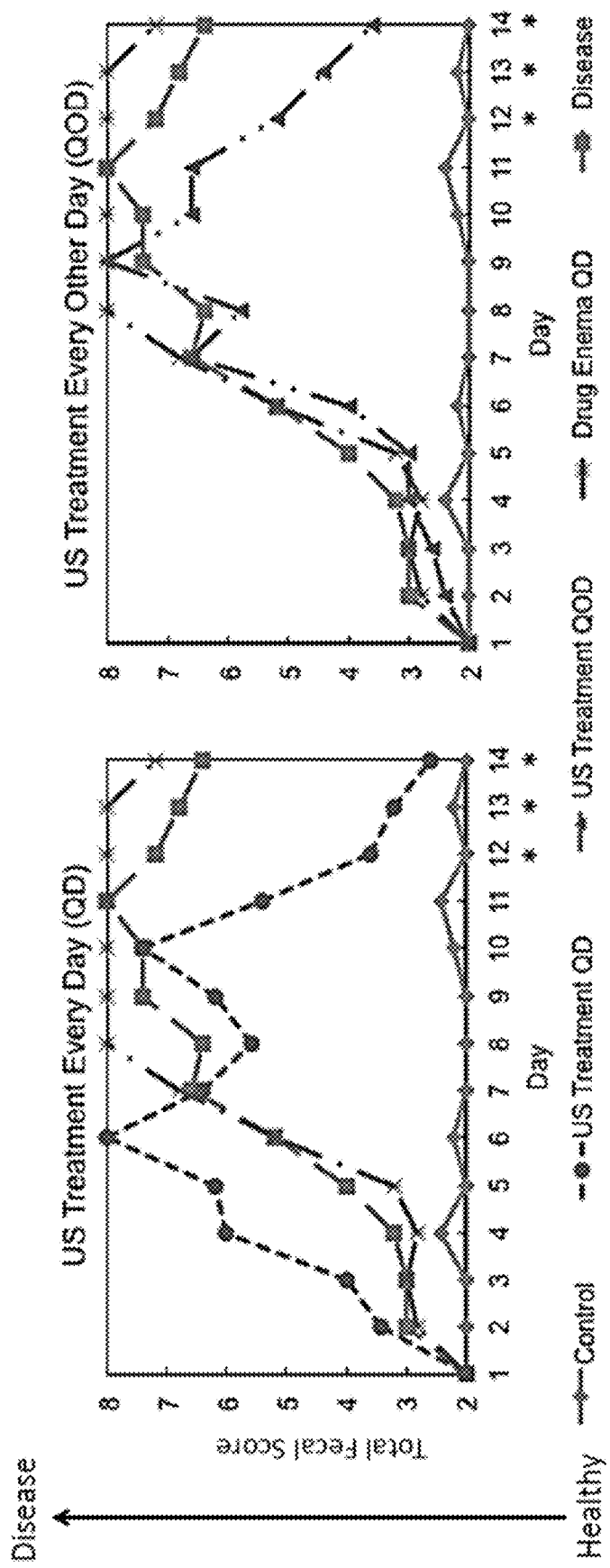
FIGS. 23A-23B are graphs illustrating effects of ultrasound on total fecal scores in accordance with some embodiments.

FIGS. 23A-23B are graphs illustrating Total Fecal Score for healthy animals (Control) and animals with DSS-induced colitis: receiving no treatment (Disease), receiving mesalamine enema daily (Drug Enema QD), receiving mesalamine enema with ultrasound treatment daily (US Treatment QD), and receiving mesalamine enema with ultrasound treatment every other day (US Treatment QOD) according to some embodiments. All groups were comprised of 5 animals. The asterisk (*) indicates a statistical difference between the ultrasound Treatment groups and those groups receiving no treatment or mesalamine enema alone (one-way analysis of variance testing with multiple comparisons, P<0.047).

Figure 24:
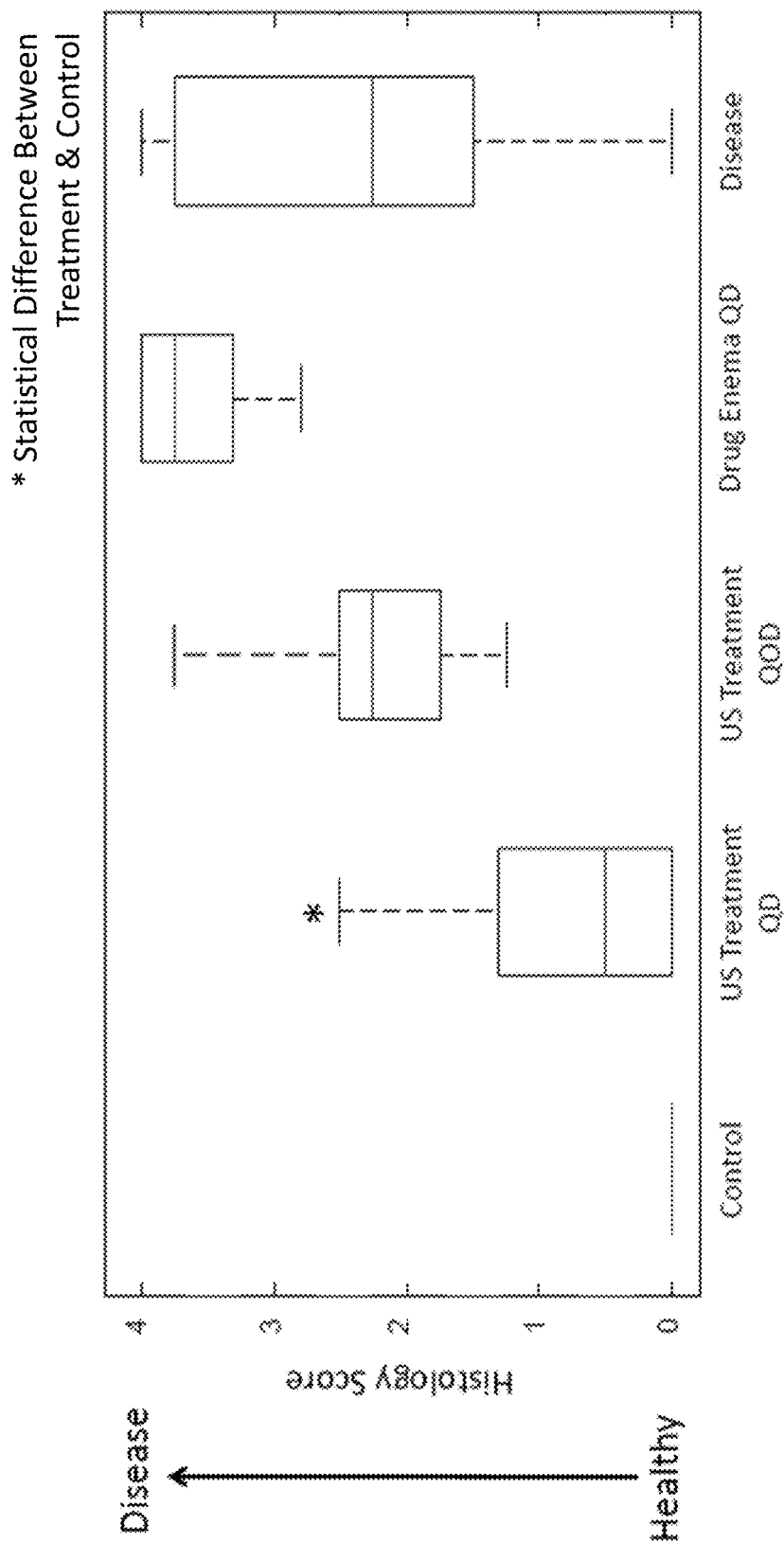
FIG. 24 is a graph illustrating effects of ultrasound on histology scores in accordance with some embodiments.

In addition to the total fecal score, colonic tissue was evaluated histologically at the end of the trial in a blinded fashion. FIG. 24 is a graph illustrating the histology scores of tissue sections at Day 14 according to some embodiments. The median, $25^{th}$, and $75^{th}$ percentiles are shown. The whiskers indicate the most extreme data points. The asterisk (*) indicates a statistical difference between the ultrasound QD group and all other colitis groups (one-way analysis of variance testing with multiple comparisons, $P<2.9\times10^{-4}$).

FIGS. 25A-25E are histological images of colonic tissue at Day 14 according to some embodiments. FIG. 25A is Score 0 (healthy tissue), FIG. 25B is Score 1, FIG. 25C is Score 2, FIG. 25D is Score 3, and FIG. 25E is Score 4 (diseased tissue). The scale bar for FIGS. 25A and 25E represents 500 μm. The scale bar for FIGS. 25B-25D represents 200 μm. The ultrasound Treatment QD group had a statistically lower histology score than any other treatment regimen and the disease group. The tissue in the ultrasound treatment QD group appeared to have significantly less erosion of the epithelium and only minor shortening of the crypts when compared to the other colitis groups.

C. Drug Mass Evaluation from Colonic Biopsies

Tissue was ground and mixed with phosphate buffered saline and precipitated with 10% trichloroacetic acid. The resulting supernatant was extracted with ethyl acetate. This extract was dried with anhydrous sodium sulfate, transferred to a glass tube, and evaporated to dryness under nitrogen. Then, the sample was reconstituted with toluene and derivatized with N,O-Bis(trimethylsilyl)trifluoroacetamide and trimethylchlorosilane (BSTFA+TMCS), 99:1 (available from Sigma Aldrich, Saint Louis, Mo.) and heated at 60° C. for 30 minutes. Finally, the sample was allowed to cool to room temperature and analyzed by GC/MS. An Agilent 5973 MSD/6890 Gas Chromatograph with a Rtx-5, 30 m×0.25 mm×0.1 μm column (available from Restek Corporation, Bellefonte, Pa.) was used for the analysis. This evaluation was performed by MPI Research Inc. (State College, Pa.) in a blinded fashion.

D. Insulin Delivery

In addition to the preparation noted above, a central venous catheter was placed in the femoral vein using the Seldinger technique to allow for frequent blood sampling. Before administration of insulin, 4 mL blood samples were drawn from the femoral vein to quantify the animal's initial blood-glucose levels. A real-time readout was achieved using a TRUEtrack® blood glucose meter (available from Nipro Diagnostics Inc., Fort Lauderdale, Fla.). The remaining blood sample was saved in a blood collection tube with sodium fluoride and ethylenediaminetetraacetic acid (EDTA) to minimize further glucose metabolism. All data shown represents the blood-glucose values quantified from the blood collection tubes, which was evaluated in a blinded fashion.

Once the rectum was cleared and the animal's base-line blood-glucose quantified, a 10 mL enema containing 100 units of NovoLog® rapid-acting insulin aspart (available from Novo Nordisk, Bagsvaerd, Denmark) was instilled in the colon and blood samples taken at approximately 2-minute intervals. The ultrasound treatment regimen was unchanged from that used for mesalamine testing. The blood-glucose was monitored for at least 40 minutes, depending on the experiment's effect on blood-glucose. When necessary, hypoglycemia was corrected with intravenous boluses of 50% dextrose (only needed when ultrasound treatment took place). The presented blood-glucose values are normalized by the animal's starting value, defined as the last blood-glucose value observed before administration of insulin. Each treatment regimen was repeated three times.

E. Dextran Sodium Sulfate-Induced Murine Colitis Model

Fifteen-week old, female C57BL/6 mice were purchased from Charles River Laboratories (Wilmington, Mass.) for the induction and treatment of dextran sodium sulfate (DSS)-induced colitis. Five animals were utilized per group. This was based on power calculations utilizing the results in pigs demonstrating an order-of-magnitude increase in drug delivery using ultrasound. Therefore, a similar improvement in stool score to that seen in prior experiments in rats with mesalamine administered at 3% and 30% were conservatively expected. Using a significance level of 0.05, a sample size of 5 animals per group achieves 90% power to detect the predicted difference of 4 in the stool score given the expected order-of-magnitude improvement in mesalamine delivery observed in the pig model. Each cage (group) was used as it was received and randomly assigned to experimental groups by the researchers performing the work. On day 1, blood was drawn from all mice and an initial weight of each animal was taken. Colitis was induced with 40-50 kDa dextran sulfate sodium salt (DSS) (available from, e.g., Affymetrix Inc., Santa Clara, Calif.). Starting on day 1, a 3% w/w DSS solution was administered in drinking water ad libitum. On days 3 and 5, the drinking solution was replaced with fresh DSS solution. On day 7, the DSS solution was removed and replaced with normal drinking water.

Treatment was administered starting on day 2. Treatment consisted of either a mesalamine enema alone or in combination with ultrasound. The enema consisted of mesalamine (66.6 mg/mL) in a 0.5% w/w carboxymethyl cellulose (available from, e.g., Sigma-Aldrich Saint Louis, Mo.) solution in PBS. Here, a custom-designed 40 kHz probe was fabricated to allow for insertion into the colon (Sonics and Materials, Inc., Newtown, Conn.). The shaft was 2 mm in diameter and contained two, 3 mm diameter protrusions at half-wavelength intervals to achieve radial ultrasound emission. The power of ultrasound treatment was calibrated to 4.0 W by calorimetry. The probe was inserted into the rectum and turned on for 0.5 seconds. The animals were monitored daily for weight, fecal consistency, and for the presence of fecal occult blood using Hemoccult cards (Beckman Coulter, Pasadena, Calif.).

Fecal consistency and the presence of blood was scored based on previously published protocols. Specifically, stool consistency was scored as follows: (1) normal pellet-like feces, (2) pellet of stool easily crushed, (3) soft, watery stool with granules present, or (4) diarrhea. The presence of blood was confirmed by hemoccult testing daily. Animals with negative hemoccult results were scored (1). Positive hemoccult results were further stratified as follows: (2) feces with discrete blood speckles on the surface, (3) feces stained with blood, or (4) feces completely covered with blood or the presence of blood staining around the anus. The total fecal score was the summation of the consistency and blood score. Therefore, the total fecal score ranged from 2-8. If feces could not be collected on an individual day, that animal was assigned a total fecal score of 8.

On day 14, a final weight was taken and fecal score assessed. Blood was taken, and the animal euthanized. Immediately after euthanasia, the colon was dissected out and imaged macroscopically. It was then fixed in 10% formalin. Once fixed, the colon was sectioned into 2-6 pieces and mounted in paraffin. Two, 8 µm sections were taken from each paraffin block separated by a 200 µm step. The sections were stained with hematoxylin and eosin and mounted on glass microscope slides.

Histological examination was performed by a clinical pathologist at the Massachusetts General Hospital in a single-blinded fashion. Scores were determined according to previously published protocols with slight modification as follows in TABLE 3:

| Score | Description |
|---|---|
| 0 | Normal colonic mucosa with preservation of normal crypt architecture. |
| 1 | Shortening of the crypts with moderate chronic inflammatory infiltrate above the muscularis mucosae. |
| 2 | Base of the mucosa effaced but residual surface epithelium and upper portion of the crypt preserved. |
| 3 | Complete effacement of the mucosa with chronic inflammation of the lamina propria and only residual surface epithelium present. |
| 4 | Complete effacement and erosion of the mucosal surface with fibrinopurulent debris present. |

Each tissue cross-section present on the microscope slide (n=2-6) was scored individually between 0-4 with a corresponding percentage involvement (rounded to the nearest quartile). The resulting score for each cross section examined for every animal in a given study group was then averaged to determine the histology score for that study group.

A separate cohort of animals that did not have disease induced were used to test the safety and tolerability of ultrasound in the rectum. The effect of insertion of the probe into the rectum (n=5), and insertion of the probe followed by sonication (n=5) were tested in healthy animals to assess any potential negative effects of the treatment alone. Probe insertion and sonication was administered daily using the same QD treatment regimen detailed above, and visually depicted in FIG. 18B. These groups were compared to a control group that received no treatment (n=5). The total fecal score was assessed daily and hematocrit and hemoglobin were quantified on day 1 and day 14. On day 14, the animals were euthanized and the liver, spleen, pancreas, kidney, small intestine, and colon were carefully dissected, fixed in formalin, mounted in paraffin, and sectioned and stained as described above. Additionally, a separate colonic tissue sample was saved and immediately frozen at −80° C. for cytokine determination.

These tissue samples were processed to extract RNA. RNA was isolated using an Ambion Purelink RNA Mini Kit following the manufacturer's protocol. Concentration and quality of the resulting RNA were determined using a NanoDrop 2000 Spectrophotometer (Thermo Scientific, Waltham, Mass.). Cytokine mRNA was quantified using the Mouse Inflammatory Panel from nanoString Technologies (Seattle, Wash.) following the manufacturer's protocol. Specifically, 100 ng of total RNA of each sample was added to a distinct sample well supplied by the manufacturer. Then, 600 fields of view were automatically imaged and counted by the nCounter® Digital Analyzer (NanoString Technologies Inc., Seattle, Wash.) to determine the number of molecules present for each gene. Counts for each sample were automatically normalized by the equipment utilizing the built-in positive spike-in controls.

Statistical analysis for the in vitro and in vivo porcine work was performed using two-tailed Student's t-tests to determine statistical significance. Statistical analysis for the in vivo mouse work was performed using one-way analysis-of-variance (ANOVA) tests with multiple comparisons. Confidence intervals for regression slopes were constructed using normal-based 95% confidence intervals. No samples were excluded from analysis in this study. Statistical significance was defined throughout as $P<0.05$. All calculations were performed using MatLab® R2014a software (available from MathWorks, Natick, Mass.).

EXAMPLE 5: DEVICES FOR ULTRASOUND ENHANCED DELIVERY

Figure 26:
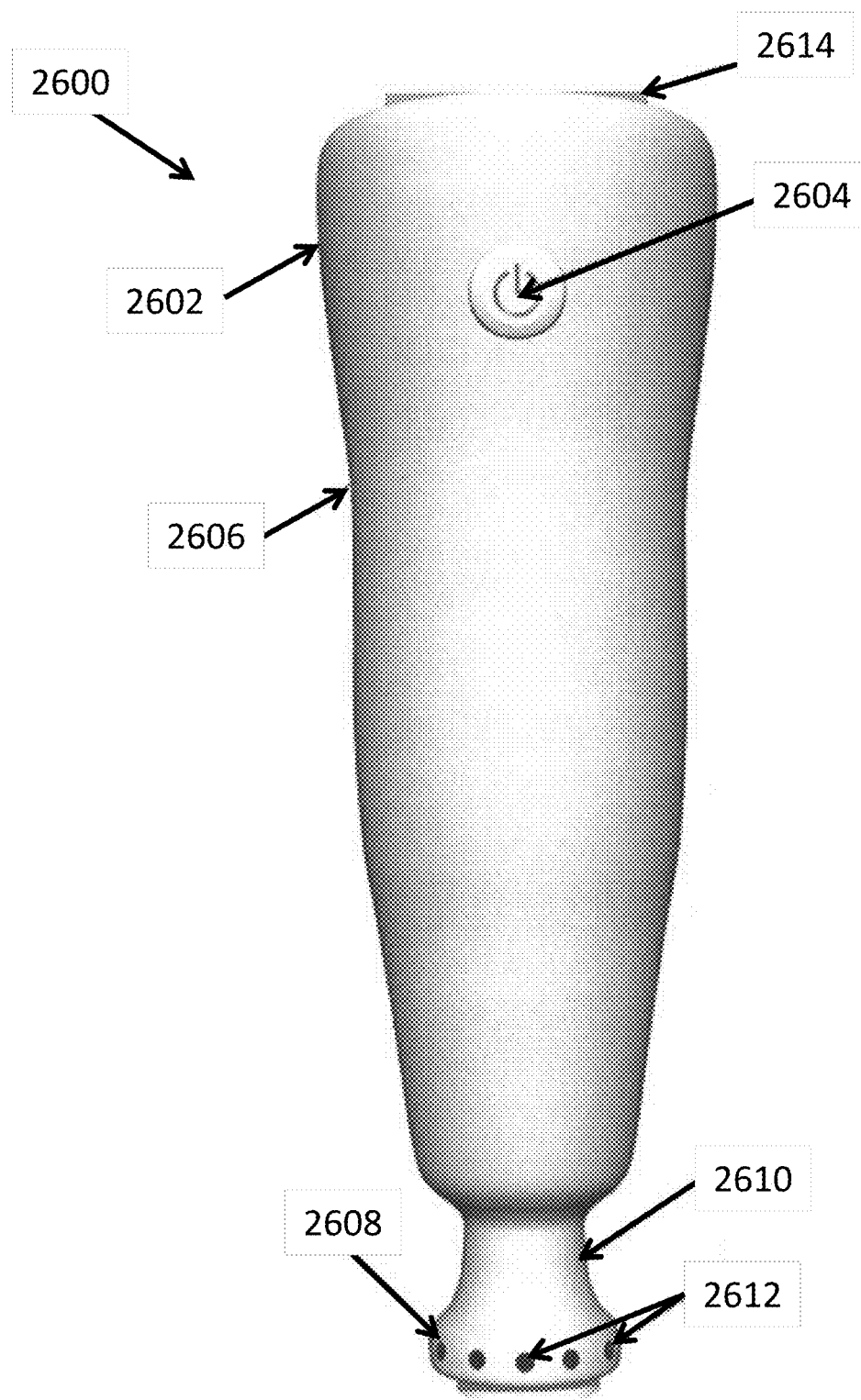
FIG. 26 is a schematic illustrating a handheld ultrasound-emitting drug delivery device in accordance with some embodiments.

FIG. 26 is a side view of a reusable hand-held, ultrasound emitting drug delivery device 2600 for (self-)administration of a medicated solution into the colon according to some embodiments. The device 2600 includes a housing 2602, which may be cylindrical in shape with a taper down the length of the device. The housing 2602 may include or define a power control (e.g., a button or switch) 2604 to turn the device to be on or off. The housing may include a concave region 2606 that supports holding, positioning, and/or gripping the device by a user. The power control 2604 and concave region 2606 may be located toward the proximal end of the device, whereas the opposite distal end includes a tip 2608 for insertion into the colon. The proximal base of the tip 2608 may include a concave region 2610 for creating a seal around the tip 2608 and the rectum. The tip 2608 may define at least one opening 2612 for delivering a substance from inside the device. The at least one opening 2612 may be oriented radially (as shown in FIG. 26) or axially to device 2600.

Figure 27:
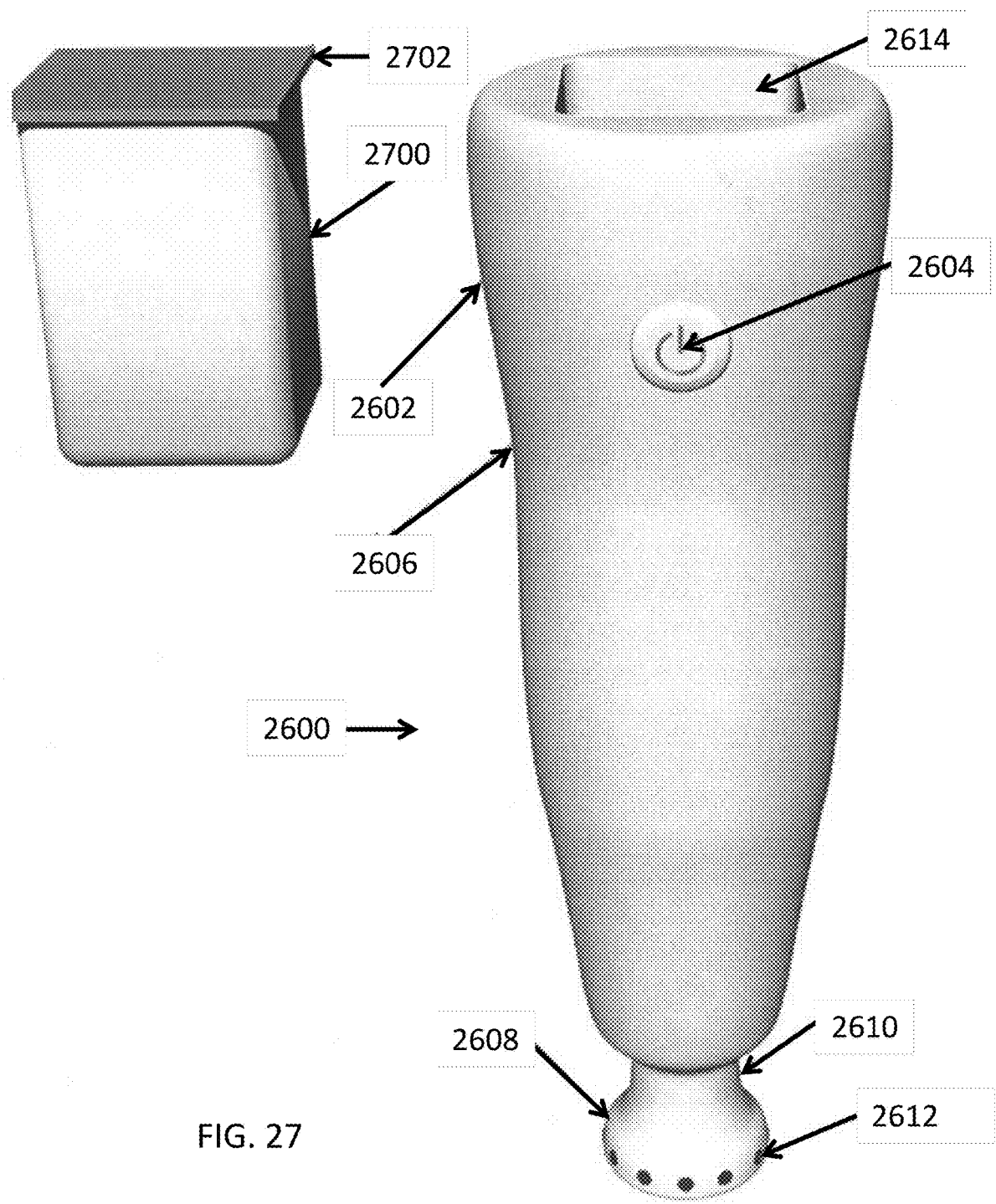
FIG. 27 is a schematic illustrating a handheld ultrasound-emitting drug delivery device and a drug cartridge in accordance with some embodiments.
Figure 28:
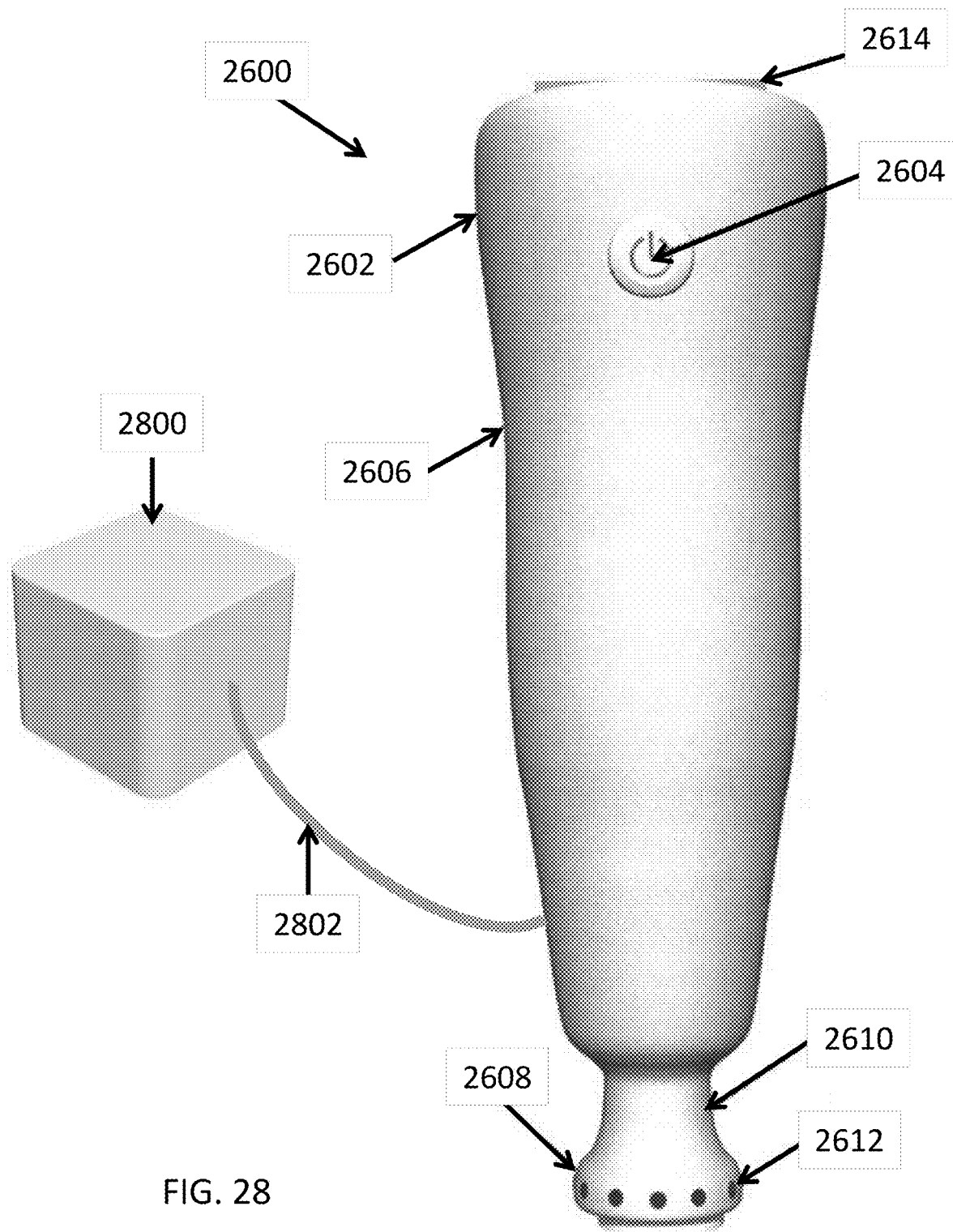
FIG. 28 is a schematic illustrating a handheld ultrasound-emitting drug delivery device and an exterior drug reservoir in accordance with some embodiments.

Device 2600 also may define a port 2614 for receiving a cartridge containing a substance for delivery from the device. FIG. 27 illustrates such a cartridge 2700, which may be replaceable. The cartridge 2700 may have a top ridge 2702 to allow for the cartridge to remain in place once inserted into the device. Alternatively or in addition to a cartridge, device 2600 may receive the substance from an exterior container 2800, which may be compressible, thereby allowing the user to manually expel the substance by compressing the container 2800. The container 2800 may be connected to the device 2600 with, for example, flexible tubing 2802.

The housing of the device, excluding the tip, may include a rubberized coating or material that allows the user to hold the device securely. The tip may include a frictionless or low friction coating or material that allows for smooth insertion of the tip into the rectum. In some embodiments, the housing and/or tip is water resistant or waterproof for cleaning. The dimensions of the device include a length of about 14 cm to about 40 cm, a diameter of about 4 cm to about 6 cm at the top of the device, and a diameter of about 1 cm to about 3 cm at the tip of the device.

Figure 29:
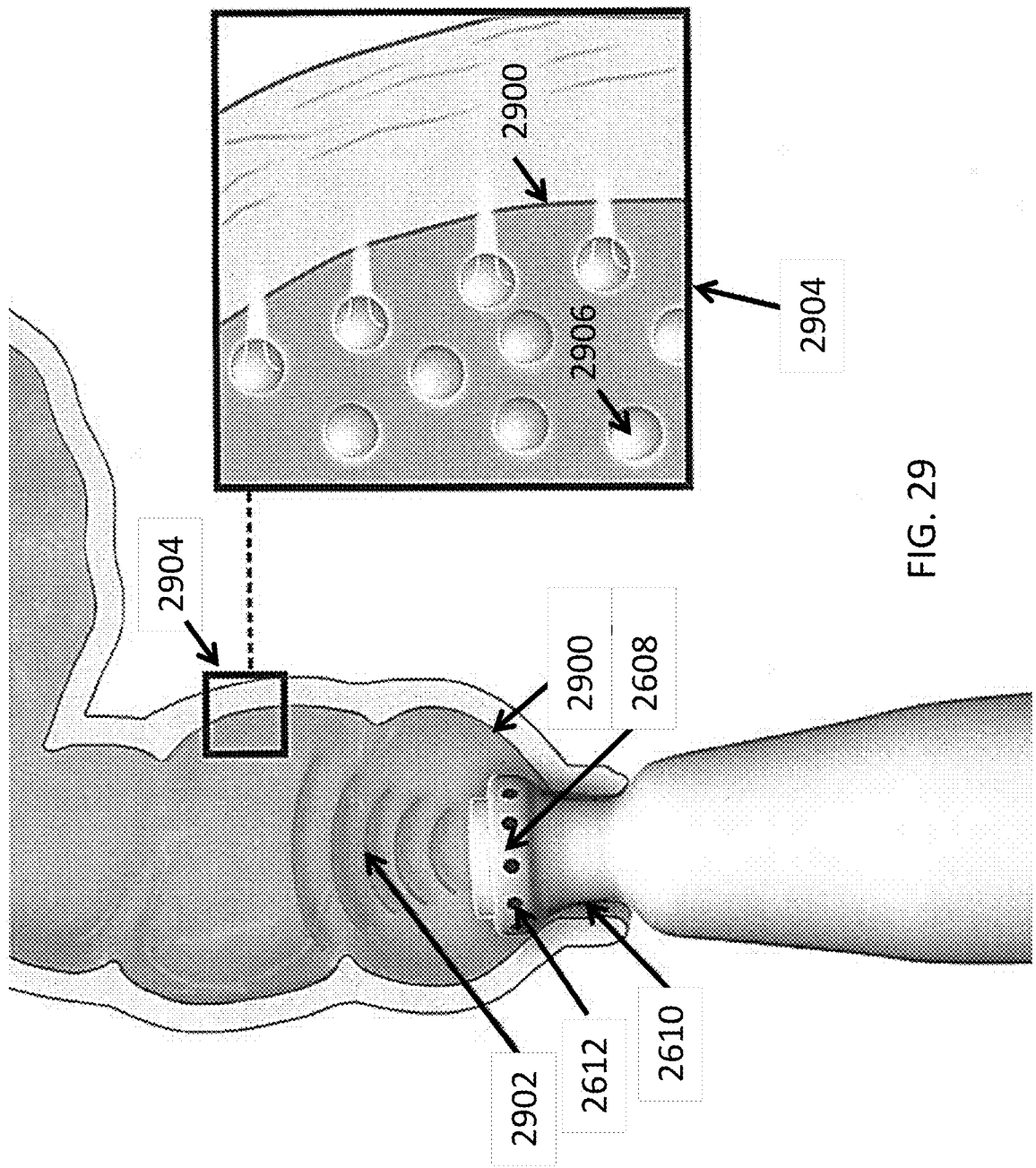
FIG. 29 is a schematic illustrating use of a handheld ultrasound-emitting drug delivery device in accordance with some embodiments.

FIG. 29 is a diagram illustrating use of device 2600 according to some embodiments. Tip 2608 of device 2600 has been inserted into an intestine 2900 such that the concave region 2610 forms a seal with the rectum and openings 2612 are in fluid communication with the colon. Once device 2600 is activated, low frequency ultrasound 2902 is emitted from the tip 2608, maximizing radial emission. As shown in magnified box 2904, the low frequency emission 2902 allows for delivery of the substance 2906 released from the openings 2612 into the intestine such that it penetrates the intestinal epithelium 2900.

Figure 30:
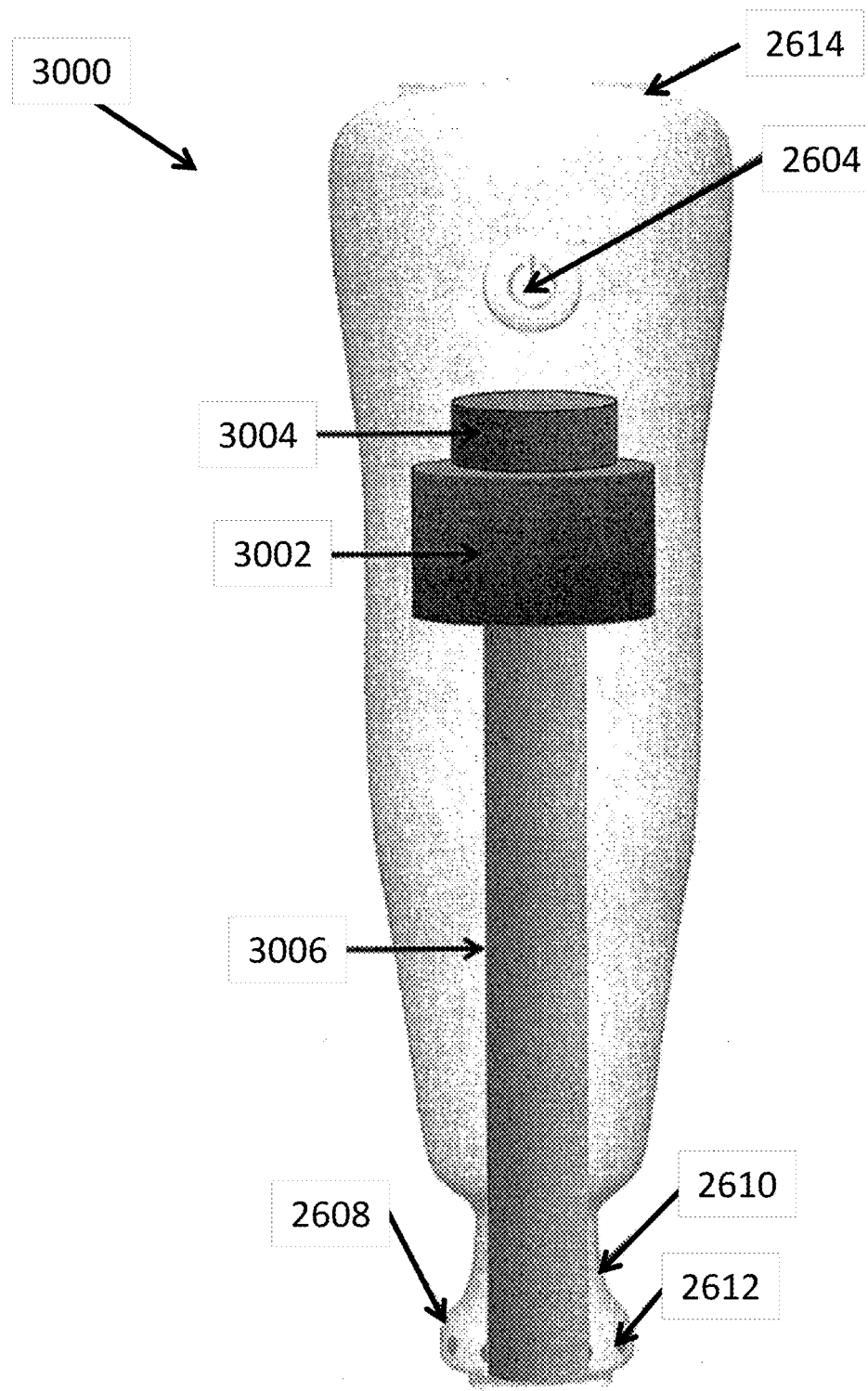
FIG. 30 is a schematic illustrating a handheld ultrasound-emitting drug delivery device with a balanced piezoelectric crystal in accordance with some embodiments.
Figure 31:
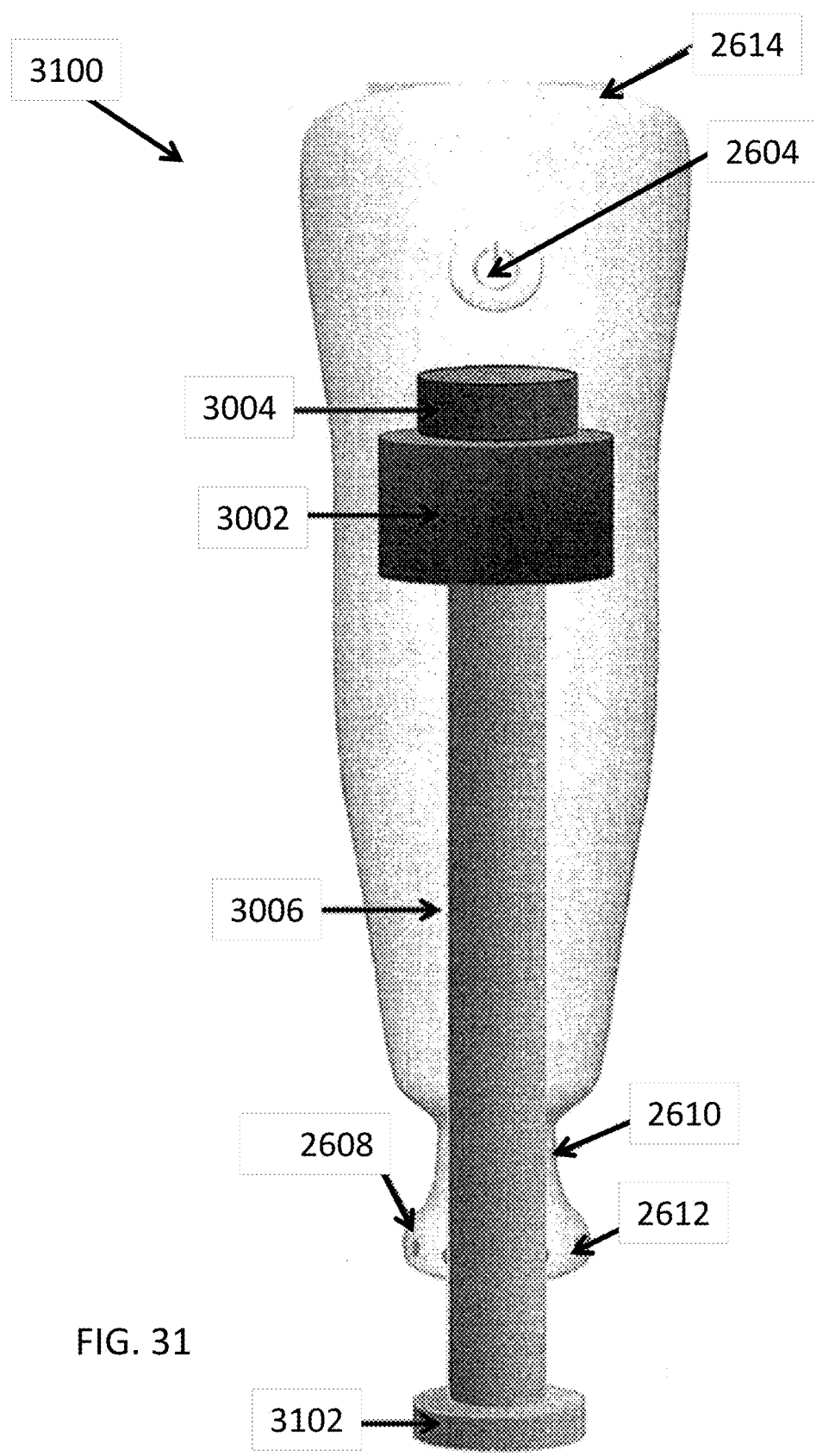
FIG. 31 is a schematic illustrating a handheld ultrasound-emitting drug delivery device with an oscillating shaft having a protrusion in accordance with some embodiments.

FIG. 30 shows the ultrasound mechanism of a device 3000 according to some embodiments. Device 3000 emits ultrasound using a balanced piezoelectric crystal 3002 (with a backing 3004 for crystal balancing) connected to an oscillating shaft 3006. The piezoelectric crystal 3002 expands and contracts, making the shaft 3006 oscillate at ultrasonic frequencies. The piezoelectric crystal 3002 may be lead zirconate titanate (PZT), quartz, or ceramic. Ideally, the piezoelectric crystal 3002 has a high electrical-to-mechanical conversion efficiency and low thermal output. The ultrasound frequency emitted from the tip 2608 of the device 3000 may be from about 15 kHz to about 500 kHz or from about 500 kHz to about 3000 kHz. The length of the oscillating shaft 3006 may be from about 1 cm to about 7 cm, and the diameter of the oscillating shaft may be from about 0.1 cm to about 2.0 cm. FIG. 31 shows the ultrasound mechanism of a device 3100 according to another embodiment, in which the oscillating shaft 3006 has a protrusion 3102. One or more protrusions 3102 may be positioned along the shaft 3006 and utilized to maximize radial emission. The diameter of a protrusion 3102 may be less than about 1.0 cm beyond the diameter of the oscillating shaft 3006.

Figure 32:
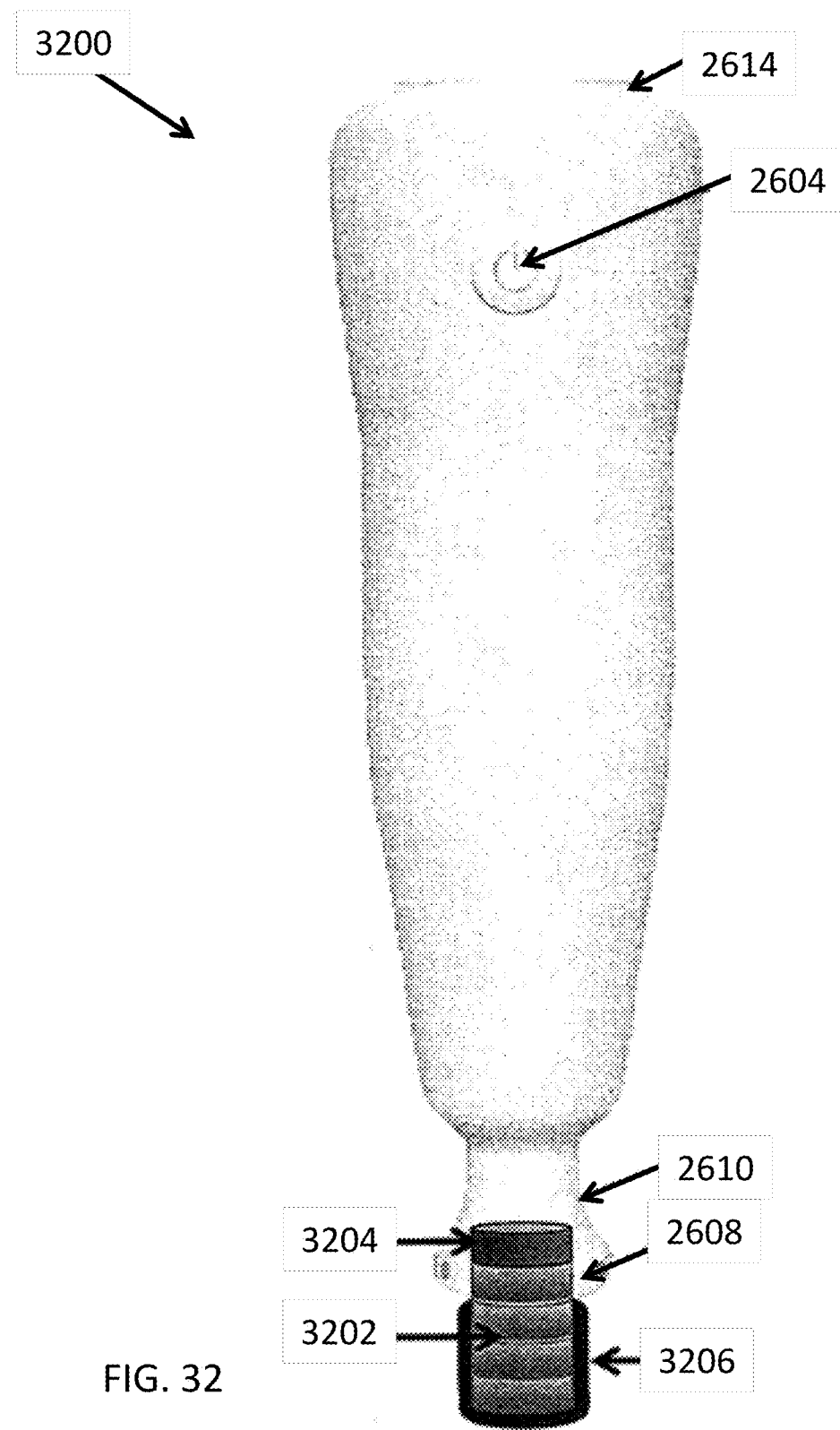
FIG. 32 is a schematic illustrating a handheld ultrasound-emitting drug delivery device with high aspect-ratio crystals in accordance with some embodiments.

FIG. 32 shows the ultrasound mechanism of a device 3200 according to some embodiments. Device 3200 emits ultrasound using a high aspect-ratio stack of circular piezoelectric crystals 3202 (with a backing support plate 3204) built directly into the insertion tip 2608. The crystals may be coated with a waterproof and/or acoustically transparent material 3206 to conduct radial ultrasound emission.

Figure 33:
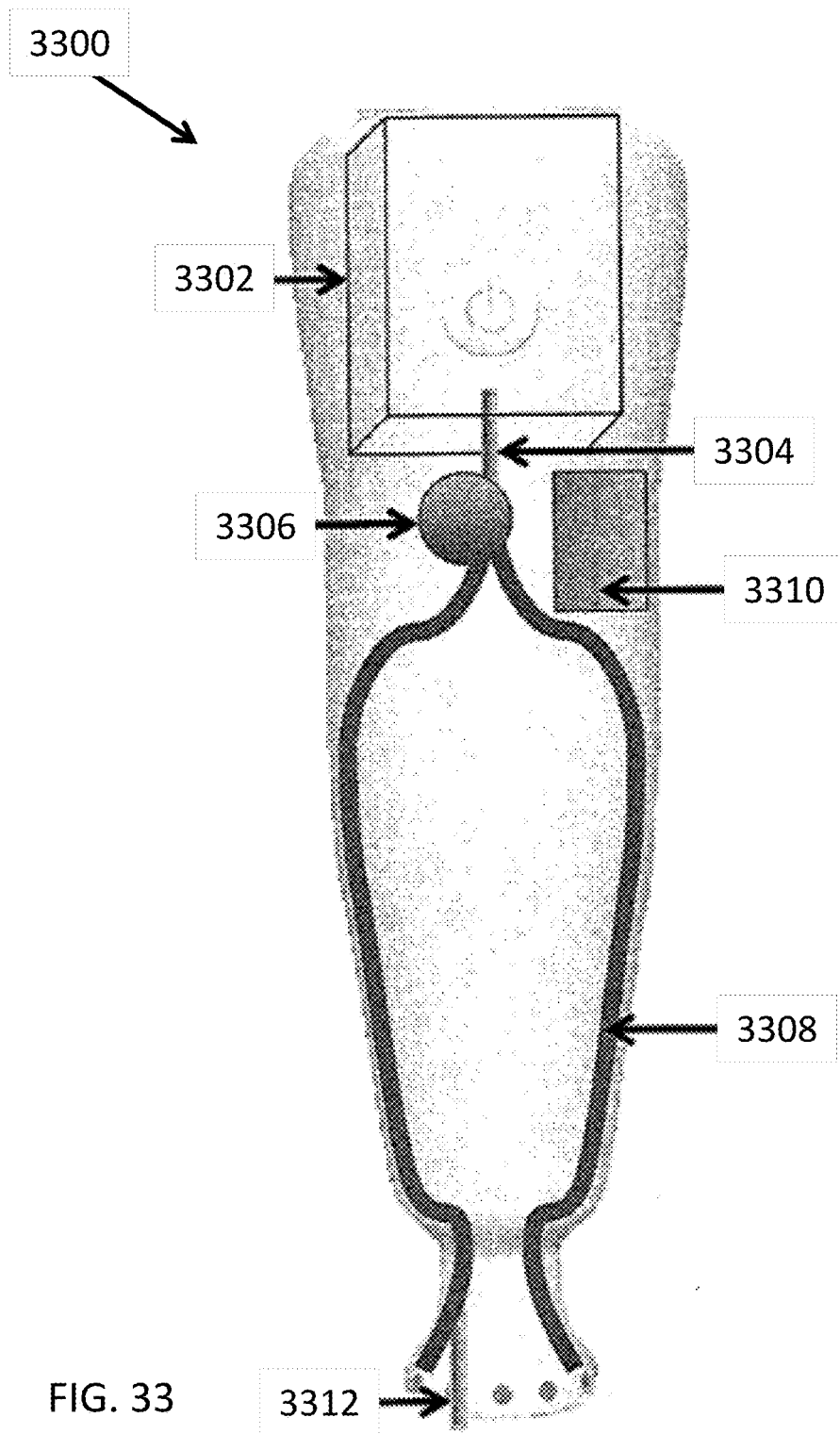
FIG. 33 is a schematic illustrating internal components of a handheld ultrasound-emitting drug delivery device in accordance with some embodiments.
Figure 34:
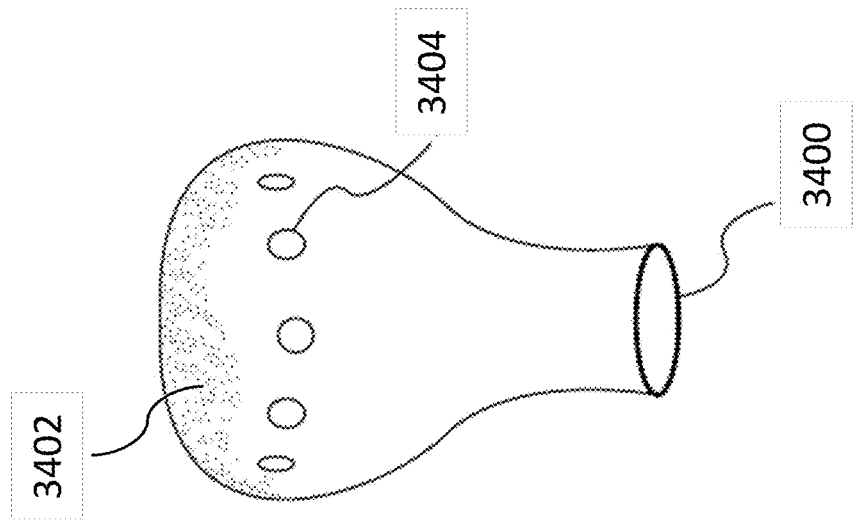
FIG. 34 is a schematic illustrating a banded sheath for a handheld ultrasound-emitting drug delivery device in accordance with some embodiments.
Figure 35B:
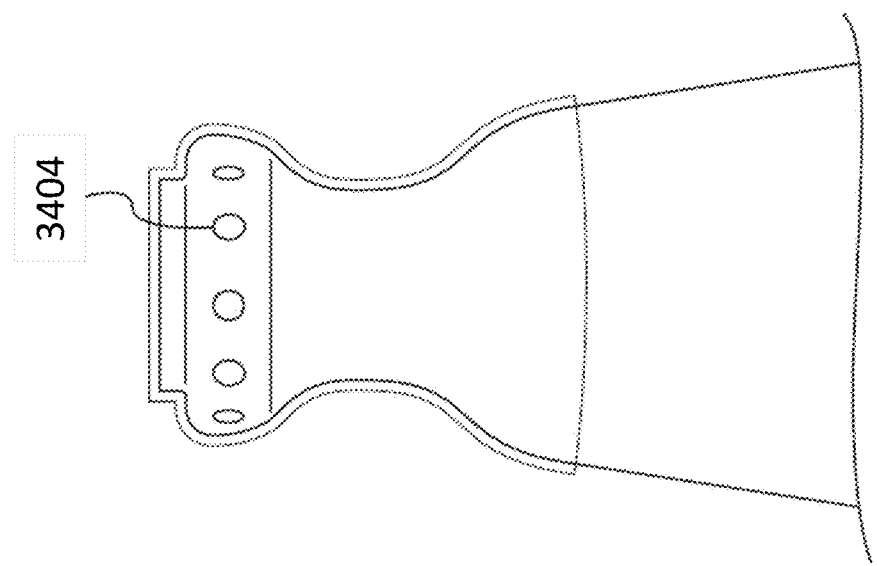
FIGS. 35A and 35B are schematics illustrating a stretchable sheath for a handheld ultrasound-emitting drug delivery device in accordance with some embodiments.
Figure 35A:
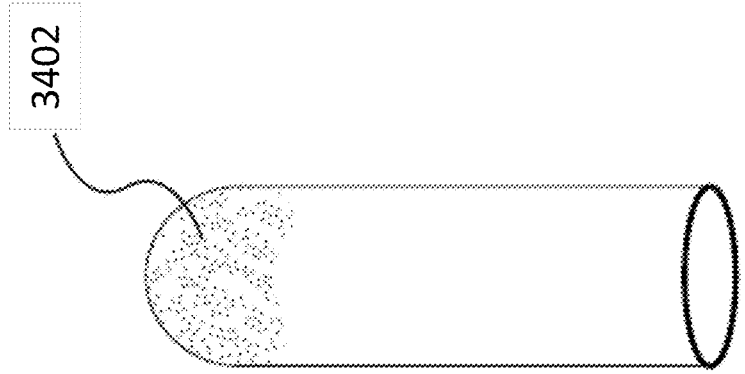

FIG. 33 shows the internal components of a device 3300 according to some embodiments. Device 3300 includes a port or reservoir 3302 for receiving a cartridge with the substance or the substance itself. A conduit (e.g., a needle) 3304 is used to establish fluid communication with the substance in the cartridge/reservoir. Device 3300 may have a pump 3306 that drives the substance from the cartridge/reservoir to the distal end of the device via one or more fluid channels 3308 for elution from the at least one opening in the tip. Device 3300 may include a battery 3310 to power the internal components and/or a thermocouple 3312 at the distal end to provide real time monitoring of heat.

Figure 37B:
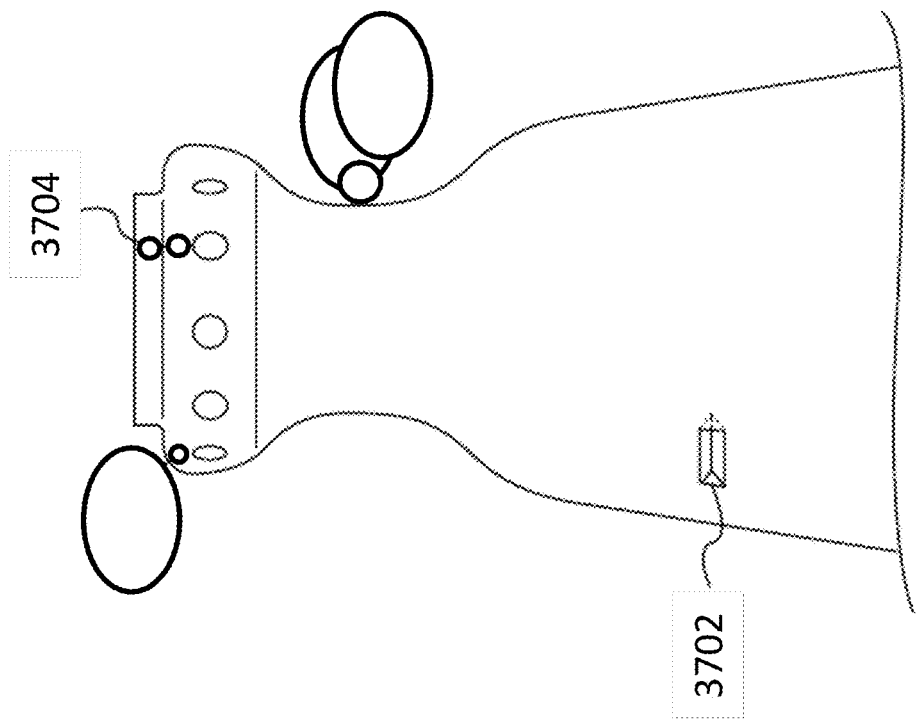
FIGS. 37A and 37B are schematics illustrating a securing mechanism for a sheath for a handheld ultrasound-emitting drug delivery device in accordance with some embodiments.
Figure 37A:
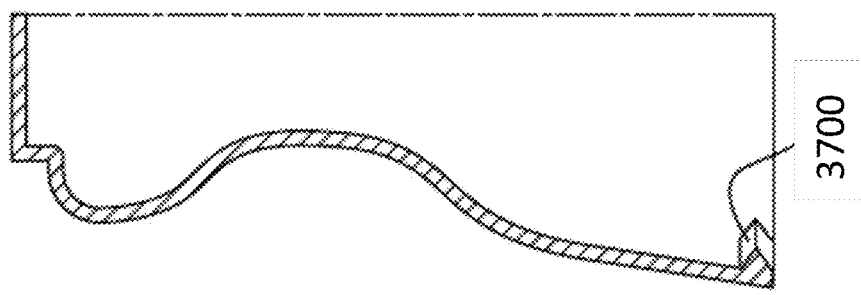

The device may be designed to allow for a fast evacuation of the substance, for example, in less than about 20 seconds. The tip may define angled openings that allow the substance to be sprayed from the tip allowing for maximal coating of the tissue with the substance. The openings may be angled from about 45° to about 90° relative to the circumferential ultrasound tip to allow the substance to be sprayed or vortexed which allows for radial covering of the substance to the tissue. In an alternative embodiment, the substance may be eluted through the center of the ultrasound emission shaft, allowing atomizing and spraying of the substance.

A device tip may include the ultrasound emission shaft or crystal stack, at least one eluting opening, and/or a thermocouple for real-time monitoring of heat. The length of the tip may be from about 1 cm to about 10 cm; the radius may be from about 1 cm to about 3 cm. The tip may be fixed or removable to allow for interchangeable tips to allow for treatment of various conditions, and anatomical locations, particularly mucosal tissue. Anatomical locations for use of the device may include, but are not limited to, the rectum, the vagina, the ear, the nose, and the oral cavity (e.g., mouth, cheek, or tongue).

The tip of the device can be covered with a sheath to protect the tip from direct contact with anal tissue and fecal matter. FIGS. 34, 35A, 35B, and 36A-36C are views of different sheathes according to some embodiments. The sheath may be washable or disposable. A sheath may cover the entire portion of the device that is inserted in the body. The material of the sheath may be acoustically transparent/conducting (i.e., does not allow for attenuation of the ultrasound signal). The material of the sheath may be frictionless or low friction to allow easy insertion and removal of the device from the body.

In some embodiments, as shown in FIG. 34, the proximal end of a sheath includes a band (e.g., elastic) 3400 to seal around the probe tip. The opposite distal end of the sheath may include a gel or liquid 3402, and the distal end of the sheath may define at least one perforation 3404 to line up with the at least one opening in the tip. The gel or liquid 3402 allows for adequate conductance of the ultrasound signal from the tip emitter through the sheath. In other embodiments, a sheath (e.g., with elastic properties) stretches to wrap around and/or over a probe tip. The pre-installed sheath as shown in FIG. 35A allows for a tight seal around all portions of the probe tip when stretched over the probe tip as shown in FIG. 35B.

A sheath may have visual indicators to aid the patient in aligning at least one perforation 3404 with at least one opening in the tip. Alternatively, upon elution of the substance from the device, the sheath may be punctured by and where the substance is eluted from the device.

FIG. 36A is a side view of a sheath 3600 made of a rigid material (e.g., hard-plastic) that closely conforms to the tip shape and defines at least one perforation 3404 to line up with the at least one opening in the tip. The sheath may have ultrasound transparent/conducting properties and dimensions to allow for coverage of the entire inserted tip. A gel or liquid 3402 may be included for adequate conductance of the ultrasound signal from the tip emitter through the sheath. FIG. 36B shows a rigid sheath comprising at least two separate pieces which fasten together around and/or over the tip of the device. Alternatively, the two separate pieces may be initially connected at one end (e.g., by a hinge mechanism 3600 that allows for the two pieces of the sheath to click and fasten around the probe tip) as shown in FIG. 36C. FIG. 37A is a cross-sectional side view of at least part of a sheath to illustrate wall thickness according to some embodiments.

The inner wall of the sheath includes a hook, latch, and/or other securing mechanism 3700 configured to line up with a receiving indent or other securing mechanism 3702 on the body of the probe device 3704 as shown in FIG. 37B in accordance with some embodiments.

EXAMPLE 6: DELIVERY OF NUCLEIC ACIDS

Some embodiments may be used to deliver nucleic acids, such as a synthetic RNA duplex designed to specifically target a particular mRNA for degradation (an siRNA). Delivery of an siRNA (unencapsulated) against the cell signaling protein tumor necrosis factor alpha (TNF-α) was tested in a dextran sodium sulfate (DSS) colitis model in accordance with some embodiments. FIG. 38A is a diagram illustrating the treatment regimen according to some embodiments. Less than 200 ng of unencapsulated siRNA (compared to thousands of nanograms of encapsulated siRNA) was administered via the rectum. FIG. 38B is bar graph illustrating the effect of ultrasound and siRNA delivery (versus only siRNA delivery) on total fecal scores according to some embodiments. The siRNA was effectively delivered by ultrasound, indicating superior clinical value.

Figure 39A:
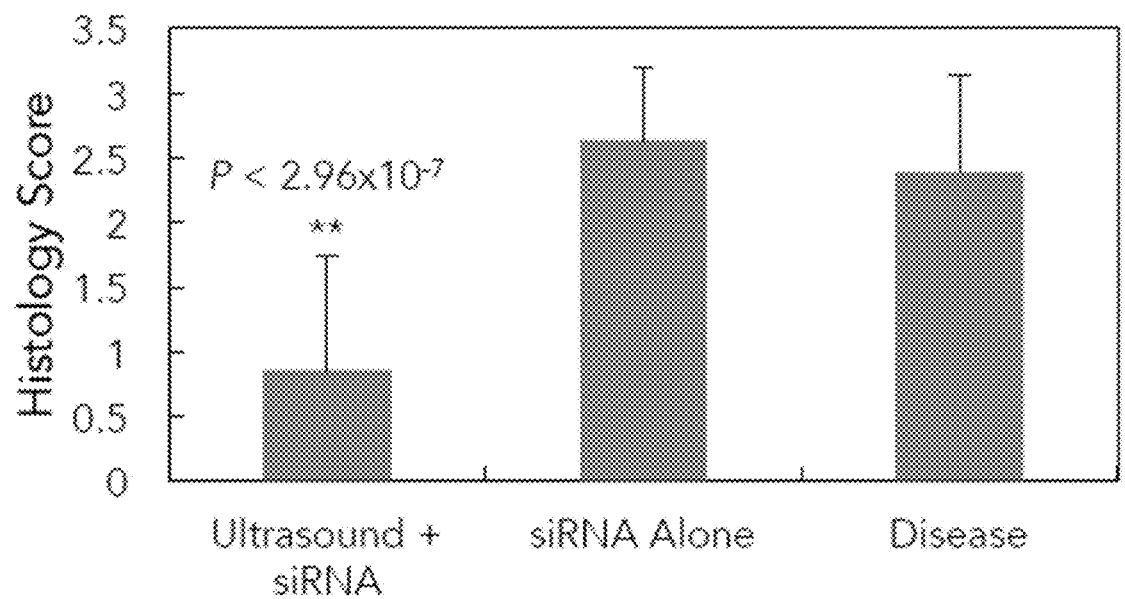
FIGS. 39A and 39B are images for illustrating histology scoring.
Figures 39B, 39C:
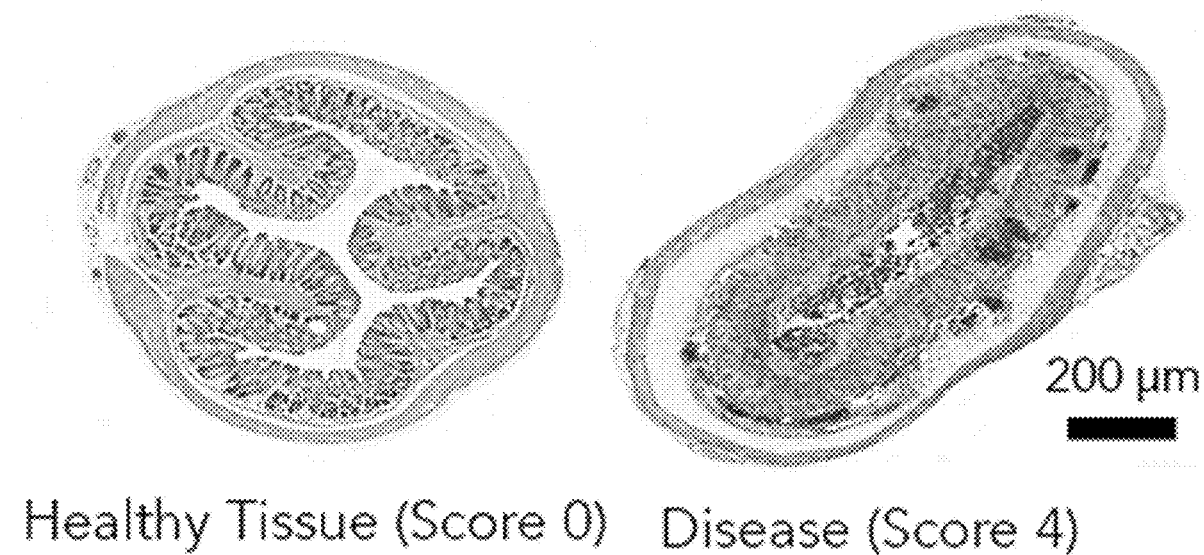
FIG. 39C is a bar graph illustrating effects of ultrasound for nucleic acid delivery on histology scores in accordance with some embodiments.

Histology was reviewed in a blinded fashion by a clinical pathologist according to metrics similar to those described above. FIG. 39A is a histology image of healthy tissue (Score 0), and FIG. 39B is a histology image of disease tissue (Score 4). FIG. 39C is a bar graph illustrating the histology scores, which were significantly better for animals receiving the siRNA and ultrasound.

This study demonstrates successful delivery of nucleic acids with therapeutic relevance. Nucleic acid sequences may be designed for greater synergy with ultrasound. That is, particular nucleic acid sequences may experience greater enhancement as a result of ultrasound. Whereas current methods require formulation of potential drug candidates to enable their delivery for further assessment, which is very difficult, this technology may be used to screen drug candidates via delivery of complex molecules without any formulation.

EXAMPLE 7: ULTRASOUND-MEDIATED VACCINATION

Immune response may be biased based on the route of antigen administration. For example, vaccination at mucosal surfaces against diseases which infect mucosal surfaces may be beneficial, and ultrasound may preferentially increase immune response in accordance with some embodiments.

Vaccination against infection by *Clostridium difficile* (*C. diff*) was tested according to some embodiments. A germ that spreads through feces, *C. diff* is a model candidate for this study. *C. diff* infections are common in hospitals and have a high rate of recurrence. After antibiotics wipe out natural flora in the gut, *C. diff* colonizes the gut and secretes toxin A and B, which attacks the intestinal epithelium. Even stronger antibiotics are needed to treat *C. diff*, such as fidaxomicin, metronidazole, and vancomycin. Mice were vaccinated against infection by *C. diff* via the GI tract to bias immune response to secreted antibodies to prevent colonization according to some embodiments. Inactivated toxin A and B was used a model antigen.

Figure 40:
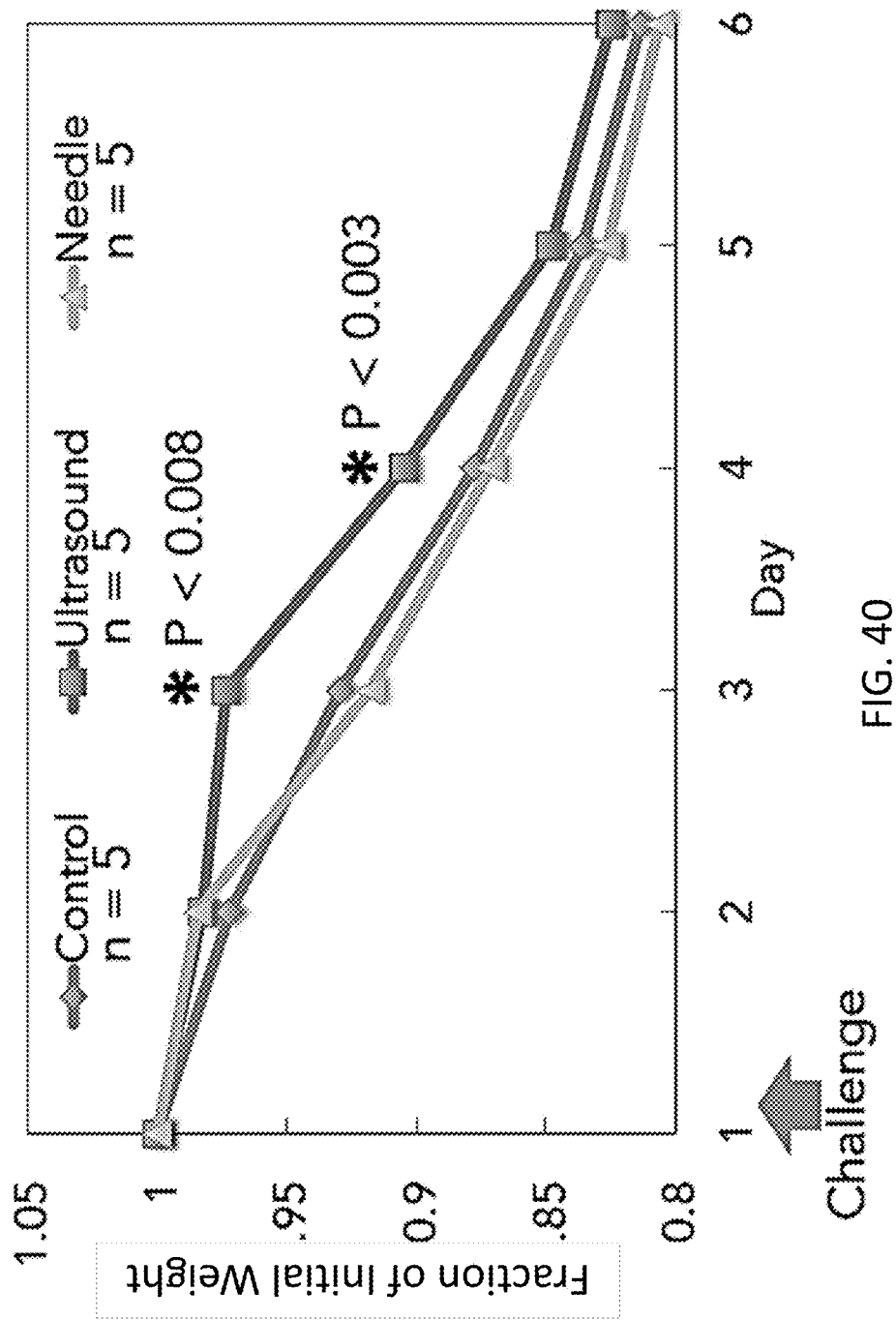
FIG. 40 is a plot illustrating effects of ultrasound-mediated vaccination on body scores in accordance with some embodiments.

The total protein content used for immunizations varies widely, but studies suggest relatively large doses of toxoid mixed with adjuvant. However, ultrasound-mediated GI vaccination used only 10 μg of total toxoid and no adjuvant for a treatment and two boosts. Blood and colonic lavage were collected after each vaccination. Animals were challenged with *C. diff* vegetative cells and toxin. Their health was monitored for weight loss and fecal consistency. FIG. 40 is a plot of relative weight for six days following the challenge according to some embodiments. The ultrasound-mediated GI vaccinated group (Ultrasound) showed statistically superior body scores through day 4 after the challenge over the Control group and a third group vaccinated via subcutaneous administration (Needle). Similar results were seen in the fecal scores. No benefit was demonstrated for the Needle group, thus highlighting the difficulty of vaccinating against *C. diff*.

This study demonstrates superior protection provided by ultrasound-mediated mucosal vaccination against disease, including some diseases lacking a current effective vaccine. According to some embodiments, ultrasound-mediated vaccination may enable biasing of immune response to that of a secreted Immunoglobulin A (IgA) response, which would be beneficial for preventing diseases that invade through mucosal surfaces, such as *C. diff* and the human immunodeficiency virus (HIV).

EXAMPLE 8: LARGE ANIMAL COLITIS MODEL

A disease model for testing a human-scale device would be beneficial. A colitis model was developed in a pig by instilling dextran sodium sulfate (DSS) in the rectum, which results in inflammation. An administration regimen to induce reproducible and lasting colitis in pigs was confirmed based on histology and blood markers. Three animals have been monitored for statistical power.

Figure 41B:
FIGS. 41A and 41B are images illustrating a large animal colitis model in accordance with some embodiments.
Figure 41A:
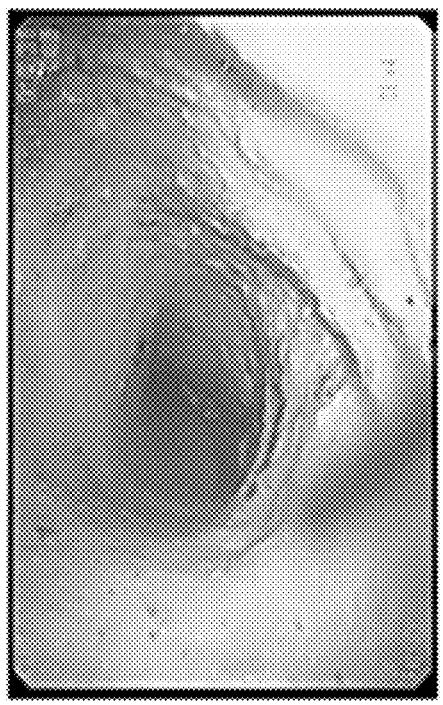
Figure 42B:
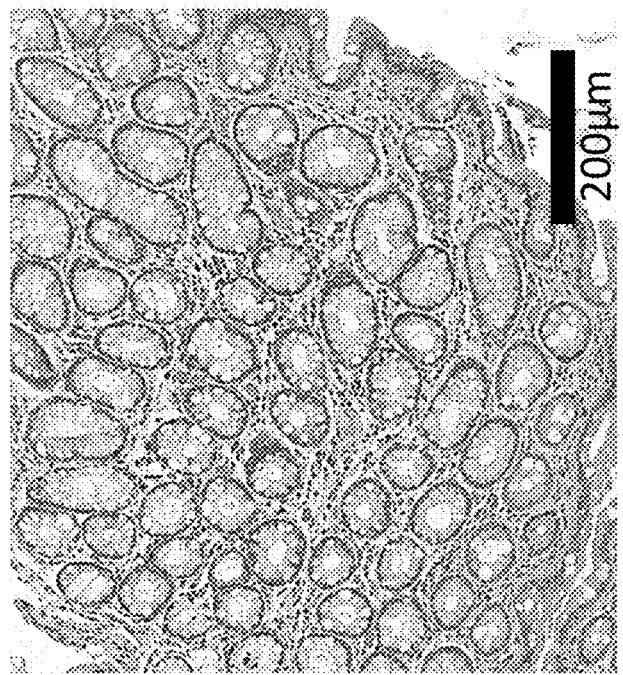
FIGS. 42A-45B are images of varying detail illustrating changes in colonic biopsy histology in a large animal colitis model in accordance with some embodiments.
Figure 42C:
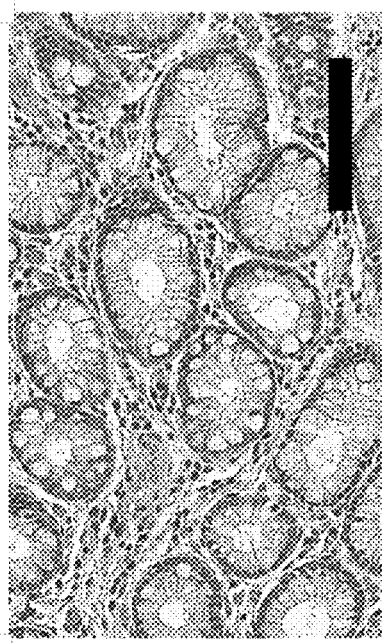
Figure 42A:
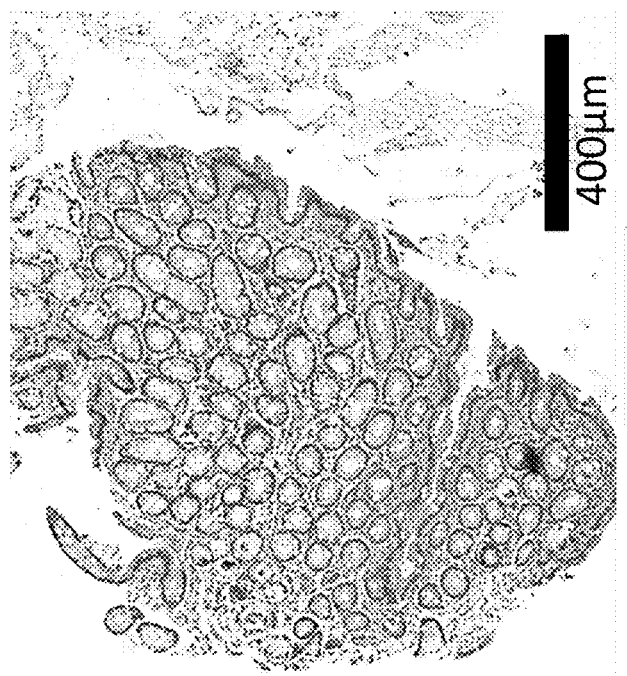
Figure 43B:
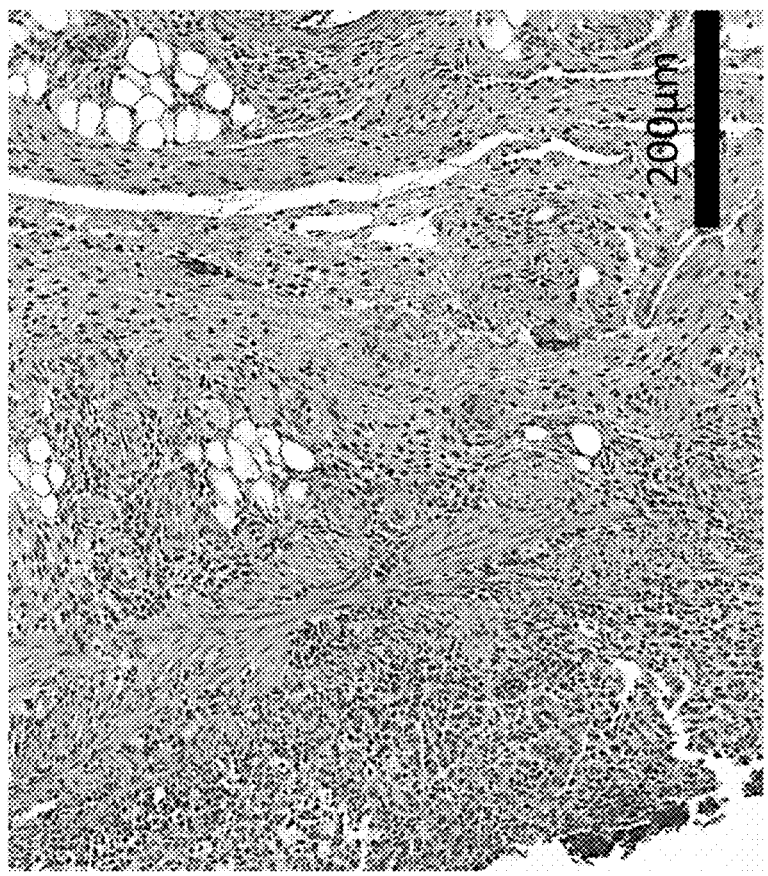
Figure 43A:
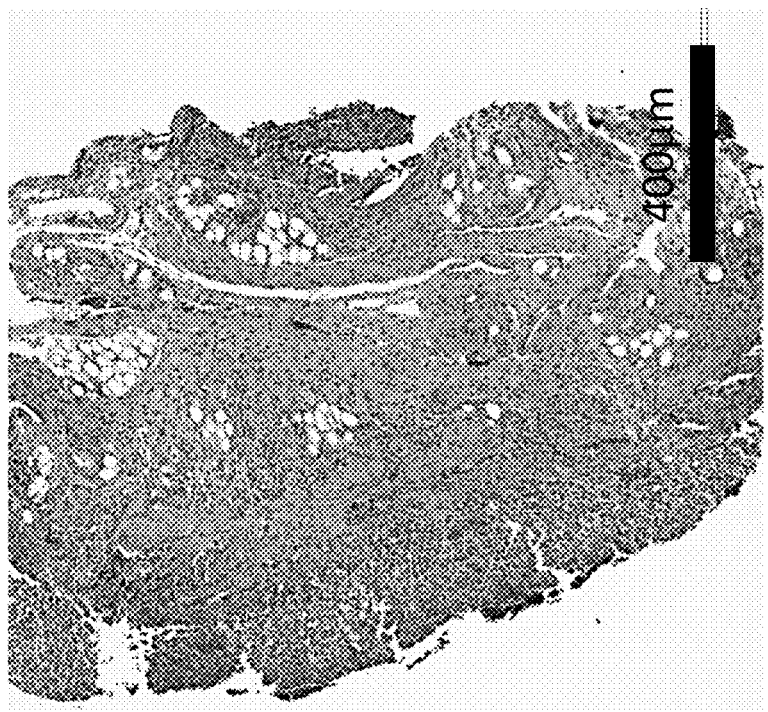
Figure 44B:
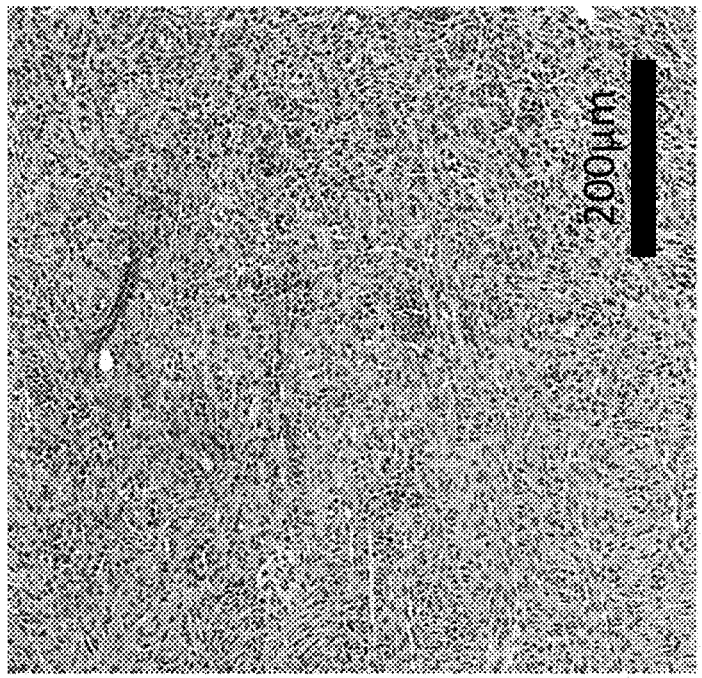
Figure 44A:
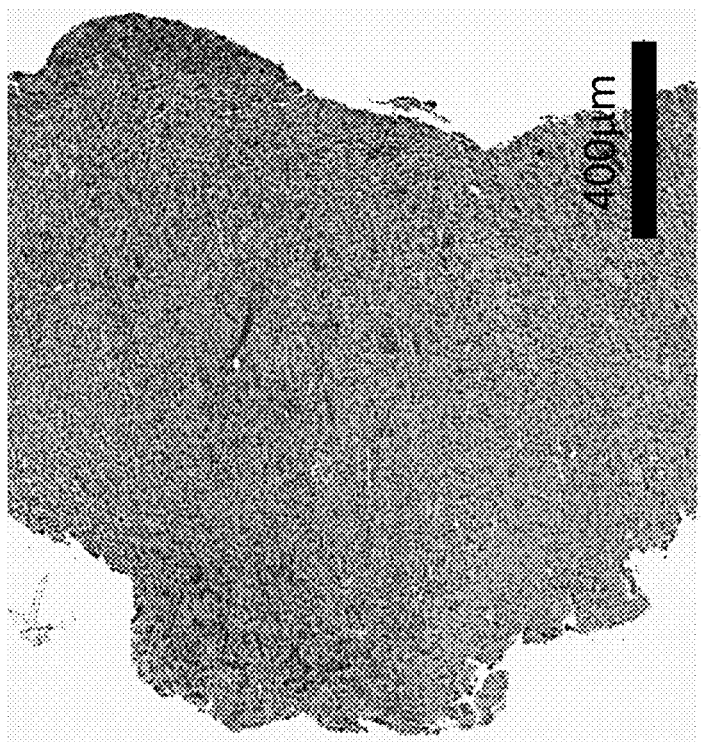
Figure 45B:
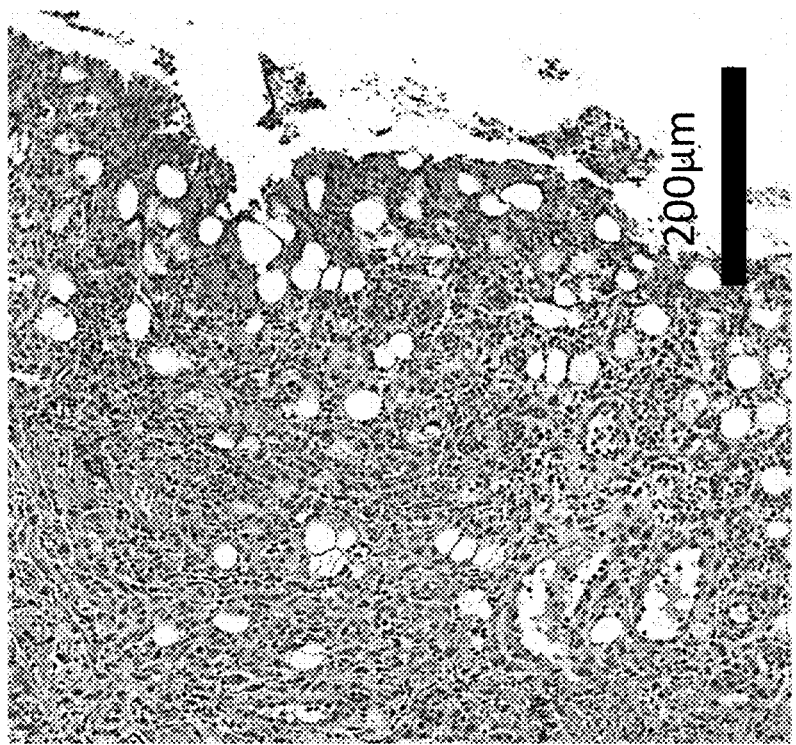
Figure 45A:
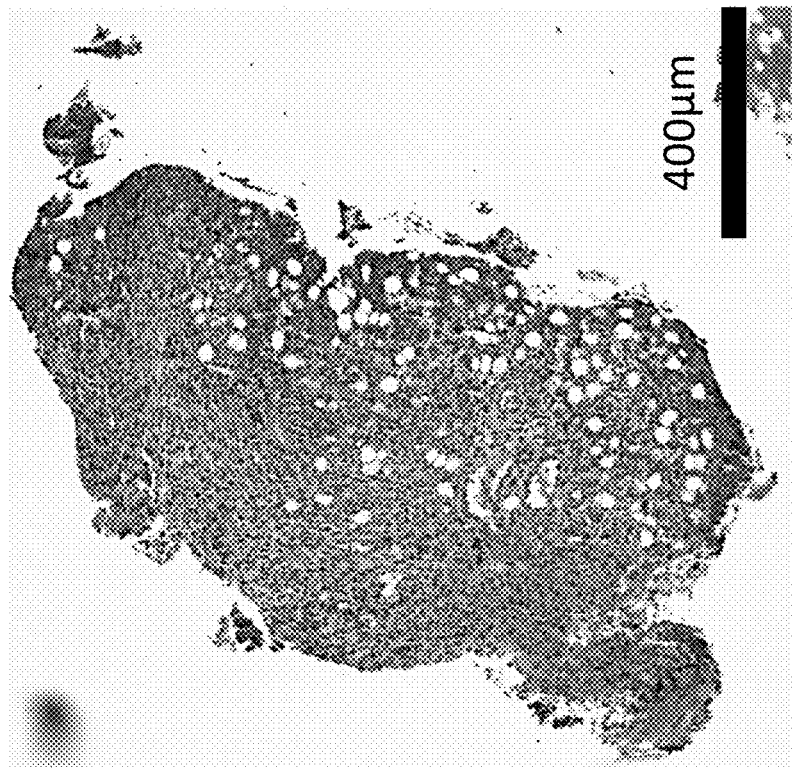

FIG. 41A is an image of a healthy pig colon captured through a colonoscope. FIG. 41B is an image of a pig colon with colitis captured through a colonoscope in accordance with some embodiments. FIGS. 42A-42C are images of varying detail illustrating healthy animal colonic biopsy histology with normal colonic mucosa having structures preserved. FIGS. 43A and 43B are images of varying detail illustrating disease induction colonic biopsy histology taken 7 days post disease induction. These images show total disease, in this case, severe acute colitis. FIGS. 44A and 44B are images of varying detail illustrating disease induction colonic biopsy histology taken 14 days post disease induction. These images show severe acute colitis comparable to presentation on Day 7. FIGS. 45A and 45B are images of varying detail illustrating disease induction colonic biopsy histology taken 21 days post disease induction. These images show severe acute colitis comparable to presentation on Day 14. Fibrinopurulent debris is also visible in these images.

Figure 46B:
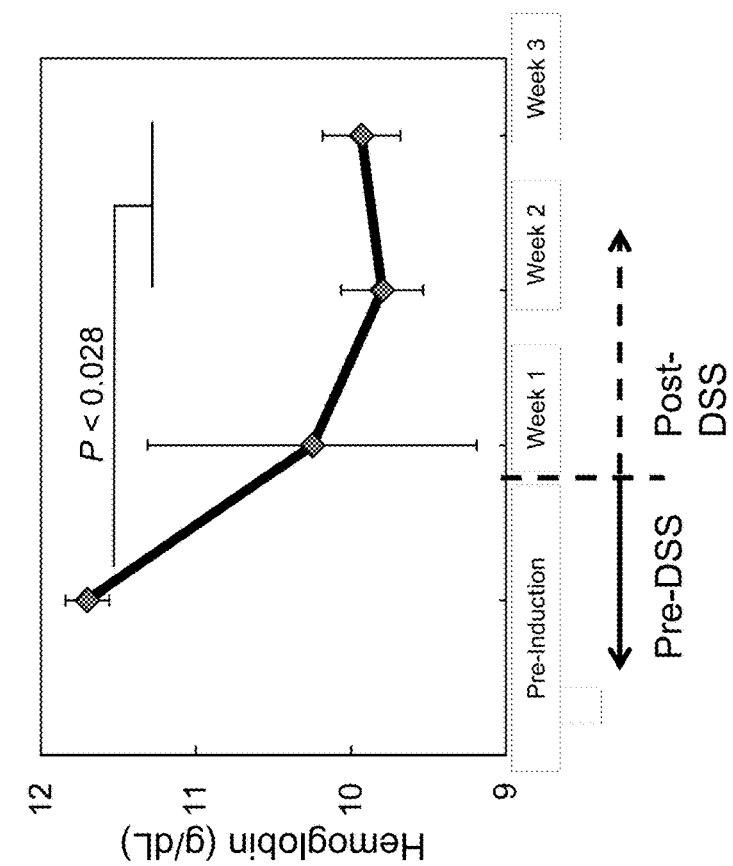
FIGS. 46A and 46B are plots illustrating changes in hematocrit and hemoglobin in a large animal colitis model in accordance with some embodiments.
Figure 46A:
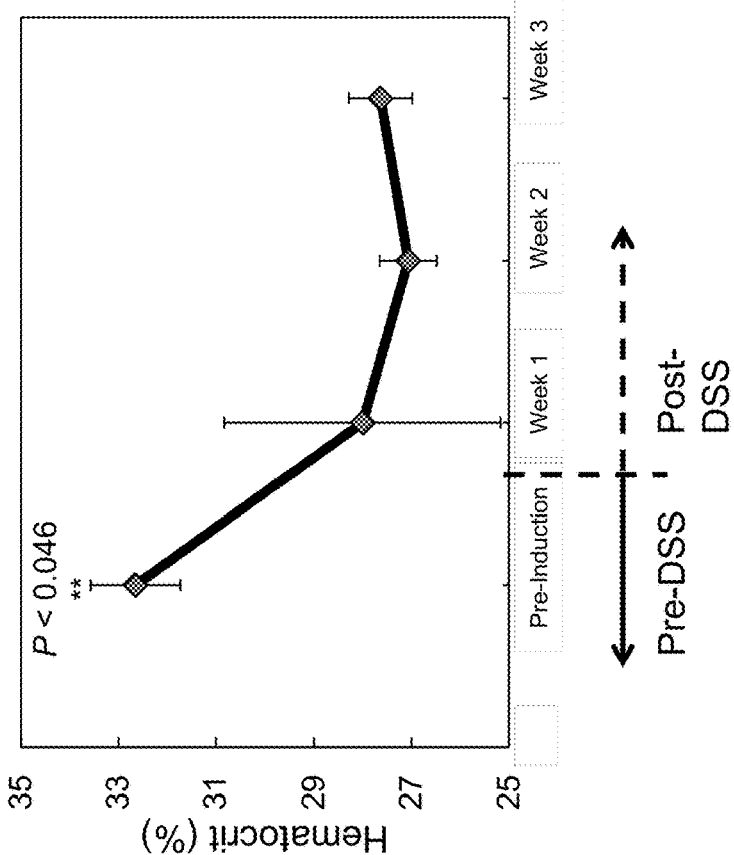

Blood markers hematocrit (i.e., the percentage of red blood cells in the blood) and hemoglobin were evaluated. FIGS. 46A and 46B are plots illustrating the changes in hematocrit and hemoglobin, respectively, over this time period. A statistically significant decrease in both hematocrit and hemoglobin demonstrates blood loss from inflammation in the rectum.

According to some embodiments, this colitis model will allow for testing of human-sized devices for preclinical efficacy.

CONCLUSION

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

The above-described embodiments can be implemented in any of numerous ways. For example, embodiments of designing and making the retention/delivery structures disclosed herein may be implemented using hardware, software or a combination thereof. When implemented in software, the software code can be executed on any suitable processor or collection of processors, whether provided in a single computer or distributed among multiple computers.

Further, it should be appreciated that a computer may be embodied in any of a number of forms, such as a rack-mounted computer, a desktop computer, a laptop computer, or a tablet computer. Additionally, a computer may be embedded in a device not generally regarded as a computer but with suitable processing capabilities, including a Personal Digital Assistant (PDA), a smart phone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks, wired networks or fiber optic networks.

The various methods or processes (e.g., of designing and making the retention/delivery structure disclosed above) outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All publications, patent applications, patents, and other references mentioned herein are incorporated by reference in their entirety, including, but not limited to, the following references:

1. Alex et al., "Distinct Cytokine Patterns Identified from Multiplex Profiles of Murine DSS and TNBS-Induced Colitis," *Inflammatory Bowel Diseases* 15, 341-352 (2009).
2. Barr et al., "Intestinal Drug Absorption and Metabolism I: Comparison of Methods and Models to Study Physiological Factors of In Vitro and In Vivo Intestinal Absorption," *J. Pharm. Sci.* 59, 154-163 (1970).
3. Bawiec et al., "Finite Element Static Displacement Optimization of 20-100 kHz Flexural Transducers for Fully Portable Ultrasound Applicator," *Ultrasonics* 53, 511-517 (2012).
4. Brotchie et al., "Characterization of Acoustic Cavitation Bubbles in Different Sound Fields," *J. Phys. Chem. B* 114, 11010-11016 (2010).
5. Capurso et al., "Development of a pH-Responsive Particulate Drug Delivery Vehicle for Localized Biologic Therapy in Inflammatory Bowel Disease," *Yale J. Biol. & Med.* 84, 285-288 (2011).
6. Cerutti, "Location, Location, Location: B-cell Differentiation in the Gut Lamina Propria," *Mucosal Immunol.* 1, 8-10 (2008).
7. Cerutti et al., "Immunoglobulin Responses at the Mucosal Interface," *Annual Review of Immunology* 29, 273-293 (2011).
8. Ciarleglio et al., "Rowasa Suspension Enema (Mesalamine, USP)," *Gastroenterology Nursing KW*-12 (1989).
9. Coleman et al., "Acoustic Performance and Clinical Use of a Fibreoptic Hydrophone," *Ultrasound in Med. & Biol.* 24, 143-151 (1998).
10. Cooper et al., "Clinicopathologic Study of Dextran Sulfate Sodium Experimental Murine Colitis," *Lab. Invest.* 69(2), 238-249 (1993).
11. Danese et al., "Ulcerative Colitis," *N Engl. J. Med.* 365, 1713-1725 (2011).
12. Dechadilok et al., "Hindrance Factors for Diffusion and Convection in Pores," *Indus. &Eng. Chem. Res.* 45, 6953-6959 (2006).
13. Ensign et al., "Oral Drug Delivery with Polymeric Nanoparticles: The Gastrointestinal Mucus Barriers," *Advanced Drug Delivery Reviews* 64, 557-570 (2012).
14. Frieri et al., "Mucosal 5-aminosalicylic Acid Concentration Inversely Correlates with Severity of Colonic Inflammation in Patients with Ulcerative Colitis," *Gut* 47, 410-414 (2000).
15. Giannasca et al., "Serum Antitoxin Antibodies Mediate Systemic and Mucosal Protection from *Clostridium Difficile* Disease in Hamsters," *Infection & Immunity* 67(2), 527-538 (1999).
16. Holland, "Thresholds for Transient Cavitation Produced by Pulsed Ultrasound in a Controlled Nuclei Environment," *J. Acoust. Soc. Am.* 88, 2059-2069 (1990).

17. Horowitz et al., "The Nuclear Permeability, Intracellular Distribution, and Diffusion of Inulin in the Amphibian Oocyte," *J. Cell Biol.* 60, 405 (1974).
18. Karaca-Mandic et al., "Impact of New Drugs and Biologics on Colorectal Cancer Treatment and Costs," *J. Oncology Practice* 7, e30s-e37s (2011).
19. Kedia, "Once-Daily MMX Mesalamine for the Treatment of Mild-to-Moderate Ulcerative Colitis," *Therapeutics & Clinical Risk Management* 3, 919-927 (2007).
20. Kennedy, "Innovation: High-Intensity Focused Ultrasound in the Treatment of Solid Tumours," *Nat. Rev. Cancer* 5, 321-327 (2005).
21. Kyne et al, "*Clostridium Difficile* Toxoid Vaccine in Recurrent *C. difficile*-Associated Diarrhea," *Gastroenterology* 128(3), 764-770 (2005).
22. Leighton, *The Acoustic Bubble* (Academic Press 1997).
23. Li et al., "Passive Cavitation Detection during Pulsed HIFU Exposures of Ex Vivo Tissues and In Vivo Mouse Pancreatic Tumors," *Ultrasound in Med. & Biol.* 40, 1523-1534 (2014).
24. Lin et al., "Factors Affecting Responsivity of Unilamellar Liposomes to 20 kHz Ultrasound," *Langmuir* 20, 6100-6106 (2004).
25. Lin et al., "PEG Lipids and Oligo(ethylene glycol) Surfactants Enhance the Ultrasonic Permeabilizability of Liposomes," *Langmuir* 19, 1098-1105 (2003).
26. Liu et al., "Non-Invasive Assessment and Control of Ultrasound-Mediated Membrane Permeabilization," *Pharm. Res.* 15, 918-924 (1998).
27. Malkov et al., "Multiplexed Measurements of Gene Signatures in Different Analytes Using the Nanostring nCounter™ Assay System," *BMC Res. Notes* 2, 80 (2009).
28. Marshall et al., "Putting Rectal 5-Aminosalicylic Acid in Its Place: The Role in Distal Ulcerative Colitis," *Am. J. Gastroenterology* 95, 1628-1636 (2000).
29. Morrow et al., "DNA Drugs Come of Age," *Scientific American* 303, 48-53 (2010).
30. Naganuma et al., "Measurement of Colonic Mucosal Concentrations of 5-Aminosalicylic Acid Is Useful for Estimating Its Therapeutic Efficacy in Distal Ulcerative Colitis: Comparison of Orally Administered Mesalamine and Sulfasalazine," *Inflammatory Bowel Diseases* 7, 221-225 (2001).
31. Nakashima et al., "Rebamipide Enema is Effective for Treatment of Experimental Dextran Sulfate Sodium Induced Colitis in Rats," *Dig. Dis. Sci.* 50, S124-S131 (2005).
32. Neurath, "Cytokines in Inflammatory Bowel Disease," *Nature Reviews Immunology* 14, 329-342 (2014).
33. Neurath, "New Targets for Mucosal Healing and Therapy in Inflammatory Bowel Diseases," *Mucosal Immunol.* 7, 6-19 (2014).
34. Pavlin et al., "Clinical Use of Ultrasound Biomicroscopy," *Ophthalmology* 98, 287-295 (1991).
35. Peck et al., "Hindered Diffusion of Polar Molecules Through and Effective Pore Radii Estimates of Intact and Ethanol Treated Human Epidermal Membrane," *Pharm. Res.* 11, 1306-1314 (1994).
36. Pecot et al., "RNA Interference in the Clinic: Challenges and Future Directions," *Nat. Rev. Cancer* 11, 59-67 (2011).
37. Pelekasis et al., "Secondary Bjerknes Forces Between Two Bubbles and the Phenomenon of Acoustic Streamers," *J. Fluid Mech.* 500, 313-347 (1999).
38. Prentice et al., "Membrane Disruption by Optically Controlled Microbubble Cavitation," *Nat. Phys.* 1, 107-110 (2005).
39. Sann et al., "Efficacy of Drugs Used in the Treatment of IBD and Combinations Thereof in Acute DSS-Induced Colitis in Mice," *Life Sci.* 92, 708-718 (2013).
40. Schoellhammer et al., "Ultrasound-Mediated Gastrointestinal Drug Delivery," *Sci. Translational Med.* 7(310), 310ra168 (2015).
41. Schultz et al., "Determination of the Effective Hydrodynamic Radii of Small Molecules by Viscometry," *J Gen. Physiol.* 44, 1189 (1961).
42. Seibold et al., Topical Therapy Is Underused in Patients with Ulcerative Colitis," *J. Crohn's & Colitis JA* 8, 56-63 PB (2014).
43. Seto et al., "Effects of Ultrasound and Sodium Lauryl Sulfate on the Transdermal Delivery of Hydrophilic Permeants: Comparative In Vitro Studies with Full-Thickness and Split-Thickness Pig and Human Skin, *J. Controlled Release* 145, 26-32 (2010).
44. Škalko-Basnet, "Biologics: The Role of Delivery Systems in Improved Therapy," *Biologics: Targets & Therapy* 8, 107-114 (2014).
45. Stein, *Channels, Carriers, and Pumps: An Introduction to Membrane Transport* (Elsevier Sci. 2012).
46. Tezel et al., "Description of Transdermal Transport of Hydrophilic Solutes During Low-Frequency Sonophoresis Based on a Modified Porous Pathway Model," *J Pharm. Sci.* 92, 381-393 (2003).
47. Tezel et al., "Low-Frequency Ultrasound as a Transcutaneous Immunization Adjuvant," *Vaccine* 23(29) 3800-3807 (2005).
48. Tones et al., "Evaluation of Formalin-Inactivated Clostridium-Difficile Vaccines Administered by Parenteral and Mucosal Routes of Immunization in Hamsters," *Infection & Immunity* 63, 4619-4627 (1995). Veereman, "Pediatric Applications of Inulin and Oligofructose," *J Nutrition* 137, 2585S-2589S (2007).
49. Vong et al., "An Orally Administered Redox Nanoparticle That Accumulates in the Colonic Mucosa and Reduces Colitis in Mice," *Gastroenterology* 143, 1027-1036.e3 (2012).
50. Wang et al., "A Chimeric Toxin Vaccine Protects Against Primary and Recurrent *Clostridium difficile* Infection," *Infection & Immunity* 80(8), 2678-2688 (2012).
51. Wilson et al., "Orally Delivered Thioketal Nanoparticles Loaded with TNF-α-siRNA Target Inflammation and Inhibit Gene Expression in the Intestines," *Nature Materials* 9(11), 923-928 (2010).
52. Wirtz et al., "Chemically Induced Mouse Models of Intestinal Inflammation," *Nature Protocols* 2, 541-546 (2007).
53. Wolf et al., "Inflammatory Bowel Disease: Sorting Out the Treatment Options," *Cleveland Clinic J. Med.* 69, 621-626 (2002).
54. Zhu et al., "Large Intestine-Targeted, Nanoparticle-Releasing Oral Vaccine to Control Genitorectal Viral Infection," *Nature Med.* 18, 1291-1296 (2012).

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A kit for use in administering a substance contained in a fluid, the kit comprising:

a device for administering the substance, the device comprising:
   an elongated body having a proximal end and a distal end, the elongated body defining an internal chamber extending between the proximal end and the distal end to direct the substance to the distal end;
   a tip for connecting to the distal end, the tip to be at least partially inserted into an orifice of a body lumen of a subject, the tip comprising:
     a concave region for creating a seal against the orifice during use; and
     a delivery region including an opening to pass the fluid from the internal chamber into the body lumen, wherein a diameter of the delivery region is greater than a diameter of the concave region; and
   a transducer disposed in the elongated body to generate an ultrasound wave; and
   a shaft coupled to the transducer to emit the ultrasound wave into the body lumen, wherein a proximal end of the shaft is coupled to the transducer within the elongated body and a distal end of the shaft extends beyond the tip and into the body lumen, wherein the distal end of the shaft defines a plane such that a longitudinal axis of the device is orthogonal to the plane, and wherein the shaft is configured to emit the ultrasound wave along the longitudinal axis and into the fluid in the body lumen away from the distal end of the elongated body to form cavitation bubbles in the fluid that implode to create microjets that impinge upon the tissue to administer the substance to tissue in the body lumen; and
   a cartridge to be inserted in the internal chamber to establish fluid communication with the device, the cartridge comprising:
     a housing defining a reservoir comprising the fluid.

2. A device for administering a substance contained in a fluid, the device comprising:
   an elongated body having a proximal end and a distal end, the elongated body defining an internal chamber extending between the proximal end and the distal end to direct the fluid to the distal end, the distal end connected with a tip, the tip to be at least partially inserted into an orifice of a body lumen of a subject, the tip comprising:
     a concave region for creating a seal against the orifice during use; and
     a delivery region including a flat distal end and an opening to pass the fluid from the internal chamber into the body lumen, wherein the opening is oriented in a radial direction with respect to the device, and wherein a diameter of the delivery region is greater than a diameter of the concave region; and
   a transducer disposed in the elongated body to generate an ultrasound wave; and
   a shaft coupled to the transducer to emit the ultrasound wave into the body lumen, wherein a proximal end of the shaft is coupled to the transducer within the elongated body and a distal end of the shaft extends beyond the tip and configured to extend into the body lumen, and wherein the shaft is configured to emit the ultrasound wave into the fluid in the body lumen away from the distal end of the elongated body to form cavitation bubbles in the fluid that implode to create microjets that impinge upon tissue in the body lumen to administer the substance to the tissue.

3. The device of claim 2, further comprising a sheath, the sheath comprising:
a cover to protect at least a portion of the device, including the tip and the distal end of the shaft, from direct contact with the body lumen, the cover defining a perforation for aligning with the opening, wherein at least one of:
the sheath comprises an elastic band around the cover configured to reduce exposure of the device to the body lumen;
the cover comprises of an elastic wrap configured to reduce exposure of the device to the body lumen;
the cover comprises a rigid piece for slipping over the tip and the distal end of the shaft;
the cover comprises a first rigid piece and a second rigid piece to install from opposite sides of the tip and the distal end of the shaft such that the first rigid piece connects to the second rigid piece; or
the cover comprises a first rigid piece joined by a hinge at the end of the and the distal end of the shaft to a second rigid piece.

4. The device of claim 2, wherein the tip has at least one of:
a thermocouple for monitoring temperature;
a coating for reducing friction upon the at least partial insertion into the orifice;
a length of about 1 cm to about 10 cm; or
a radius of about 1 cm to about 3 cm.

5. The device of claim 2, further comprising a pump to drive the substance through the opening when the device is activated.

6. The device of claim 2, further comprising a thermocouple for monitoring temperature.

7. The device of claim 2, wherein the internal chamber comprises a port assembly for receiving a cartridge, the cartridge comprising:
a housing defining a reservoir comprising the substance.

8. The device of claim 2, wherein the internal chamber comprises a reservoir internal to the elongated body to receive the substance.

9. The device of claim 2, wherein at least a portion of the device is at least one of reusable or waterproof.

10. The device of claim 2, wherein the elongated body is configured to be at least one of hand-held or portable.

11. The device of claim 2, wherein the elongated body has at least one of:
a cylindrical shape around an axis from the proximal end to the distal end;
a taper from the proximal end to the distal end;
a length of about 14 cm to about 40 cm from the proximal end to the distal end;
a first diameter at the proximal end of about 4 cm to about 6 cm; or
a second diameter at the distal end of about 1 cm to about 3 cm.

12. The device of claim 2, wherein the shaft has at least one of:
a length of about 1 cm to about 7 cm;
a diameter of about 0.1 cm to about 2 cm; or
at least one protrusion along the shaft, the at least one protrusion being up to 1 cm beyond the diameter of the shaft.

13. The device of claim 2, wherein a frequency of the ultrasound wave is from about 15 kHz to about 500 kHz.

14. The device of claim 2, wherein a frequency of the ultrasound wave is from about 20 kHz to about 100 kHz.

15. The device of claim 2, wherein a frequency of the ultrasound wave is from about 500 kHz to about 3000 kHz.

16. The device of claim 2, wherein the opening is a first opening, the delivery region including a plurality of openings including the first opening to pass the substance from the internal chamber.

17. The device of claim 16, wherein an axis of each of the plurality of openings is angled about 45° to about 90° with respect to the device.

18. The device of claim 2, wherein the transducer comprises a piezoelectric element.

19. The device of claim 18, wherein the piezoelectric element comprises at least one of a crystal, a ceramic, or polymer.

20. The device of claim 2, wherein the transducer is configured for emitting a plurality of ultrasound waves from the tip and into the body lumen.

21. The device of claim 20, wherein the plurality of ultrasound waves have a plurality of associated frequencies.

22. The device of claim 2, wherein the elongated body is configured to enable grip by a user.

23. The device of claim 22, wherein at least a portion of the elongated body comprises a non-slip material, the non-slip material including at least one of a rubber, a silicone, an elastomer, or a plastic.

24. The device of claim 22, wherein at least a portion of the elongated body comprises a surface texture for increasing traction, the surface texture including at least one of lay, roughness, or waviness.

25. A method for administering a substance contained in a fluid, the method comprising:
inserting into an orifice of a body lumen of a subject at least a portion of a tip of a device, the device defining an axis, the tip including a concave region for creating a seal against the orifice during use;
passing, via a delivery region including an opening in the tip, the fluid into the body lumen radially with respect to the axis of the device, wherein a diameter of the delivery region is greater than a diameter of the concave region; and
at least one of simultaneously or subsequently emitting, via a shaft coupled to a transducer, wherein the shaft extends beyond the tip and into the body lumen, an ultrasound wave into the body lumen to form cavitation bubbles in the fluid in the body lumen that implode to create microjets that impinge upon the tissue to administer the substance to tissue in the body lumen.

26. The method of claim 25, wherein the subject is a mammal.

27. The method of claim 25, wherein the subject is a human.

28. The method of claim 25, wherein the body orifice is a rectum of the subject.

29. The method of claim 25, the passing including passing the substance for a duration up to about 30 seconds.

30. The method of claim 25, wherein the administering is self-administration.

31. The method of claim 25, wherein a duration of the emitting comprises a total duration of ultrasound exposure lasting up to about 2 minutes.

32. The method of claim 25, wherein the substance comprises at least one of hydrocortisone or mesalamine.

33. The method of claim 25, wherein the substance is administered to at least one of treat or mitigate symptoms of at least one of proctitis, inflammatory bowel disease, or irritable bowel syndrome.

34. The method of claim 25, wherein a duration of the emitting lasts up to about 30 minutes.

35. The method of claim 34, wherein the duration of the emitting lasts from about 1 minute to about 5 minutes.

* * * * *